United States Patent
Watanabe et al.

(10) Patent No.: US 12,398,125 B2
(45) Date of Patent: Aug. 26, 2025

(54) NITROGEN-CONTAINING SATURATED HETEROCYCLYL DERIVATIVE

(71) Applicant: Sumitomo Pharma Co., Ltd., Osaka (JP)

(72) Inventors: Hitoshi Watanabe, Osaka (JP); Shuya Yamada, Osaka (JP); Katsushi Kitahara, Osaka (JP); Mariko Kobayashi, Osaka (JP)

(73) Assignee: Sumitomo Pharma Co., Ltd., Osaka (JP)

( * ) Notice: Subject to any disclaimer, the term of this patent is extended or adjusted under 35 U.S.C. 154(b) by 0 days.

(21) Appl. No.: 18/558,337

(22) PCT Filed: Jul. 28, 2023

(86) PCT No.: PCT/JP2023/027829
§ 371 (c)(1),
(2) Date: Oct. 31, 2023

(87) PCT Pub. No.: WO2024/024962
PCT Pub. Date: Feb. 1, 2024

(65) Prior Publication Data
US 2025/0051305 A1   Feb. 13, 2025

(30) Foreign Application Priority Data

Jul. 29, 2022 (JP) ................................. 2022-121677

(51) Int. Cl.
| | | |
|---|---|---|
| *C07D 405/14* | (2006.01) |
| *A61K 31/4439* | (2006.01) |
| *A61K 31/4545* | (2006.01) |
| *A61K 31/497* | (2006.01) |
| *A61K 31/501* | (2006.01) |
| *A61K 31/506* | (2006.01) |
| *A61K 31/5377* | (2006.01) |
| *A61K 31/553* | (2006.01) |
| *A61P 25/16* | (2006.01) |
| *C07D 401/14* | (2006.01) |
| *C07D 413/14* | (2006.01) |
| *C07D 491/04* | (2006.01) |
| *C07D 491/08* | (2006.01) |

(52) U.S. Cl.
CPC ........ *C07D 405/14* (2013.01); *A61K 31/4439* (2013.01); *A61K 31/4545* (2013.01); *A61K 31/497* (2013.01); *A61K 31/501* (2013.01); *A61K 31/506* (2013.01); *A61K 31/5377* (2013.01); *A61K 31/553* (2013.01); *A61P 25/16* (2018.01); *C07D 401/14* (2013.01); *C07D 413/14* (2013.01); *C07D 491/04* (2013.01); *C07D 491/08* (2013.01)

(58) Field of Classification Search
CPC .............................. C07D 405/14; A61P 25/16
USPC ....................................................... 514/210.2
See application file for complete search history.

(56) References Cited

U.S. PATENT DOCUMENTS

| | | |
|---|---|---|
| 2010/0331298 A1 | 12/2010 | Ben-Zeev et al. |
| 2011/0178060 A1 | 7/2011 | Shirai et al. |
| 2011/0293520 A1 | 12/2011 | Giese et al. |
| 2013/0035342 A1 | 2/2013 | Masliah et al. |
| 2021/0107920 A1 | 4/2021 | Bell et al. |

FOREIGN PATENT DOCUMENTS

| | | |
|---|---|---|
| WO | WO 2010/000372 A2 | 1/2010 |
| WO | WO 2010/032856 A1 | 3/2010 |
| WO | WO 2011/084642 A1 | 7/2011 |
| WO | WO 2016/073420 A1 | 5/2016 |
| WO | WO 2019/180185 A1 | 9/2019 |
| WO | WO 2024/024961 A1 | 2/2024 |

OTHER PUBLICATIONS

International Search Report & Written Opinion Issued Oct. 3, 2023, in PCT/JP2023/027829, filed on Jul. 28, 2023, (with English translation of Categories), 8 pages.

(Continued)

*Primary Examiner* — Kahsay Habte
(74) *Attorney, Agent, or Firm* — Oblon, McClelland, Maier & Neustadt, L.L.P.

(57) ABSTRACT

The present invention relates to a medicament for treating or preventing central nervous system disease whose cause is related to abnormal aggregation of proteins in the brain, which comprises as an active ingredient a compound of formula (1) or a pharmaceutically acceptable salt thereof, wherein $R^1$ and $R^2$ are hydrogen, etc., $R^3$ and $R^4$ are hydrogen, $C_{1-6}$ alkyl, etc., $R^5$ is halogen, $C_{1-6}$ alkyl, etc., $R^6$ is hydrogen, halogen, etc., X is oxygen, etc., Y is carbon, etc., m and n are an integer of 0, 1, etc., r and s are 0, 1, 2, etc., Hy is pyridine ring, etc., which has an action of suppressing or reducing the accumulation of abnormal aggregation of proteins in the brain.

(1)

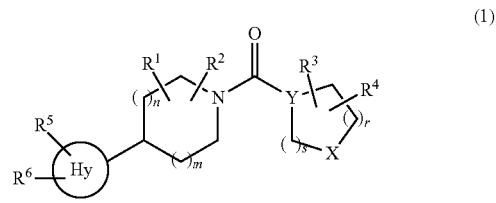

43 Claims, 4 Drawing Sheets

(56) References Cited

OTHER PUBLICATIONS

CAS Registry No. 2249485-17-2, Database Registry, [online], Nov. 18, 2018 (date of receipt), [date of search: Sep. 20, 2023], retrieved from: STN CAS Registry No. 2249485-17-2, 1 page.
Ma, Y. et al. "Substituted piperidines as HDM2 inhibitors", Bioorganic & Medical Chemistry Letters, 2014, vol. 24, No. 4. pp. 1026-1030, 5 pages.

NITROGEN-CONTAINING SATURATED HETEROCYCLYL DERIVATIVE

CROSS-REFERENCE TO RELATED APPLICATIONS

The present application is a 35 U.S.C. § 371 national stage patent application of International Patent Application PCT/JP2023/027829, filed on Jul. 28, 2023, which is based on and claims the benefits of priority to Japanese Application No. 2022-121677, filed on Jul. 29, 2022. The entire contents of these applications are incorporated herein by reference.

TECHNICAL FIELD

The present invention relates to a nitrogen-containing saturated heterocyclyl derivative or a pharmaceutically acceptable salt thereof which has an action of suppressing or reducing the accumulation of abnormal aggregation of proteins in the brain, and a medicament comprising the derivative as an active ingredient, for treating or preventing central nervous system disease whose cause is related to abnormal aggregation of proteins in the brain. In addition, the present invention provides a method for reproducing Parkinson's disease pathology with neurospheroids, and a method for evaluating the amount of α-synuclein aggregates using the reproducing method.

BACKGROUND OF THE INVENTION

Neurodegenerative diseases which mainly include Alzheimer's disease, Parkinson's disease, Huntington's disease, and amyotrophic lateral sclerosis are thought to be caused by the formation of abnormally-aggregated proteins in a patient's brain, the aggregates exhibiting neurotoxicity, and thereby the onset and progression of the diseases.

Constituent proteins of the aggregates differ depending on diseases, and α-synuclein has been reported as a major constituent of aggregates that cause Parkinson's disease. It has been reported that abnormally-aggregated α-synuclein exhibits toxicity, and that aggregated α-synuclein propagates between cells.

As an agent for treating Parkinson's disease, the administration of levodopa which is a dopamine precursor is available as symptomatic therapy, but no fundamental treatment has been established at present. In recent years, some developments of disease-modifying drugs for Parkinson's disease have been vigorously pursued, but there are currently no reports of agents undergoing clinical trials that strongly suppress or reduce the accumulation of α-synuclein aggregates.

It is considered that α-synuclein aggregates are the causative background of Lewy body diseases including Parkinson's disease (dementia with Lewy body, multiple system atrophy, Gaucher disease, infantile neuroaxonal dystrophy, etc.). Accordingly, drugs that suppress or reduce the accumulation of α-synuclein aggregates are expected to exhibit therapeutic effects on these diseases.

Until now, no in vitro evaluation system that reproduces endogenous α-synuclein aggregates in neurons has been reported, and many evaluation systems for α-synuclein pathology are indicated by the amount of phosphorylated α-synuclein increased due to the addition of in vitro-synthesized α-synuclein oligomers. After all, it has not been possible to evaluate an action of suppressing the accumulation of α-synuclein aggregates or reducing accumulated α-synuclein aggregates.

Until now, NPT200-11 (Neuropore) and Anle138b (MODAG) have been reported as drugs that can inhibit the formation of α-synuclein aggregates. However, these drugs had been evaluated about the action of inhibiting the ability to form aggregates when artificially aggregating α-synuclein in vitro (Patent literatures 1 and 2).

It has also been reported that (4aR,8aS)-hexahydro-2H-pyrido[4,3-b][1,4]oxazin-3(4H)-one derivatives such as (4aR,8aS)-6-{4-[5-(trifluoromethyl)pyridin-3-yl]piperidine-1-carbonyl}hexahydro-2H-pyrido[4,3-b][1,4]oxazin-3(4H)-one and (4aR,8aS)-6-[4-(5-ethylpyridin-3-yl)piperidine-1-carbonyl]hexahydro-2H-pyrido[4,3-b][1,4]oxazin-3(4H)-one have an action of inhibiting monoacylglycerol lipase (MAGL), which are effective for neuroinflammation, neurodegenerative disease, etc. (Patent literature 3). In addition, It has also been reported that (azetidin-1-yl) (phenyl)methanone derivatives such as 2-chloro-3-{3-[6-(trifluoromethyl)pyridin-3-yl]azetidine-1-carbonyl}-4-[(1,1,1-trifluoropropan-2-yl)oxy]benzonitrile and 2-methoxy-3-{3-[6-(trifluoromethyl)pyridin-3-yl]azetidine-1-carbonyl}-4-[(1,1,1-trifluoropropan-2-yl)oxy]benzonitrile have an action of inhibiting glycine transporter 1 (GlyT1), which are effective for neurodegenerative disease, etc. (Patent literature 4).

However, all of these compounds are different from the nitrogen-containing saturated heterocyclyl derivative of the present invention. And, these documents neither disclose nor suggest anything about the nitrogen-containing saturated heterocyclyl derivative of the present invention. In addition, they do not suggest the action of suppressing or reducing the accumulation of abnormal aggregation of proteins in the brain.

PRIOR ART

Patent Reference

[Patent literature 1] WO 2011/084642
[Patent literature 2] WO 2010/000372
[Patent literature 3] WO 2019/180185
[Patent literature 4] WO 2016/073420

SUMMARY OF INVENTION

Technical Problem

The purpose of the present invention is to provide a compound or a pharmaceutically acceptable salt thereof for use in preventing or treating central nervous system disease, which is characterized by an action of suppressing or reducing the accumulation of abnormal aggregation of proteins in the brain, and a composition comprising the compound. In addition, the purpose of the present invention is also to provide a method for reproducing Parkinson's disease pathology with neurospheroids, and a method for evaluating the amount of α-synuclein aggregates using the reproducing method.

Solution to Problem

The present inventors have extensively studied to reach the above purpose, and then have found that a compound of formula (1) below or a pharmaceutically acceptable salt thereof (referred to as "the present compound" as appropriate) has an action of suppressing or reducing the accumulation of abnormal aggregation of proteins in the brain, and a method for reproducing Parkinson's disease pathology with neurospheroids, and have found a method for evaluating the amount of α-synuclein aggregates using the reproducing method. Based upon the findings, the present invention has been achieved. The present invention is as described below.

(Item 1)
A compound of formula (1):

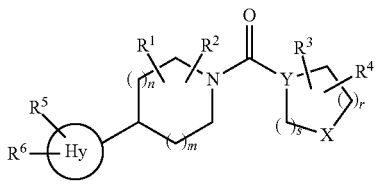

or a pharmaceutically acceptable salt thereof, wherein
X is oxygen or $NR^7$,
$R^7$ is hydrogen, $C_{1-3}$ alkyl optionally-substituted with 1 to 3 the same or different halogen atoms, or cyclopropyl,
Y is CH or nitrogen,
m is 0, 1, or 2,
n is 0 or 1,
r is 0, 1, 2, 3, or 4,
s is 0, 1, or 2,
provided that when s is 0, then Y is CH, and r is 1, 2, 3, or 4,
when s is 1, then Y is CH, and r is 0, 1, 2, or 3, and
when s is 2, then r is 1 or 2,
$R^1$ is hydrogen, halogen, methyl, or hydroxy,
$R^2$ is hydrogen, halogen, methyl, or hydroxy,
$R^3$ is hydrogen, or $C_{1-3}$ alkyl,
$R^4$ is hydrogen, or $C_{1-3}$ alkyl,
or, $R^3$ and $R^4$ may be optionally taken together to form a bridged methylene or a bridged ethylene,
$R^5$ is halogen, $C_{1-3}$ alkyl optionally-substituted with 1 to 3 the same or different halogen atoms, or $C_{1-3}$ alkoxy optionally-substituted with 1 to 3 the same or different halogen atoms,
$R^6$ is hydrogen, halogen, $C_{1-3}$ alkyl optionally-substituted with 1 to 3 the same or different halogen atoms, or $C_{1-3}$ alkoxy optionally-substituted with 1 to 3 the same or different halogen atoms, and
Hy is pyridine ring, pyridazine ring, pyrimidine ring, or pyrazine ring,
provided that
(I) when Hy accompanied with $R^5$ and $R^6$ is 5-fluoropyridin-2-yl, and m and n are 1, then r is 0, and s is 1,
(II) when Hy accompanied with $R^5$ and $R^6$ is 6-methoxypyridin-3-yl, m and n are 1, and X is oxygen, then r is 0, and s is 1,
(III) when Hy accompanied with $R^5$ and $R^6$ is 5-methoxypyridin-2-yl, m and n are 1, and X is $NR^7$, then r is 0, and s is 1,
(IV) when $R^5$ is methyl, and $R^6$ is hydrogen, then r is 0, and s is 1,
but,
(I') Hy accompanied with $R^5$ and $R^6$ is not 4,6-dimethylpyrimidin-2-yl, or 5-bromopyrimidin-2-yl,
(II') when Hy accompanied with $R^5$ and $R^6$ is 5-chloropyridin-2-yl, then m and n are 1, and both $R^1$ and $R^2$ are not hydrogen,
provided that the following compounds are excluded
(III') (1-isopropylpiperidin-4-yl){3-(2-methoxypyridin-3-yl)pyrrolidin-1-yl}methanone, and
(IV') (3-ethoxyoxetan-3-yl) [3-{4-(trifluoromethyl)pyrimidin-2-yl}pyrrolidin-1-yl]methanone.

(Item 2)
The compound of Item 1 or a pharmaceutically acceptable salt thereof, wherein m is 1, and n is 1.

(Item 3)
The compound of Item 1 or 2 or a pharmaceutically acceptable salt thereof, wherein $R^1$ and $R^2$ are independently hydrogen, methyl, or fluorine.

(Item 4)
The compound of Item 1 or 2 or a pharmaceutically acceptable salt thereof, wherein $R^1$ and $R^2$ are hydrogen.

(Item 5)
The compound of any one of Items 1 to 4 or a pharmaceutically acceptable salt thereof, wherein X is oxygen, NH, or NMe.

(Item 6)
The compound of any one of Items 1 to 5 or a pharmaceutically acceptable salt thereof, wherein $R^3$ is hydrogen.

(Item 7)
The compound of any one of Items 1 to 6 or a pharmaceutically acceptable salt thereof, wherein $R^4$ is methyl or ethyl.

(Item 8)
The compound of any one of Items 1 to 7 or a pharmaceutically acceptable salt thereof, wherein Y is CH.

(Item 9)
The compound of any one of Items 1 to 8 or a pharmaceutically acceptable salt thereof, wherein s is 1.

(Item 10)
The compound of any one of Items 1 to 9 or a pharmaceutically acceptable salt thereof, wherein r is 0, and s is 1.

(Item 11)
The compound of Item 1 or a pharmaceutically acceptable salt thereof, wherein the compound is presented in formula (2):

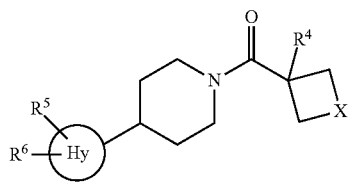

wherein
X is oxygen, NH, or NMe,
$R^4$ is methyl or ethyl,
$R^5$ is halogen, $C_{1-3}$ alkyl optionally-substituted with 1 to 3 the same or different halogen atoms, or $C_{1-3}$ alkoxy optionally-substituted with 1 to 3 the same or different halogen atoms,
$R^6$ is hydrogen, halogen, $C_{1-3}$ alkyl optionally-substituted with 1 to 3 the same or different halogen atoms, or $C_{1-3}$ alkoxy optionally-substituted with 1 to 3 the same or different halogen atoms, and
Hy is pyridine ring, pyridazine ring, pyrimidine ring, or pyrazine ring,
provided that Hy accompanied with $R^5$ and $R^6$ is not 5-chloropyridin-2-yl.

(Item 12)
The compound of any one of Items 1 to 11 or a pharmaceutically acceptable salt thereof, wherein Hy is pyridine ring.

(Item 13)
The compound of any one of Items 1 to 12 or a pharmaceutically acceptable salt thereof, wherein $R^5$ is trifluoromethyl.
(Item 14)
The compound of any one of Items 1 to 13 or a pharmaceutically acceptable salt thereof, wherein Hy is pyridin-3-yl.
(Item 15)
The compound of any one of Items 1 to 14 or a pharmaceutically acceptable salt thereof, wherein X is oxygen.
(Item 16)
The compound of any one of Items 1 to 15 or a pharmaceutically acceptable salt thereof, wherein $R^4$ is methyl.
(Item 17)
The compound of any one of Items 1 to 14 or a pharmaceutically acceptable salt thereof, wherein X is NH or NMe.
(Item 18)
The compound of any one of Items 1 to 14 or a pharmaceutically acceptable salt thereof, wherein X is NMe.
(Item 19)
The compound of Item 1 or a pharmaceutically acceptable salt thereof, selected from the following compounds:
  (3-methyloxetan-3-yl){4-[6-(trifluoromethyl)pyridin-3-yl]piperidin-1-yl}methanone (Example 1),
  (3-methyloxetan-3-yl){4-[5-(trifluoromethyl)pyridin-3-yl]piperidin-1-yl}methanone (Example 2),
  (3-methyloxetan-3-yl){4-[4-(trifluoromethyl)pyridin-3-yl]piperidin-1-yl}methanone (Example 3),
  (3-methyloxetan-3-yl){4-[2-(trifluoromethyl)pyridin-3-yl]piperidin-1-yl}methanone (Example 4),
  {4-[5-fluoro-6-(trifluoromethyl)pyridin-3-yl]piperidin-1-yl}(3-methyloxetan-3-yl)methanone (Example 29),
  (3-methyloxetan-3-yl){4-[4-methyl-6-(trifluoromethyl)pyridin-3-yl]piperidin-1-yl}methanone (Example 31),
  (1,3-dimethylazetidin-3-yl){4-[6-(trifluoromethyl)pyridin-3-yl]piperidin-1-yl}methanone (Example 41),
  (1,3-dimethylazetidin-3-yl){4-[2-(trifluoromethyl)pyridin-3-yl]piperidin-1-yl}methanone (Example 42),
  (1,3-dimethylazetidin-3-yl){4-[4-(trifluoromethyl)pyridin-3-yl]piperidin-1-yl}methanone (Example 43), and
  (1,3-dimethylazetidin-3-yl){4-[5-(trifluoromethyl)pyridin-3-yl]piperidin-1-yl}methanone (Example 44).
(Item 20)
The compound of Item 1 or a pharmaceutically acceptable salt thereof, selected from the following compounds:
  (3-methyloxetan-3-yl){4-[6-(trifluoromethyl)pyridin-3-yl]piperidin-1-yl}methanone (Example 1),
  (3-methyloxetan-3-yl){4-[5-(trifluoromethyl)pyridin-3-yl]piperidin-1-yl}methanone (Example 2),
  {4-[5-fluoro-6-(trifluoromethyl)pyridin-3-yl]piperidin-1-yl}(3-methyloxetan-3-yl)methanone (Example 29),
  (3-methyloxetan-3-yl){4-[4-methyl-6-(trifluoromethyl)pyridin-3-yl]piperidin-1-yl}methanone (Example 31),
  (1,3-dimethylazetidin-3-yl){4-[2-(trifluoromethyl)pyridin-3-yl]piperidin-1-yl}methanone (Example 42), and
  (1,3-dimethylazetidin-3-yl){4-[5-(trifluoromethyl)pyridin-3-yl]piperidin-1-yl}methanone (Example 44).
(Item 21)
A medicament comprising the compound of any one of Items 1 to 20 or a pharmaceutically acceptable salt thereof as an active ingredient.
(Item 22)
A medicament for treating or preventing central nervous system disease whose cause is related to abnormal aggregation of proteins in the brain, comprising the compound of any one of Items 1 to 20 or a pharmaceutically acceptable salt thereof.
(Item 23)
The medicament of Item 22, wherein the central nervous system disease is related to tau, α-synuclein, TDP-43, or polyglutamine.
(Item 24)
The medicament of Item 22, wherein the central nervous system disease is Alzheimer's disease, frontotemporal lobar degeneration, Parkinson's disease, dementia with Lewy body, multiple system atrophy, Gaucher disease, infantile neuroaxonal dystrophy, amyotrophic lateral sclerosis, Huntington's disease, or spinocerebellar ataxia.
(Item 25)
The medicament of Item 22, wherein the central nervous system disease is related to α-synuclein.
(Item 26)
The medicament of Item 22, wherein the central nervous system disease is Parkinson's disease, dementia with Lewy body, multiple system atrophy, Gaucher disease, or infantile neuroaxonal dystrophy.
(Item 27)
A method for treating or preventing central nervous system disease whose cause is related to abnormal aggregation of proteins in the brain, comprising administrating a therapeutically effective amount of the compound of any one of Items 1 to 20 or a pharmaceutically acceptable salt thereof to a patient in need thereof.
(Item 28)
Use of the compound of any one of Items 1 to 20 or a pharmaceutically acceptable salt thereof in the manufacture of a medicament for treating or preventing central nervous system disease whose cause is related to abnormal aggregation of proteins in the brain.
(Item 29)
The compound of any one of Items 1 to 20 or a pharmaceutically acceptable salt thereof for use in the treatment or prevention of central nervous system disease whose cause is related to abnormal aggregation of proteins in the brain.
(Item 30)
A medicament for treating or preventing central nervous system disease whose cause is related to abnormal aggregation of proteins in the brain, comprising the compound of any one of Items 1 to 20 or a pharmaceutically acceptable salt thereof in combination with at least one agent selected from L-dopa, a dopamine agonist, an MAO-B inhibitor, a catechol-O-methyltransferase (COMT) inhibitor, αSyn antibody, and a pharmaceutically acceptable salt thereof.
(Item 31)
A medicament comprising the compound of any one of Items 1 to 20 or a pharmaceutically acceptable salt thereof, for treating or preventing central nervous system disease whose cause is related to abnormal aggregation of proteins in the brain, in combination with at least one agent selected from L-dopa, a dopamine agonist, an MAO-B inhibitor, a catechol-O-methyltransferase (COMT) inhibitor, αSyn antibody, and a pharmaceutically acceptable salt thereof.
(Item 32)
A medicament for treating or preventing central nervous system disease whose cause is related to abnormal aggregation of proteins in the brain, comprising as an active ingredient a compound of formula (1):

(1)

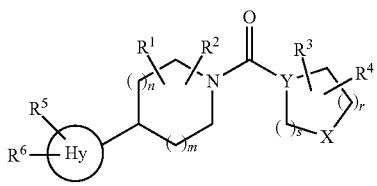

wherein
- X is oxygen or $NR^7$,
- $R^7$ is hydrogen, $C_{1-3}$ alkyl optionally-substituted with 1 to 3 the same or different halogen atoms, or cyclopropyl,
- Y is CH or nitrogen,
- m is 0, 1, or 2,
- n is 0 or 1,
- r is 0, 1, 2, 3, or 4,
- s is 0, 1, or 2,
- provided that when s is 0, then Y is CH, and r is 1, 2, 3, or 4,
- when s is 1, then Y is CH, and r is 0, 1, 2, or 3, and
- when s is 2, then r is 1 or 2,
- $R^1$ is hydrogen, halogen, methyl, or hydroxy,
- $R^2$ is hydrogen, halogen, methyl, or hydroxy,
- $R^3$ is hydrogen, or $C_{1-3}$ alkyl,
- $R^4$ is hydrogen, or $C_{1-3}$ alkyl,
- or, $R^3$ and $R^4$ may be optionally taken together to form a bridged methylene or a bridged ethylene,
- $R^5$ is hydrogen, halogen, $C_{1-3}$ alkyl optionally-substituted with 1 to 3 the same or different halogen atoms, or $C_{1-3}$ alkoxy optionally-substituted with 1 to 3 the same or different halogen atoms,
- $R^6$ is hydrogen, halogen, $C_{1-3}$ alkyl optionally-substituted with 1 to 3 the same or different halogen atoms, or $C_{1-3}$ alkoxy optionally-substituted with 1 to 3 the same or different halogen atoms, and
- Hy is pyridine ring, pyridazine ring, pyrimidine ring, or pyrazine ring, or a pharmaceutically acceptable salt thereof.

(Item 33)
The medicament of Item 32, wherein m is 1, and n is 1.
(Item 34)
The medicament of Item 32 or 33, wherein $R^1$ and $R^2$ are independently hydrogen, methyl, or fluorine.
(Item 35)
The medicament of Item 32 or 33, wherein $R^1$ and $R^2$ are hydrogen.
(Item 36)
The medicament of any one of Items 32 to 35, wherein X is oxygen, NH, or NMe.
(Item 37)
The medicament of any one of Items 32 to 36, wherein $R^3$ is hydrogen.
(Item 38)
The medicament of any one of Items 32 to 37, wherein $R^4$ is methyl or ethyl.
(Item 39)
The medicament of any one of Items 32 to 38, wherein Y is CH.
(Item 40)
The medicament of any one of Items 32 to 39, wherein s is 1.
(Item 41)
The medicament of any one of Items 32 to 40, wherein r is 0, and s is 1.

(Item 42)
The medicament of Item 32, wherein the compound is presented in formula (2):

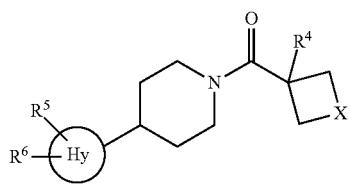

(2)

wherein
- X is oxygen, NH, or NMe,
- $R^4$ is methyl or ethyl,
- $R^5$ is hydrogen, halogen, $C_{1-3}$ alkyl optionally-substituted with 1 to 3 the same or different halogen atoms, or $C_{1-3}$ alkoxy optionally-substituted with 1 to 3 the same or different halogen atoms,
- $R^6$ is hydrogen, halogen, $C_{1-3}$ alkyl optionally-substituted with 1 to 3 the same or different halogen atoms, or $C_{1-3}$ alkoxy optionally-substituted with 1 to 3 the same or different halogen atoms, and
- Hy is pyridine ring, pyridazine ring, pyrimidine ring, or pyrazine ring.

(Item 43)
The medicament of any one of Items 32 to 42, wherein Hy is pyridine ring.
(Item 44)
The medicament of any one of Items 32 to 43, wherein $R^5$ is trifluoromethyl.
(Item 45)
The medicament of any one of Items 32 to 44, wherein Hy is pyridin-3-yl.
(Item 46)
The medicament of any one of Items 32 to 45, wherein X is oxygen.
(Item 47)
The medicament of any one of Items 32 to 46, wherein $R^4$ is methyl.
(Item 48)
The medicament of any one of Items 32 to 45, wherein X is NH or NMe.
(Item 49)
The medicament of any one of Items 32 to 45, wherein X is NMe.
(Item 50)
The medicament of any one of Items 32 to 49, wherein the central nervous system disease is related to tau, α-synuclein, TDP-43, or polyglutamine.
(Item 51)
The medicament of any one of Items 32 to 49, wherein the central nervous system disease is Alzheimer's disease, frontotemporal lobar degeneration, Parkinson's disease, dementia with Lewy body, multiple system atrophy, Gaucher disease, infantile neuroaxonal dystrophy, amyotrophic lateral sclerosis, Huntington's disease, or spinocerebellar ataxia.
(Item 52)
The medicament of any one of Items 32 to 49, wherein the central nervous system disease is related to α-synuclein.
(Item 53)
The medicament of any one of Items 32 to 49, wherein the central nervous system disease is Parkinson's disease, dementia with Lewy body, multiple system atrophy, Gaucher disease, or infantile neuroaxonal dystrophy.
(Item 54)
A method for treating or preventing central nervous system disease whose cause is related to abnormal aggregation of proteins in the brain, comprising administrating a therapeutically effective amount of the compound of any one of Items 32 to 49 or a pharmaceutically acceptable salt thereof to a patient in need thereof.
(Item 55)
Use of the compound of any one of Items 32 to 49 or a pharmaceutically acceptable salt thereof in the manufacture of a medicament for treating or preventing central nervous system disease whose cause is related to abnormal aggregation of proteins in the brain.
(Item 56)
The compound of any one of Items 32 to 49 or a pharmaceutically acceptable salt thereof for use in the treatment or prevention of central nervous system disease whose cause is related to abnormal aggregation of proteins in the brain.
(Item 57)
A medicament for treating or preventing central nervous system disease whose cause is related to abnormal aggregation of proteins in the brain, comprising the compound of any one of Items 32 to 49 or a pharmaceutically acceptable salt thereof in combination with at least one agent selected from L-dopa, a dopamine agonist, an MAO-B inhibitor, a catechol-O-methyltransferase (COMT) inhibitor, αSyn antibody, and a pharmaceutically acceptable salt thereof.
(Item 58)
A medicament comprising the compound of any one of Items 32 to 49 or a pharmaceutically acceptable salt thereof, for treating or preventing central nervous system disease whose cause is related to abnormal aggregation of proteins in the brain, in combination with at least one agent selected from L-dopa, a dopamine agonist, an MAO-B inhibitor, a catechol-O-methyltransferase (COMT) inhibitor, αSyn antibody, and a pharmaceutically acceptable salt thereof.
(Item 59)
A method for reproducing Parkinson's disease pathology with neurospheroid prepared by three-dimensional culture of genetically-mutated human iPS cells which are related to synucleinopathy, which comprises Step (I);
Step (I): Measuring the Amount of α-Synuclein Aggregate in the Neurospheroid.
(Item 60)
A method for evaluating a drug having an action suppressing/reducing the accumulation of α-synuclein aggregate in Parkinson's disease pathology with neurospheroid prepared by three-dimensional culture of genetically-mutated human iPS cells which are related to synucleinopathy, which comprises Step (I);
Step (I): Measuring the Amount of α-Synuclein Aggregate in the Neurospheroid.
(Item 61)
A process for preparing a compound of formula (3):

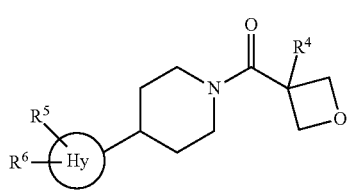

(3)

or a pharmaceutically acceptable salt thereof, wherein
R$^4$ is methyl or ethyl,
R$^5$ is trifluoromethyl,
R$^6$ is hydrogen, halogen, C$_{1-3}$ alkyl optionally-substituted with 1 to 3 the same or different halogen atoms, or C$_{1-3}$ alkoxy optionally-substituted with 1 to 3 the same or different halogen atoms, and
Hy is pyridin-3-yl, comprising the following Step 1;
(Step 1)
condensing a compound of formula (4):

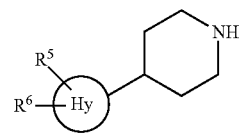

(4)

wherein R$^5$, R$^6$, and Hy are as defined above, or a salt thereof with a compound of formula (5):

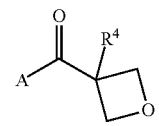

(5)

wherein R$^4$ is as defined above, and A is OH or halogen, or a salt thereof to prepare a compound of formula (3) or a pharmaceutically acceptable salt thereof.
(Item 62)
A process for preparing a compound of formula (3):

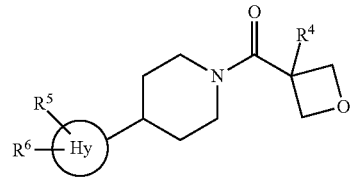

(3)

or a pharmaceutically acceptable salt thereof,
wherein
R$^4$ is methyl or ethyl,
R$^5$ is trifluoromethyl,
R$^6$ is hydrogen, halogen, C$_1$, alkyl optionally-substituted with 1 to 3 the same or different halogen atoms, or C$_{1-3}$ alkoxy optionally-substituted with 1 to 3 the same or different halogen atoms, and
Hy is pyridin-3-yl, comprising the following Step 1;
(Step 1)
condensing a compound of formula (4):

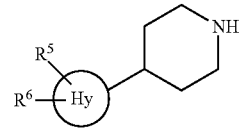

(4)

wherein R⁵, R⁶, and Hy are as defined above, or a salt thereof with a compound of formula (5):

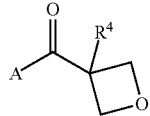                    (5)

wherein R⁴ is as defined above, and A is OH,
or a salt thereof in the presence of 2,4,6-tripropyl-1,3,5,2,4,6-trioxatriphosphorinane-2,4,6-trioxide and triethylamine to prepare a compound of formula (3) or a pharmaceutically acceptable salt thereof.

(Item 63)

A process for preparing a compound of formula (6):

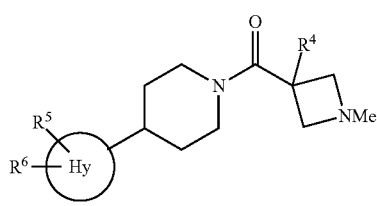                    (6)

or a pharmaceutically acceptable salt thereof,
wherein
 R⁴ is methyl,
 R⁵ is trifluoromethyl,
 R⁶ is hydrogen, halogen, $C_{1-3}$ alkyl optionally-substituted with 1 to 3 the same or different halogen atoms, or $C_{1-3}$ alkoxy optionally-substituted with 1 to 3 the same or different halogen atoms, and
 Hy is pyridin-3-yl,
comprising the following Steps 1 to 3;
(Step 1)
condensing a compound of formula (4):

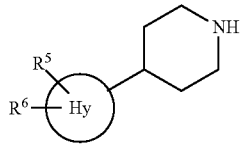                    (4)

wherein R⁵, R⁶, and Hy are as defined above, or a salt thereof with a compound of formula (7):

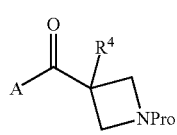                    (7)

wherein R⁴ is as defined above, A is OH or halogen, and Pro is an amino-protecting group, or a salt thereof to prepare a compound of formula (8):

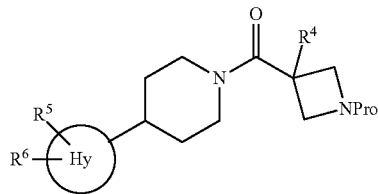                    (8)

wherein R⁴, R⁵, R⁶, Hy, and Pro are as defined above, or a pharmaceutically acceptable salt thereof,
(Step 2)
deprotecting the amino-protecting group in the compound of formula (8) or a salt thereof to prepare a compound of formula (9):

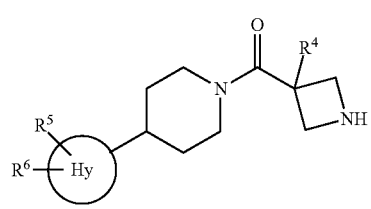                    (9)

wherein R⁴, R⁵, R⁶, and Hy are as defined above, or a salt thereof,
(Step 3)
reacting the compound of formula (9) or a salt thereof with formaldehyde or its equivalent compound in the presence of a reducing agent to prepare the compound of formula (6) or a pharmaceutically acceptable salt thereof.

(Item 64)

A process for preparing a compound of formula (6):

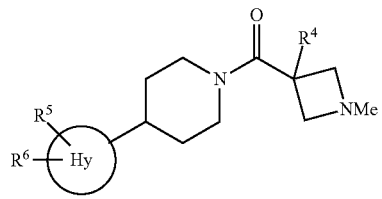                    (6)

or a pharmaceutically acceptable salt thereof,
wherein
 R⁴ is methyl,
 R⁵ is trifluoromethyl,
 R⁶ is hydrogen, halogen, $C_{1-3}$ alkyl optionally-substituted with 1 to 3 the same or different halogen atoms, or $C_{1-3}$ alkoxy optionally-substituted with 1 to 3 the same or different halogen atoms, and
 Hy is pyridin-3-yl, comprising the following Steps 1 to 3;
(Step 1)
condensing a compound of formula (4):

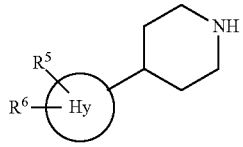

wherein R⁵, R⁶, and Hy are as defined above, or a salt thereof with a compound of formula (7):

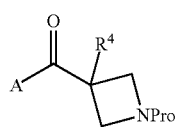

wherein R⁴ is as defined above, Pro is tert-butoxycarbonyl, and A is OH, or a salt thereof in the presence of 2,4,6-tripropyl-1,3,5,2,4,6-trioxatriphosphorinane-2,4,6-trioxide and triethylamine to prepare a compound of formula (8):

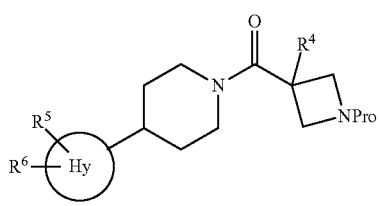

wherein R⁴, R⁵, R⁶, Hy, and Pro are as defined above, or a salt thereof,
(Step 2)
deprotecting the amino-protecting group in the compound of formula (8) or a salt thereof with trifluoroacetic acid to prepare a compound of formula (9):

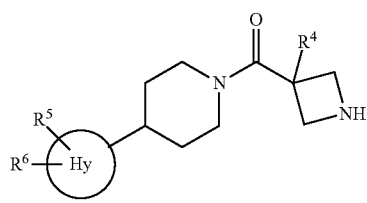

wherein R⁴, R⁵, R⁶, and Hy are as defined above, or a salt thereof,
(Step 3)
reacting the compound of formula (9) or a salt thereof with formaldehyde in the presence of triacetoxy sodium borohydride and acetic acid to prepare the compound of formula (6) or a pharmaceutically acceptable salt thereof.

Effect of the Invention

The present invention has made it possible to provide a compound of formula (1) or a pharmaceutically acceptable salt thereof. The compound or a pharmaceutically acceptable salt thereof has an action of suppressing or reducing the accumulation of abnormal aggregation of proteins in the brain, thereby it is useful as a medicament for treating or preventing central nervous system disease whose cause is related to abnormal aggregation of proteins in the brain, in particular, neurodegenerative disease related to α-synuclein such as Parkinson's disease, dementia with Lewy body, multiple system atrophy, Gaucher disease, and infantile neuroaxonal dystrophy. In addition, the present invention can reproduce spontaneous α-synuclein aggregates in neurons, which is Parkinson's disease pathology, and thereby the present invention is useful as a method for evaluating a medicament having an action of suppressing or reducing the accumulation of α-synuclein aggregates.

DESCRIPTION OF EMBODIMENTS

Figure 1:
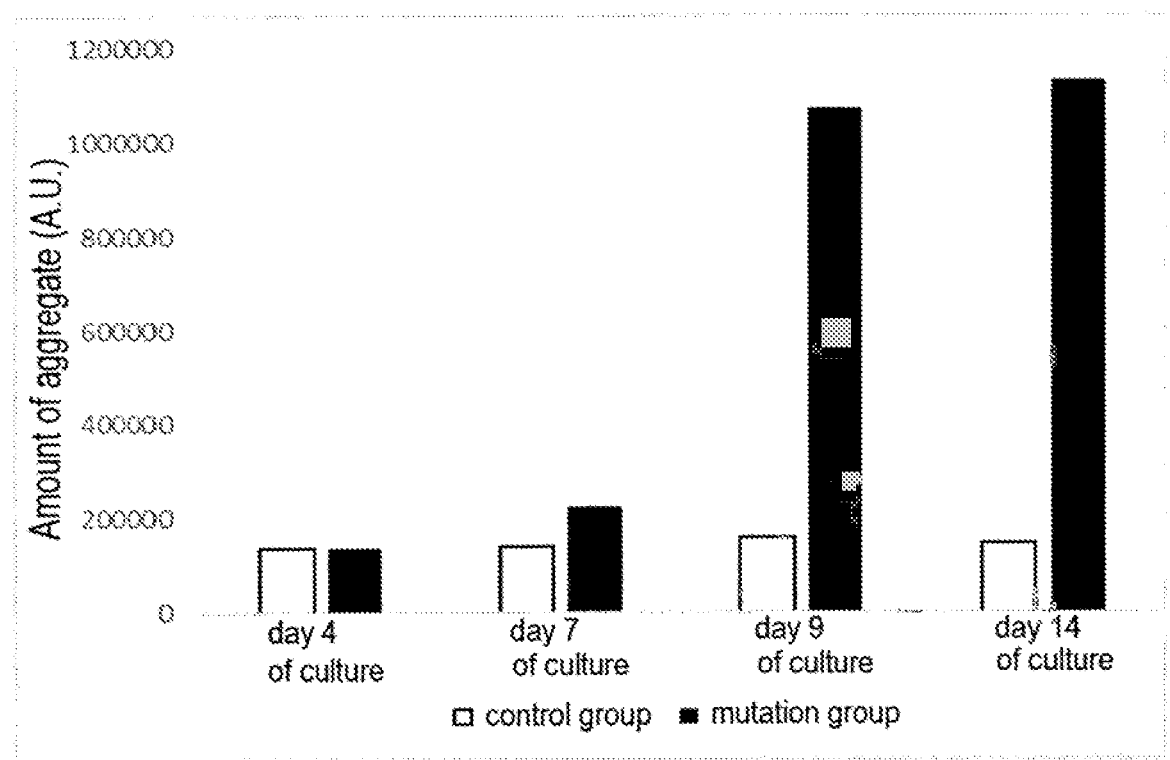
FIG. 1 shows the difference in the amount of aggregates in the neurospheroid derived from healthy human iPS cells and in the neurospheroid derived from PLA2G6 mutant iPS cells. The vertical axis indicates the amount of aggregate in neurospheroid, and the horizontal axis indicates the number of culture days. The white bars indicate the aggregate amount of in the neurospheroid derived from healthy human iPS cells, and the black bars indicate the aggregate amount of in the neurospheroid derived from PLA2G6 mutant iPS cells.

Hereinafter, the present invention is explained in detail. The present specification may denote the number of carbon atoms in definitions of "substituents" as, for example, "$C_{1-3}$". Specifically, the term "$C_{1-3}$ alkyl" is synonymous with alkyl having 1 to 3 carbon atoms.

The "halogen" includes, for example, fluorine, chlorine, bromine, and iodine. It is preferably fluorine or chlorine.

The "$C_{1-3}$ alkyl" means straight or branched chain saturated hydrocarbon group having 1 to 3 carbon atoms. The $C_{1-3}$ alkyl includes preferably "$C_{1-2}$ alkyl". The "$C_{1-3}$ alkyl" includes, for example, methyl, ethyl, propyl, and isopropyl.

The "$C_{1-3}$ alkyl" in "$C_{1-3}$ alkoxy" is as defined in the above "$C_{1-3}$ alkyl". The "$C_{1-3}$ alkoxy" includes preferably "$C_{1-2}$ alkoxy". The "$C_{1-3}$ alkoxy" includes, for example, methoxy, ethoxy, propoxy, and isopropoxy.

Preferred X, Y, m, n, r, s, $R^1$, $R^2$, $R^3$, $R^4$, $R^5$, $R^6$, and $R^7$ in the present compound of formula (1) are shown below, but the technical scope of the present invention is not limited to the scope of compounds listed below.

$R^1$, $R^2$, $R^3$, $R^4$, $R^5$, and $R^6$ groups in the compound of formula (1) may be substituted on any carbon if the carbon is substitutable; $R^1$ and $R^2$, and/or $R^3$ and $R^4$ may be substituted on the same carbon if possible; and when Y is CH, $R^3$ or $R^4$ may substitute H of the CH.

In the compound of formula (1), the bonding site (indicated by arrow below) of Hy which is bound to the nitrogen-containing saturated heterocycle is carbon.

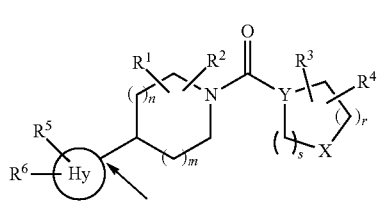

(1)

X includes preferably oxygen, NH, and NMe, more preferably oxygen and NMe.
Y includes preferably CH.
n includes preferably 1.
m includes preferably 1.
When Y is CH, r is preferably 0, 1, or 2, more preferably 0 or 1, even more preferably 0.
When Y is nitrogen, r is 1, 2, 3 or 4, preferably 1.
When Y is CH, s is preferably 0, 1 or 2, more preferably 1 or 2, even more preferably 1. When Y is nitrogen, s is 2.
$R^1$ includes preferably hydrogen, methyl, and fluorine, more preferably hydrogen.
$R^2$ includes preferably hydrogen, methyl, and fluorine, more preferably hydrogen.
$R^3$ includes preferably hydrogen, methyl, and ethyl, more preferably hydrogen.
$R^4$ includes preferably hydrogen, methyl, and ethyl, more preferably methyl, and ethyl, even more preferably methyl.

In the ring containing X and Y, when $R^3$ and $R^4$ are taken together to form a bridged methylene or a bridged ethylene, the structure of the ring containing X and Y includes structures of the following formula (3). In the following formula (3), the wavy line indicates the binding site to the carbonyl in formula (1). In the following formula (3), X and Y are as defined in Item 1.

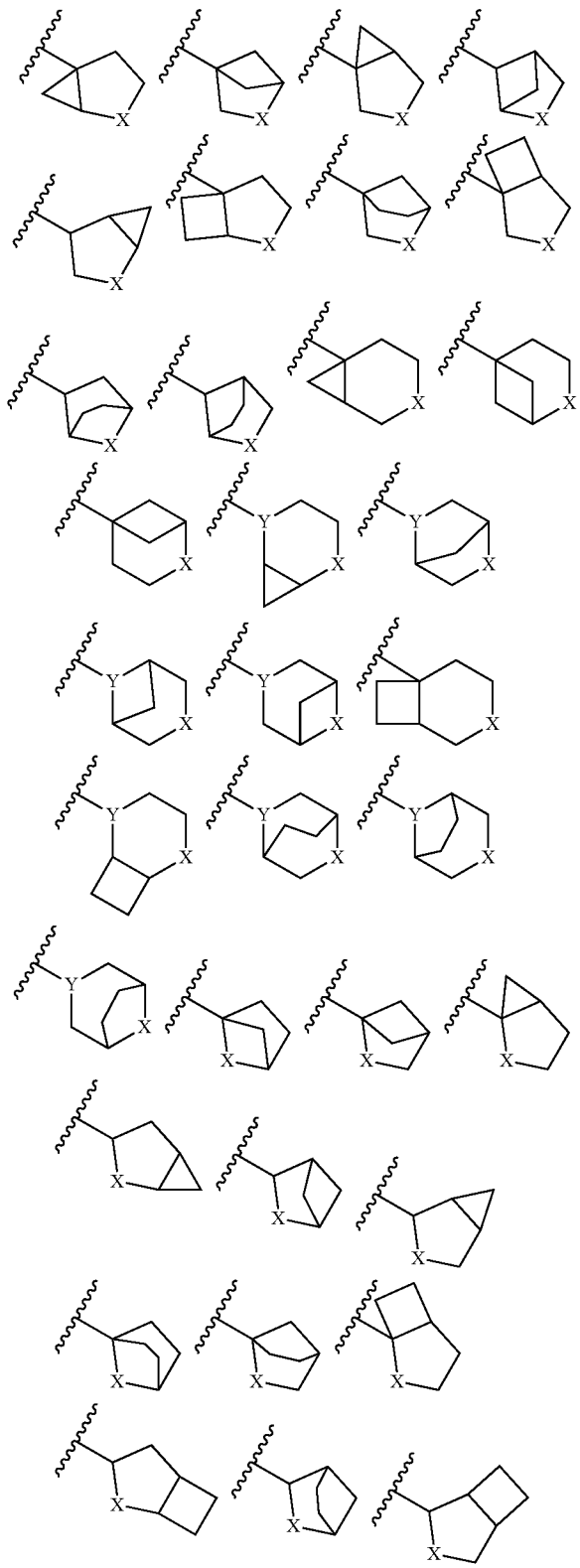

(3)

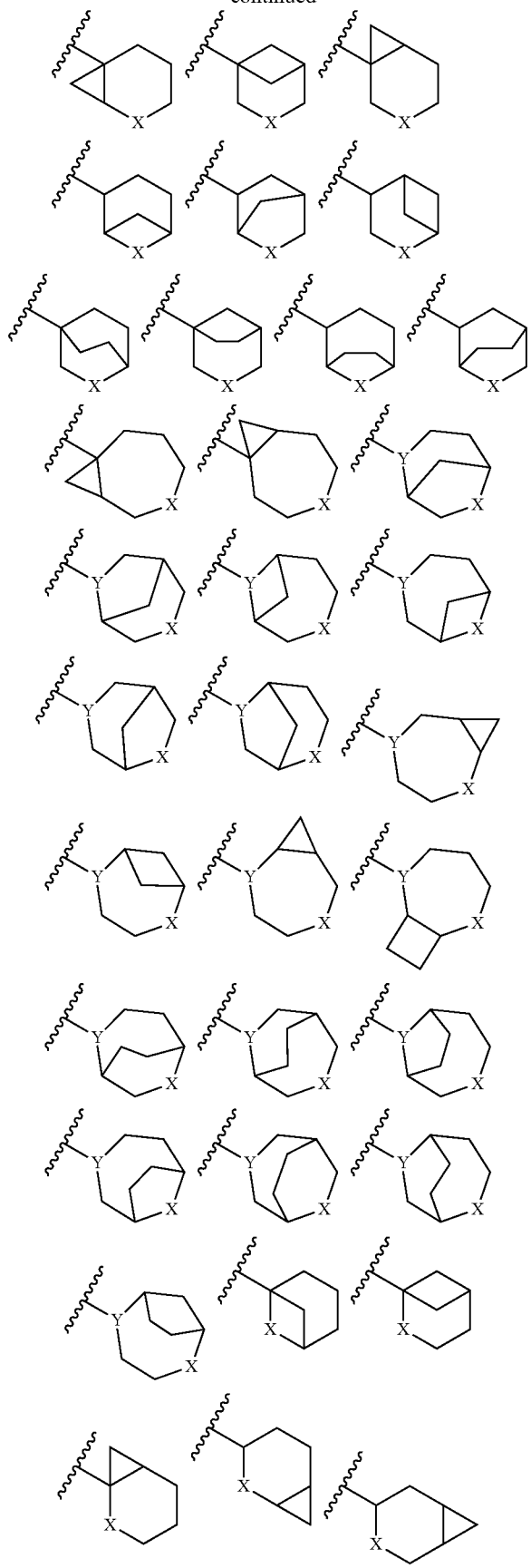
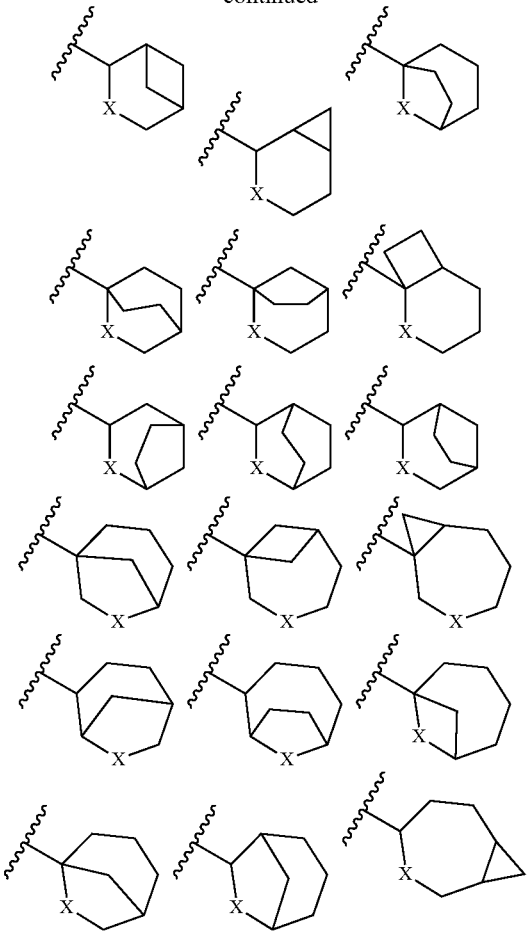

$R^5$ includes preferably halogen, and $C_{1-3}$ alkyl optionally-substituted with 1 to 3 the same or different halogen atoms, more preferably halogen, and methyl optionally-substituted with 1 to 3 fluorine atoms, even more preferably trifluoromethyl, methyl, and fluorine, the most preferably trifluoromethyl.

$R^6$ includes preferably hydrogen, halogen, and $C_{1-3}$ alkyl optionally-substituted with 1 to 3 the same or different halogen atoms, more preferably hydrogen, halogen, and methyl optionally-substituted with 1 to 3 fluorine atoms, even more preferably hydrogen, halogen, and methyl, the most preferably hydrogen, fluorine, and methyl.

$R^7$ includes preferably hydrogen, and $C_{1-3}$ alkyl, more preferably hydrogen, and methyl, even more preferably methyl. Another embodiment of $R^7$ includes $C_{1-3}$ alkyl having 1 to 5 deuterium atoms.

Hy includes preferably pyridine ring, more preferably pyridin-3-yl of the following formula (4), wherein the arrow represents the bonding position to the nitrogen-containing saturated ring.

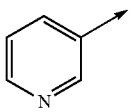

(4)

The condensing agent used for condensation reaction includes 1-ethyl-3-(3-dimethylaminopropyl)carbodiimide hydrochloride, 1-[bis(dimethylamino)methylene]-1H-1,2,3-triazolo[4,5-b]pyridinium 3-oxide hexafluorophosphate, and 2,4,6-tripropyl-1,3,5,2,4,6-trioxatriphosphorinane-2,4,6-trioxide. Preferably, it includes 1-[bis(dimethylamino)methylene]-1H-1,2,3-triazolo[4,5-b]pyridinium 3-oxide hexafluorophosphate, and 2,4,6-tripropyl-1,3,5,2,4,6-trioxatriphosphorinane-2,4,6-trioxide.

The reducing agent includes sodium borohydride, sodium triacetoxyborohydride, and sodium cyanoborohydride. Preferably, it includes sodium cyanoborohydride, and sodium triacetoxyborohydride.

The formaldehyde or its equivalent compound includes formaldehyde, 1,3,5-trioxane, and paraformaldehyde. Preferably, it includes formaldehyde.

The amino-protecting group includes tert-butoxycarbonyl group, and benzyloxycarbonyl group, preferably tert-butoxycarbonyl group.

Preferred compounds of formula (1) include the following compounds or a pharmaceutically acceptable salt thereof.

In an embodiment, the compound of formula (1) includes the following (A).

(A)

A compound or pharmaceutically acceptable salt thereof, wherein
X is oxygen or $NR^7$,
$R^7$ is hydrogen, $C_{1-3}$ alkyl, or cyclopropyl,
Y is CH or nitrogen,
m is 0, 1, or 2,
n is 0 or 1,
r is 0, 1, or 2,
s is 0, 1, or 2,
provided that when s is 0, then Y is CH, and r is 1 or 2,
when s is 1, then Y is CH, and r is 0, 1, or 2,
when s is 2, then r is 1 or 2,
$R^1$ is hydrogen, halogen, methyl, or hydroxy,
$R^2$ is hydrogen, halogen, methyl, or hydroxy,
$R^3$ is hydrogen, or $C_{1-3}$ alkyl,
$R^4$ is hydrogen, or $C_{1-3}$ alkyl,
or, $R^3$ and $R^4$ may be optionally taken together to form a bridged methylene or a bridged ethylene,
$R^5$ is halogen, or $C_{1-3}$ alkyl optionally-substituted with 1 to 3 the same or different halogen atoms,
$R^6$ is hydrogen, halogen, or $C_{1-3}$ alkyl optionally-substituted with 1 to 3 the same or different halogen atoms, and
Hy is pyridine ring, pyridazine ring, pyrimidine ring, or pyrazine ring,
provided that
(I) when Hy accompanied with $R^5$ and $R^6$ is 5-fluoropyridin-2-yl, and m and n are 1, then r is 0, and s is 1,
(II) when $R^5$ is methyl, and $R^6$ is hydrogen, then r is 0, and s is 1,
but,
(I') Hy accompanied with $R^5$ and $R^6$ is not 4,6-dimethylpyrimidin-2-yl, or 5-bromopyrimidin-2-yl,
(II') when Hy accompanied with $R^5$ and $R^6$ is 5-chloropyridin-2-yl, then m and n are 1, and both $R^1$ and $R^2$ are not hydrogen,
provided that the following compound is excluded
(III') (3-ethoxyoxetan-3-yl) [3-{4-(trifluoromethyl)pyrimidin-2-yl}pyrrolidin-1-yl]methanone.

An embodiment of the compound of formula (1) includes the following (B):

(B)

A compound or pharmaceutically acceptable salt thereof, wherein
X is oxygen or $NR^7$,
$R^2$ is hydrogen, $C_{1-3}$ alkyl, or cyclopropyl,
Y is CH or nitrogen,
m is 0, 1, or 2,
n is 0 or 1,
r is 0, 1, or 2,
s is 0, 1, or 2,
provided that when s is 0, then Y is CH, and r is 1 or 2,
when s is 1, then Y is CH, and r is 0, 1, or 2,
when s is 2, then r is 1 or 2,
$R^1$ is hydrogen, halogen, methyl, or hydroxy,
$R^2$ is hydrogen, halogen, methyl, or hydroxy,
$R^3$ is hydrogen, or $C_{1-3}$ alkyl,
$R^4$ is hydrogen, or $C_{1-3}$ alkyl,
or, $R^3$ and $R^4$ may be optionally taken together to form a bridged methylene or a bridged ethylene,
$R^5$ is halogen, or $C_{1-3}$ alkyl optionally-substituted with 1 to 3 the same or different halogen atoms,
$R^6$ is hydrogen, halogen, or $C_{1-3}$ alkyl optionally-substituted with 1 to 3 the same or different halogen atoms, and
Hy is pyridine ring,
provided that
(I) when Hy accompanied with $R^5$ and $R^6$ is 5-fluoropyridin-2-yl, and m and n are 1, then r is 0, and s is 1,
(II) when $R^5$ is methyl, and $R^6$ is hydrogen, then r is 0, and s is 1,
but,
(I') when Hy accompanied with $R^5$ and $R^6$ is 5-chloropyridin-2-yl, then m and n are 1, and both $R^1$ and $R^2$ are not hydrogen.

An embodiment of the compound of formula (1) includes the following (C):

(C)

A compound or pharmaceutically acceptable salt thereof, wherein
X is oxygen or $NR^7$,
$R^7$ is hydrogen, $C_{1-3}$ alkyl, or cyclopropyl,
Y is CH,
m is 1,
n is 1,
r is 0, 1, or 2,
s is 0, 1, or 2,
provided that when s is 0, then r is 1 or 2,
when s is 1, then r is 0, 1, or 2, and
when s is 2, then r is 1 or 2,
$R^1$ is hydrogen, methyl or fluorine,
$R^2$ is hydrogen, methyl or fluorine,
$R^3$ is hydrogen, methyl or ethyl,
$R^4$ is hydrogen, methyl or ethyl,
$R^5$ is halogen, or $C_{1-3}$ alkyl optionally-substituted with 1 to 3 the same or different halogen atoms,
$R^6$ is hydrogen, halogen, or $C_{1-3}$ alkyl optionally-substituted with 1 to 3 the same or different halogen atoms, and
Hy is pyridine ring,
provided that
(I) when Hy accompanied with $R^5$ and $R^6$ is 5-fluoropyridin-2-yl, then r is 0, and s is 1,
(II) when $R^5$ is methyl, and $R^6$ is hydrogen, then r is 0, and s is 1,
but,
(I') when Hy accompanied with $R^5$ and $R^6$ is 5-chloropyridin-2-yl, then both $R^1$ and $R^2$ are not hydrogen.

An embodiment of the compound of formula (1) includes the following (D):

(D)

A compound or pharmaceutically acceptable salt thereof, wherein
X is oxygen or NR$^7$,
R$^7$ is hydrogen or methyl,
Y is CH,
m is 1,
n is 1,
r is 0 or 1,
s is 1 or 2,
provided that when s is 2, then r is 1,
R$^1$ is hydrogen,
R$^2$ is hydrogen,
R$^3$ is hydrogen,
R$^4$ is methyl or ethyl,
R$^5$ is halogen, or methyl optionally-substituted with 1 to 3 fluorine atoms,
R$^6$ is hydrogen, halogen, or methyl optionally-substituted with 1 to 3 fluorine atoms, and
Hy is pyridin-3-yl.

An embodiment of the compound of formula (1) includes the following (E):

(E)

A compound of formula (2):

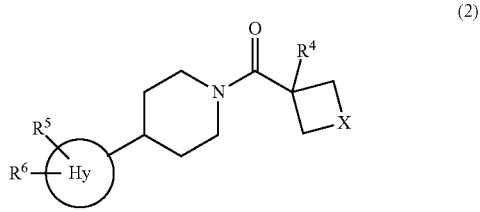

(2)

or pharmaceutically acceptable salt thereof, wherein
X is oxygen or NMe,
R$^4$ is methyl,
R$^5$ is trifluoromethyl, methyl, or fluorine,
R$^6$ is hydrogen, halogen, or methyl, and
Hy is pyridin-3-yl.

An embodiment of the compound of formula (1) includes the following compound or a pharmaceutically acceptable salt thereof:
(3-methyloxetan-3-yl){4-[6-(trifluoromethyl)pyridin-3-yl]piperidin-1-yl}methanone (Example 1),
(3-methyloxetan-3-yl){4-[5-(trifluoromethyl)pyridin-3-yl]piperidin-1-yl}methanone (Example 2),
(3-methyloxetan-3-yl){4-[4-(trifluoromethyl)pyridin-3-yl]piperidin-1-yl}methanone (Example 3),
(3-methyloxetan-3-yl){4-[2-(trifluoromethyl)pyridin-3-yl]piperidin-1-yl}methanone (Example 4),
{4-[5-fluoro-6-(trifluoromethyl)pyridin-3-yl]piperidin-1-yl}(3-methyloxetan-3-yl)methanone (Example 29),
(3-methyloxetan-3-yl){4-[4-methyl-6-(trifluoromethyl)pyridin-3-yl]piperidin-1-yl}methanone (Example 31),
(1,3-dimethylazetidin-3-yl){4-[6-(trifluoromethyl)pyridin-3-yl]piperidin-1-yl}methanone (Example 41),
(1,3-dimethylazetidin-3-yl){4-[2-(trifluoromethyl)pyridin-3-yl]piperidin-1-yl}methanone (Example 42),
(1,3-dimethylazetidin-3-yl){4-[4-(trifluoromethyl)pyridin-3-yl]piperidin-1-yl}methanone (Example 43), or
(1,3-dimethylazetidin-3-yl){4-[5-(trifluoromethyl)pyridin-3-yl]piperidin-1-yl}methanone (Example 44).

An embodiment of the compound of formula (1) includes the following compound or a pharmaceutically acceptable salt thereof:
(3-methyloxetan-3-yl){4-[6-(trifluoromethyl)pyridin-3-yl]piperidin-1-yl}methanone (Example 1),
(3-methyloxetan-3-yl){4-[5-(trifluoromethyl)pyridin-3-yl]piperidin-1-yl}methanone (Example 2),
{4-[5-fluoro-6-(trifluoromethyl)pyridin-3-yl]piperidin-1-yl}(3-methyloxetan-3-yl)methanone (Example 29),
(3-methyloxetan-3-yl){4-[4-methyl-6-(trifluoromethyl)pyridin-3-yl]piperidin-1-yl}methanone (Example 31),
(1,3-dimethylazetidin-3-yl){4-[2-(trifluoromethyl)pyridin-3-yl]piperidin-1-yl}methanone (Example 42), or
(1,3-dimethylazetidin-3-yl){4-[5-(trifluoromethyl)pyridin-3-yl]piperidin-1-yl}methanone (Example 44).

The "pharmaceutically acceptable salt" includes acid addition salts and base addition salts. For example, the acid addition salt includes inorganic acid salts such as hydrochloride, hydrobromide, sulfate, hydroiodide, nitrate, and phosphate; and organic acid salts such as citrate, oxalate, phthalate, fumarate, maleate, succinate, malate, acetate, formate, propionate, benzoate, trifluoroacetate, methanesulfonate, benzenesulfonate, para-toluenesulfonate, and camphorsulfonate. The base addition salt includes inorganic base salts such as sodium salts, potassium salts, calcium salts, magnesium salts, barium salts, and aluminum salts; and organic base salts such as trimethylamine, triethylamine, pyridine, picoline, 2,6-lutidine, ethanolamine, diethanolamine, triethanolamine, tromethamine[tris(hydroxymethyl)methylamine], tert-butylamine, cyclohexylamine, dicyclohexylamine, and N,N-dibenzylethylamine. The "pharmaceutically acceptable salt" also includes amino acid salts of basic or acidic amino acids such as arginine, lysine, ornithine, aspartate, and glutamate.

The suitable salts of starting materials and intermediates and the acceptable salts of drug substances are conventional non-toxic salts. The suitable salt includes, for example, acid addition salts such as organic acid salts (including acetate, trifluoroacetate, maleate, fumarate, citrate, tartrate, methanesulfonate, benzenesulfonate, formate, and para-toluenesulfonate) and inorganic acid salts (including hydrochloride, hydrobromide, hydroiodide, sulfate, nitrate, and phosphate); salts with amino acids (including arginine, aspartate, and glutamate); alkali metal salts (including sodium salts, and potassium salts); alkaline earth metal salts (including calcium salts, and magnesium salts); ammonium salts; organic base salts (including trimethylamine salts, triethylamine salts, pyridine salts, picolinate, dicyclohexylamine salts, and N,N'-dibenzylethylenediamine salts); and other salts which a person skilled in the art can optionally select.

If the compound of the present invention should be obtained as a salt thereof, when the present compound is obtained as a salt, it may be purified without further reaction, and when it is obtained in a free form, it may be dissolved or suspended in an appropriate organic solvent, and an acid or base may be added therein to form a salt by a common method.

In the present invention, the compound of formula (1) encompasses deuterated compounds in which any one or more 1H in the compound of formula (1) are replaced with 2H (D). The present invention encompasses compounds of formula (1) or pharmaceutically acceptable salts thereof. The compound of the present invention may exist in a form of hydrate and/or solvate with various solvents, including ethanolate, and these hydrate and/or solvate are included in the compound of the present invention. In addition, the present invention encompasses all tautomers of the compound (1), all possible stereoisomers thereof, crystalline forms thereof in various states, and mixtures thereof.

The present compound (1) encompasses optical isomers based on an optically active center, atropisomers based on axial or planar chirality caused by restriction of intramolecular rotation, and all other isomers which can exist as stereoisomers, tautomers, and geometric isomers, and mixtures thereof.

Especially, each optical isomer and atropisomer can be obtained as a racemate, or as an optically active substance when an optically active starting material or intermediate is used. Racemates of corresponding starting materials, intermediates, or final products can also be physically or chemically resolved into optical enantiomers by a known isolating method such as a method with an optically active column and a fractional crystallization method, at an appropriate step in the above preparation processes, if necessary. These methods for resolving enantiomers include a diastereomer method in which, for example, a racemate is reacted with an optically active resolving agent to synthesize two kinds of diastereomers, which are resolved by fractional crystallization or a similar method through different physical characters.

Hereinafter, the processes to prepare the compound of formula (1) in the present invention are explained showing some examples, but the processes of the present invention should not be limited thereto.

Preparation Process

The compound of the present invention may be synthesized according to each Preparation Process shown below or its combination with a known synthetic process.

Each compound in the following schemes may exist as a salt thereof, wherein the salt includes, for example, the "pharmaceutically acceptable salt" mentioned above as a salt of the compound of formula (1). The following schemes are disclosed as just examples, thus it is also possible to optionally prepare the present compound by a different process based on the knowledge of a skilled person in synthetic organic chemistry field.

In each Preparation Process described below, protecting groups can be used as necessary, even if the use of protecting groups is not explicitly stated. And, the protecting groups can be deprotected after a reaction has been completed or a series of reactions have been carried out to obtain the desired compound.

The introduction and removal of protecting groups can be carried out by a method commonly used in organic synthetic chemistry, for example, methods described in T. W. Greene and P. G. M. Wuts, "*Protective Groups in Organic Synthesis*", 3rd Ed., John Wiley and Sons, inc., New York (1999), or a method analogous thereto.

Examples of amino-protecting groups include, for example, tert-butoxycarbonyl, benzyloxycarbonyl, p-toluenesulfonyl, o-nitrobenzenesulfonyl, 4-methoxybenzyl, 2,4-dimethoxybenzyl, and the like.

Preparation Process 1

In the compound of formula (1), the compound of the following formula (1a) can be prepared, for example, by the following preparation process.

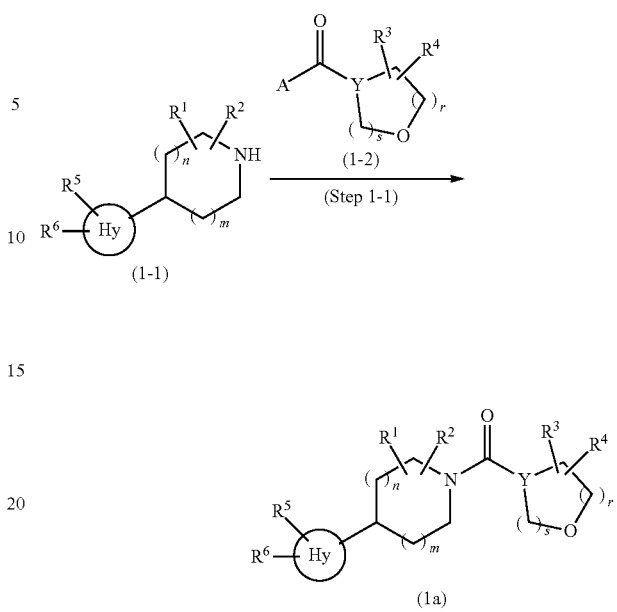

Wherein $R^1$, $R^2$, $R^3$, $R^4$, $R^5$, $R^6$, m, n, r, s, Y, and Hy are as defined in Item 1; and A is halogen or OH.

(Step 1-1: Preparation Step of Compound (1a))

Compound (1a) can be prepared by reacting Compound (1-1) and Compound (1-2) in a suitable inert solvent in the presence of any condensing agent and/or any base, or in the absence of them. As Compound (1-1), a commercial compound may be used, or a product prepared by a known method (for example, WO 2014/192868) may be used. Alternatively, the products prepared in Preparation Processes 3-6 shown below may be used as Compound (1-1). As Compound (1-2), a commercial compound may be used, or a product prepared by a known method (for example, WO2016/004272) may be used. The base used in the present step may be suitably selected from the bases exemplified below, which includes, for example, sodium hydride, triethylamine, diisopropylethylamine, and sodium carbonate. The condensing agent used in the present step may be selected from various condensing agents which are used generally in organic synthetic reaction, which includes, for example, 1-ethyl-3-(3-dimethylaminopropyl)carbodiimide hydrochloride, 1-hydroxybenzotriazole, 1-[bis(dimethylamino)methylene]-1H-1,2,3-triazolo[4,5-b]pyridinium 3-oxide hexafluorophosphate, and 2,4,6-tripropyl-1,3,5,2,4,6-trioxatriphosphorinane-2,4,6-trioxide. The solvent used in the present step may be suitably selected from the solvents exemplified below, which includes, for example, DMF, THF, dichloromethane, chloroform, and ethyl acetate. The reaction time in the present step is generally 5 minutes to 72 hours, preferably 30 minutes to 24 hours. The reaction temperature in the present step is generally −78° C. to 200° C., preferably −78° C. to 80° C.

Preparation Process 2

In the compound of formula (1), the compounds of the following formula (1b) and formula (1c) can be prepared, for example, by the following preparation process.

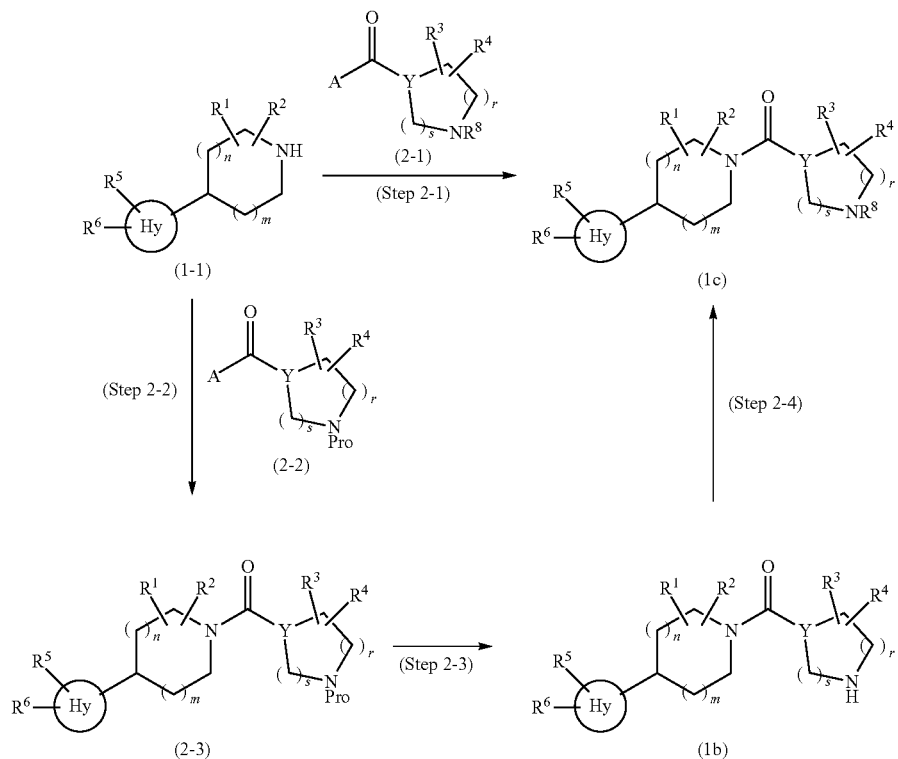

Wherein $R^1$, $R^2$, $R^3$, $R^4$, $R^5$, $R^6$, m, n, r, s, Y, and Hy are as defined in Item 1; $R^8$ is $C_{1-3}$ alkyl optionally-substituted with 1 to 3 the same or different halogen atoms, or cyclopropyl; A is halogen or OH; and Pro is an amino-protecting group.

(Step 2-1: Preparation Step of Compound (1c))

Compound (1c) can be prepared by reacting Compound (1-1) and Compound (2-1) according to the process shown in Step 1-1. As Compound (2-1), a commercial compound may be used, or a product prepared by a known method (for example, WO 2010/026096) may be used.

(Step 2-2: Preparation Step of Compound (2-3))

Compound (2-3) can be prepared by reacting Compound (1-1) and Compound (2-2) according to the process shown in Step 1-1. As Compound (2-2), a commercial compound may be used, or a product prepared by a known method (for example, WO 2008/085117) may be used.

(Step 2-3: Preparation Step of Compound (1b))

Compound (1b) can be prepared by deprotecting the amino-protecting group Pro in Compound (2-3) according to a known method (e.g. methods described in Protective Group in Organic Synthesis 3rd Ed. (described by Theodora W. Green, Peter G. M. Wuts, issued by John Wiley & Sons Inc, 1999)). Pro, an amino-protecting group, includes, for example, tert-butoxycarbonyl group, and benzyloxycarbonyl group.

(Step 2-4: Preparation Step of Compound (1c))

Compound (1c) can be prepared by reacting Compound (1b) with an aldehyde compound, a ketone compound, or a ketone equivalent compound which corresponds to $R^8$ in a suitable inert solvent in the presence of a reducing agent. The reducing agent used in the present step may be selected from various reducing agents which are used generally in organic synthetic reaction, which includes, for example, sodium borohydride, sodium triacetoxyborohydride, and sodium cyanoborohydride. The solvent used in the present step may be suitably selected from the solvents exemplified below, which includes, for example, toluene, THF, dichloromethane, and methanol. The reaction time in the present step is generally 5 minutes to 48 hours, preferably 1 hour to 24 hours. The reaction temperature in the present step is generally −78° C. to 100° C., preferably 0° C. to 80° C.

In addition, Compound (1c) can be also prepared by Compound (1b) with any alkyl halide or alkyl sulfonate which corresponds to $R^8$ in a suitable inert solvent in the presence of a base. The base used in the present step may be suitably selected from the bases exemplified below, which includes, for example, potassium carbonate, cesium carbonate, sodium hydride, and lithium diisopropylamide. The solvent used in the present step may be suitably selected from the solvents exemplified below, which includes, for example, DMF, dimethylsulfoxide, THF, and 1,4-dioxane. The reaction time in the present step is generally 5 minutes to 48 hours, preferably 1 hour to 24 hours. The reaction temperature in the present step is generally −78° C. to 100° C., preferably 0° C. to 80° C.

Preparation Process 3

The compound of the following formula (1-1) can be prepared, for example, by the following preparation process.

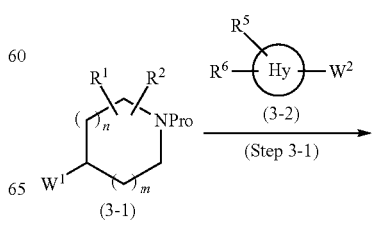

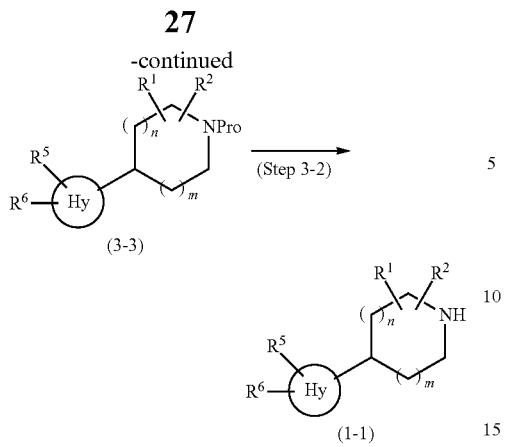

(3-3)

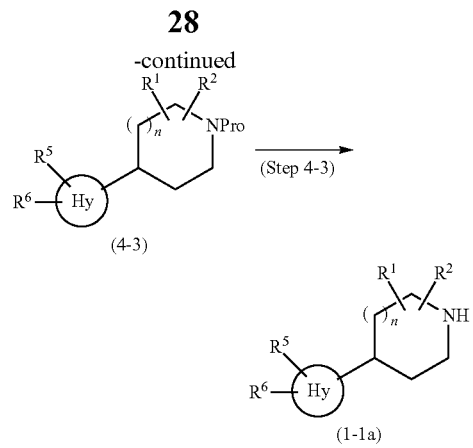

(4-3)

[structure (1-1)]

[structure (1-1a)]

Wherein $R^1$, $R^2$, $R^5$, $R^6$, m, n, and Hy are as defined in Item 1; $W^1$ and $W^2$ are halogen; and Pro is an amino-protecting group.

(Step 3-1: Preparation Step of Compound (3-3))

Compound (3-3) can be prepared by reacting Compound (3-1) and Compound (3-2) in a suitable inert solvent in the presence of zinc and palladium catalyst. As Compound (3-1), a commercial compound may be used, or a product prepared by a known method (for example, WO 2008/147831) may be used. As Compound (3-2), a commercial compound may be used, or a product prepared by a known method (for example, *Bioorganic & Medicinal Chemistry Letters* (2006), 16(17), 4528-4532) may be used. The halogen as $W^1$ and $W^2$ includes, for example chlorine, bromine, and iodine. Pro, an amino-protecting group, includes, for example, tert-butoxycarbonyl group, and benzyloxycarbonyl group. The palladium catalyst used in the present step may be selected from various palladium catalysts which are conventionally used, which includes, for example, tetrakis(triphenylphosphine)palladium(0). The solvent used in the present step may be suitably selected from the solvents exemplified below, which includes, for example, DMF, and dimethylacetamide. The reaction time in the present step is generally 5 minutes to 48 hours, preferably 1 hour to 24 hours. The reaction temperature in the present step is generally 0° C. to 100° C., preferably 0° C. to 80° C.

(Step 3-2: Preparation Step of Compound (1-1))

Compound (1-1) can be prepared from Compound (3-3) according to the process shown in Step 2-3.

Preparation Process 4

In the compound of formula (1-1), the compound of the following formula (1-1a) can be prepared, for example, by the following preparation process.

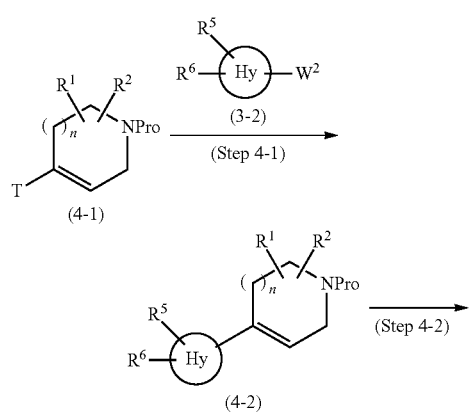

Wherein $R^1$, $R^2$, $R^5$, $R^6$, n, and Hy are as defined in Item 1; $W^2$ is halogen; Pro is an amino-protecting group; T is boronic acid or boronate ester.

(Step 4-1: Preparation Step of Compound (4-2))

Compound (4-2) can be prepared by reacting Compound (4-1) and Compound (3-2) in a suitable inert solvent in the presence of a palladium catalyst. This step can be carried out in the presence of a base and/or a phosphorus ligand as appropriate. As Compound (4-1), a commercial compound may be used, or a product prepared by a known method (for example, WO 2019/163865) may be used. Pro, an amino-protecting group, includes, for example, tert-butoxycarbonyl group, and benzyloxycarbonyl group. The palladium catalyst used in the present step may be selected from various palladium catalysts which are conventionally used, which includes, for example, tetrakis(triphenylphosphine)palladium(0). The base used in the present step may be suitably selected from the bases exemplified below, which includes, for example, potassium carbonate, and cesium carbonate. The phosphorus ligand used in the present step may be selected from various phosphorus ligands which are used generally in organic synthetic reaction, which includes, for example, triphenylphosphine and bis(diphenylphosphino) methane. The solvent used in the present step may be suitably selected from the solvents exemplified below, which includes, for example, 1,4-dioxane, tetrahydrofuran, water, and a mixture thereof. The reaction temperature in the present step is generally 0° C. to 200° C., preferably 20° C. to 150° C., and the reaction may be carried out under microwave irradiation as appropriate. The reaction time in the present step may vary depending on reaction temperature, palladium catalyst, material, and solvent to be used, etc., but it is generally 5 minutes to 72 hours, preferably 1 hour to 24 hours.

(Step 4-2: Preparation Step of Compound (4-3))

Compound (4-3) can be prepared by reacting Compound (4-2) in a suitable inert solvent in the presence of a catalyst under hydrogen atmosphere. The solvent used in the present step may be suitably selected from the solvents exemplified below, which includes, for example, methanol, ethanol, chloroform, and a mixture thereof. The catalyst used in the present step may be selected from various catalysts which are used generally in hydrogenation reaction, which includes, for example, palladium carbon and palladium hydroxide. The reaction time in the present step is generally 5 minutes to 48 hours, preferably 1 hour to 24 hours. The reaction temperature in the present step is generally 0° C. to 100° C., preferably 0° C. to 40° C.

(Step 4-3: Preparation Step of Compound (1-1a))

Compound (1-1a) can be prepared from Compound (4-3) according to the process shown in Step 2-3.

Preparation Process 5

In the compound of formula (1-1), the compound of the following formula (1-1b) can be prepared, for example, by the following preparation process.

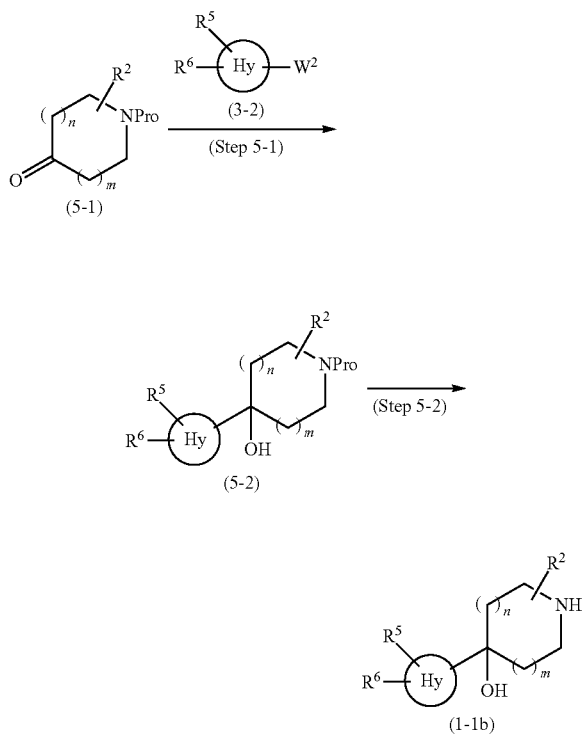

Wherein $R^2$, $R^5$, $R^6$, m, n, and Hy are as defined in Item 1; $W^2$ is halogen; and Pro is an amino-protecting group.

(Step 5-1: Preparation Step of Compound (5-2))

Compound (5-2) can be prepared by reacting Compound (3-2) and Compound (5-1) in a suitable inert solvent in the presence of an alkyllithium. As Compound (5-1), a commercial compound may be used, or a product prepared by a known method (for example, WO 2005/058888) may be used. Pro, an amino-protecting group, includes, for example, tert-butoxycarbonyl group, and benzyloxycarbonyl group. The alkyllithium used in the present step may be selected from various alkyllithiums which are conventionally used, which includes, for example, butyllithium. The solvent used in the present step may be suitably selected from the solvents exemplified below, which includes, for example, tetrahydrofuran, and diethyl ether. The reaction time in the present step is generally 5 minutes to 48 hours, preferably 1 hour to 24 hours. The reaction temperature in the present step is generally –78° C. to 100° C., preferably –78° C. to 40° C.

(Step 5-2: Preparation Step of Compound (1-1b))

Compound (1-1b) can be prepared from Compound (5-2) according to the process shown in Step 2-3.

Preparation Process 6

In the compound of formula (1-1), the compound of the following formula (1-1c) can be prepared, for example, by the following preparation process.

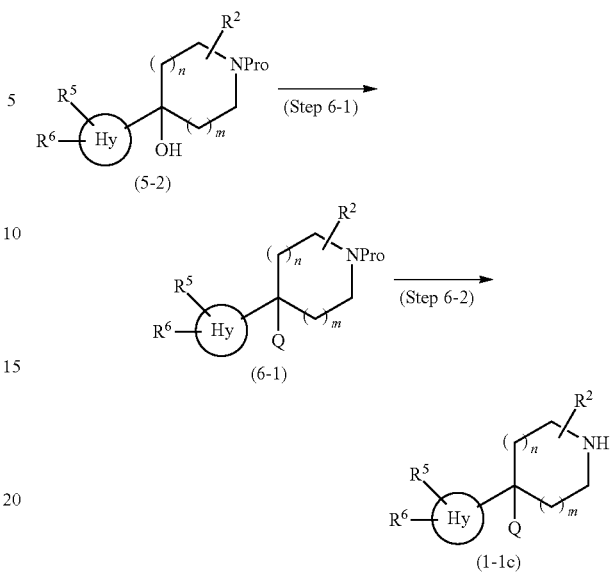

Wherein $R^2$, $R_5$, $R^6$, m, n, and Hy are as defined in Item 1; Q is halogen; and Pro is an amino-protecting group.

(Step 6-1: Preparation Step of Compound (6-1))

Compound (6-1) can be prepared by reacting Compound (5-2) in a suitable inert solvent in the presence of a halogenating agent. Pro, an amino-protecting group, includes, for example, tert-butoxycarbonyl group, and benzyloxycarbonyl group. The halogen as Q includes fluorine and chlorine. The halogenating agent used in the present step may be selected from various halogenating agents which are conventionally used, which includes, for example, (diethylamino)sulfur trifluoride, bis(2-methoxyethyl)aminosulfur trifluoride, and phosphorus oxychloride. The solvent used in the present step may be suitably selected from the solvents exemplified below, which includes, for example, dichloromethane, chloroform, 1,4-dioxane, and toluene. The reaction time in the present step is generally 5 minutes to 48 hours, preferably 1 hour to 24 hours. The reaction temperature in the present step is generally –78° C. to 100° C., preferably –78° C. to 40° C.

(Step 6-2: Preparation Step of Compound (1-1c))

Compound (1-1c) can be prepared from Compound (6-1) according to the process shown in Step 2-3.

Preparation Process 7

In the compound of formula (1), the compound of the following formula (1d) can be prepared, for example, by the following preparation process.

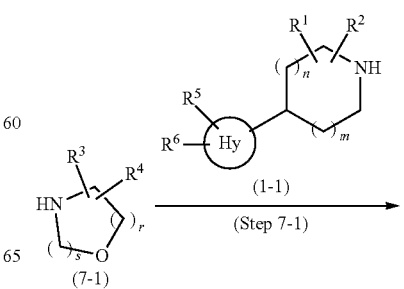

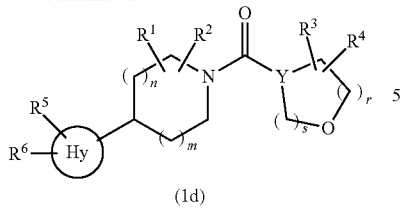

Wherein $R^1$, $R^2$, $R^3$, $R^4$, $R^5$, $R^6$, m, n, r, s, and Hy are as defined in Item 1.

(Step 7-1: Preparation Step of Compound (1d))

Compound (1d) can be prepared by reacting Compound (7-1) in a suitable inert solvent in the presence of triphosgene and a base, and then by reacting the product with Compound (1-1). The base used in the present step may be suitably selected from the bases exemplified below, which includes, for example, pyridine and triethylamine. The solvent used in the present step may be suitably selected from the solvents exemplified below, which includes, for example, dichloromethane and chloroform. The reaction time in the present step is generally 5 minutes to 48 hours, preferably 30 minutes to 24 hours. The reaction temperature in the present step is generally −78° C. to 100° C., preferably 0° C. to 80° C.

Preparation Process 8

In the compound of formula (1), the compound of the following formula (1e) can be prepared, for example, by the following preparation process.

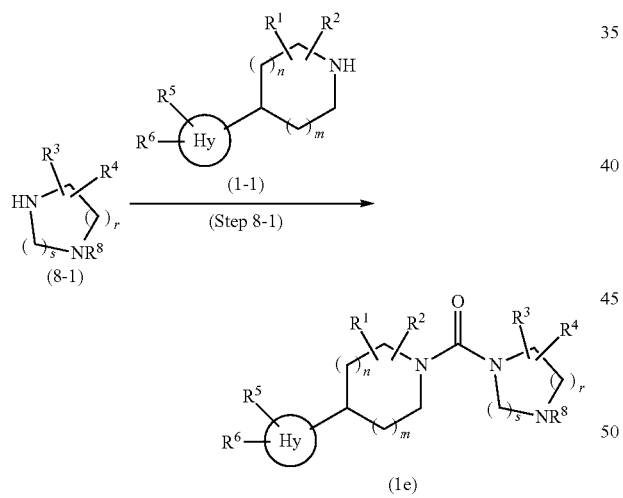

Wherein $R^1$, $R^2$, $R^3$, $R^4$, $R^5$, $R^6$, m, n, r, s, and Hy are as defined in Item 1; and $R^8$ is $C_{1-3}$ alkyl optionally-substituted with 1 to 3 the same or different halogen atoms, or cyclopropyl.

(Step 8-1: Preparation Step of Compound (1e))

Compound (1e) can be prepared by reacting Compound (8-1) and Compound (1-1) according to the process shown in Step 7-1.

Preparation Process 9

In the compound of formula (1), the compounds of the following formulae (1e) and formula (1f) can be prepared, for example, by the following preparation process.

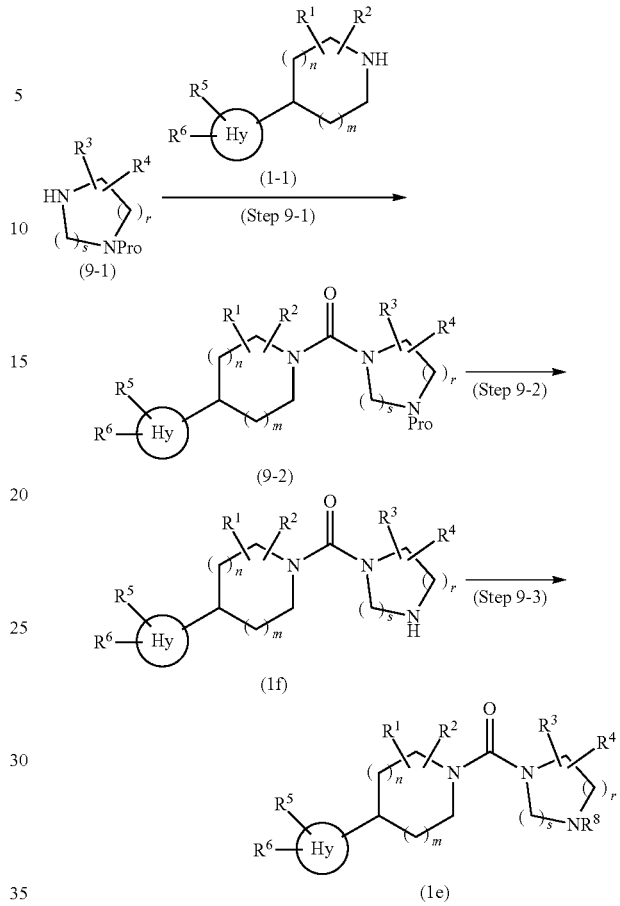

Wherein $R^1$, $R^2$, $R^3$, $R^4$, $R^5$, $R^6$, m, n, r, s, and Hy are as defined in Item 1; $R^8$ is $C_{1-3}$ alkyl optionally-substituted with 1 to 3 the same or different halogen atoms, or cyclopropyl; and Pro is an amino-protecting group.

(Step 9-1: Preparation Step of Compound (9-2))

Compound (9-2) can be prepared by reacting Compound (9-1) and Compound (1-1) according to the process shown in Step 7-1. Pro, an amino-protecting group, includes, for example, tert-butoxycarbonyl group, and benzyloxycarbonyl group.

(Step 9-2: Preparation Step of Compound (1f))

Compound (1f) can be prepared from Compound (9-2) according to the process shown in Step 2-3.

(Step 9-3: Preparation Step of Compound (1e))

Compound (1e) can be prepared from Compound (1f) according to the process shown in Step 2-4.

Among the starting materials and the intermediates in each preparation process mentioned above, the compounds that are not described in each process are commercially available or can be prepared by a skilled person with a commercially available material in a known manner or a similar manner thereto.

The base used in each step of the above processes should be suitably selected based on the reaction, the starting compound, etc., which includes, for example, alkaline bicarbonates such as sodium bicarbonate, and potassium bicarbonate; alkaline carbonate such as sodium carbonate, and potassium carbonate; metallic hydrides such as sodium hydride, and potassium hydride; alkaline metal hydroxides such as sodium hydroxide, and potassium hydroxide; alkaline metal alkoxides such as sodium methoxide, and sodium t-butoxide; organic metal bases such as butyllithium, and lithium diisopropylamide; and organic bases such as triethylamine, diisopropylethylamine, pyridine, 4-dimethylaminopyridine (DMAP), and 1,8-diazabicyclo[5.4.08]undec-7-ene (DBU).

The solvent used in each step of the above processes should be suitably selected based on the reaction, the starting compound, etc., which includes, for example, alcohol solvents such as methanol, ethanol, and isopropanol; ketone solvents such as acetone and methylketone; halogenated hydrocarbon solvents such as methylene chloride and chloroform; ether solvents such as tetrahydrofuran (THF) and dioxane; aromatic hydrocarbon solvents such as toluene and benzene; aliphatic hydrocarbon solvents such as hexane and heptane; ester solvents such as ethyl acetate and propyl acetate; amide solvents such as N,N-dimethylformamide (DMF) and N-methyl-2-pyrrolidone (NMP); sulfoxide solvents such as dimethylsulfoxide (DMSO); and nitrile solvents such as acetonitrile. The solvent used herein may be one of these solvents or a mixture of two or more solvents selected from these solvents. And, if possible in the reaction, an organic base such as diazabicycloundecene (DBU) may be used as a solvent used herein.

The present compounds of formula (1) and their intermediates can be isolated and purified in a manner known by a skilled person. It includes, for example, extraction, partition, reprecipitation, column chromatography (e.g. silica gel column chromatography, ion exchange column chromatography, and preparative liquid chromatography), and recrystallization.

The solvent for recrystallization used herein includes, for example, an alcohols solvent such as methanol, ethanol, and 2-propanol; an ether solvent such as diethyl ether; an ester solvent such as ethyl acetate; an aromatic hydrocarbon solvent such as benzene and toluene; a ketone solvent such as acetone; a halogenated solvent such as dichloromethane and chloroform; a hydrocarbon solvent such as hexane; an aprotic solvent such as dimethylformamide and acetonitrile; water; and a mixed solvent thereof. As other methods for purification, for example, methods described in Series of Experimental Chemistry (Jikken Kagaku Kouza, edited by the Chemical Society of Japan, Maruzen) Vol. 1 can be used. And, the structural determination of the present compounds can be easily done by spectroscopic analytical method such as nuclear magnetic resonance method, infrared absorption technique, and circular dichroism spectra analysis, and/or mass spectrometry, considering the structure of each starting compound.

In addition, each intermediate or each final product in the above preparation processes can be also transformed to another compound of the present invention by suitably modifying its functional group, especially extending various side-chains from amino, hydroxy, carbonyl, halogen, etc.; and optionally making the above-mentioned protection and deprotection if necessary. The modification of functional group and the extension of side-chain can be done by a conventional method (for example, see *Comprehensive Organic Transformations*, R. C. Larock, John Wiley & Sons Inc. (1999), etc.).

The present compounds of formula (1) are sometimes asymmetric compounds or sometimes have a substituent including an asymmetric carbon. In such case, the compounds have optical isomers. The present compounds include a mixture of these isomers and an isolated one, which can be prepared in a conventional manner. The compounds having an asymmetric structure can be prepared, for example, by using a starting material having an asymmetric center or by introducing an asymmetric structure anywhere along the process. For example, in case of optical isomers, optical isomers can be obtained by using an optically active starting material or resolving a mixture of optical isomers at an appropriate step. In case that the compound of formula (1) or its intermediate has a basic functional group, the optical resolution thereof includes, for example, diastereomer method, wherein the compound is transformed to a salt thereof by reacting with an optically active acid (for example, a monocarboxylic acid such as mandelic acid, N-benzyloxyalanine, and lactic acid; dicarboxylic acid such as tartaric acid, o-diisopropylidene-tartaric acid, and malic acid; or a sulfonic acid such as camphorsulfonic acid and bromocamphorsulfonic acid), in an inert solvent (for example, an alcohols such as methanol, ethanol, and 2-propanol; an ether solvent such as diethyl ether; an ester solvent such as ethyl acetate; a hydrocarbon solvent such as toluene; an aprotic solvent such as acetonitrile; or a mixed solvent thereof). In case that the compound of formula (1) or its intermediate has an acidic functional group such as carboxyl group, the compound can be also optically resolved after forming its salt with an optically active amine (for example, an organic amine such as 1-phenylethylamine, kinin, quinidine, cinchonidine, cinchonine, and strychnine).

The temperature for forming a salt is selected from the range of generally −50° C. to boiling point of a solvent used herein, preferably 0° C. to the boiling point, and more preferably room temperature to the boiling point. In order to enhance the optical purity, it is desirable to make the temperature raised to around boiling point of a solvent used herein. In collecting a precipitated crystal on a filter, an optional cooling can make the yield increased. The amount of an optically active acid or amine used herein is suitably about 0.5- about 2.0 equivalents against that of the substance compound, preferably around one equivalent. If appropriate, the obtained crystal may be recrystallized in an inert solvent (for example, an alcohol solvent such as methanol, ethanol, and 2-propanol; an ether solvent such as diethyl ether; an ester solvent such as ethyl acetate; a hydrocarbon solvent such as toluene; an aprotic solvent such as acetonitrile; or a mixed solvent thereof) to obtain its highly pure salt thereof. And, if appropriate, the optically-resolved salt can be also treated with an acid or a base to obtain its free form.

In Lewy body disease such as Parkinson's disease, abnormally aggregated α-synuclein is found in the patient's brain. Accordingly, the medicament of the present invention that suppresses or reduces the accumulation of α-synuclein aggregates is expected to exert an effect of improving the condition of these diseases.

In addition, it is believed that the aggregate exhibits neurotoxicity, induces neuronal vulnerability and neuronal cell death, and causes the onset and progression of pathology. Accordingly, the medicament of the present invention that suppresses neurotoxicity and neuronal cell death associated with α-synuclein aggregates is expected to exert an effect of improving the pathology of Lewy body disease such as Parkinson's disease.

Neurotransmitter production is one of neuronal functions, and neurotransmitter reduction indicates neural vulnerability. For example, in dopaminergic neurons, the neural vulnerability is indicated by a decrease in the amount of tyrosine hydroxylase involved in dopamine metabolism.

Furthermore, abnormalities in electroencephalograms have been reported in Lewy body diseases such as Parkinson's disease. Electroencephalograms is a manifestation of neurosynchronous activity. Accordingly, the medicament of the present invention that normalizes neuronal synchronous activity associated with α-synuclein aggregates is expected to exert an effect of improving the pathology on these diseases.

The neurospheroid used for measuring the amount of α-synuclein aggregate can be prepared, for example, by three-dimensional culture of neural stem cell prepared from human iPS cells having gene mutation related to synucleinopathy, or dopaminergic (DA) neural progenitor cell, under induction of neural differentiation. The amount of α-synuclein aggregate can be evaluated by measuring the amount of α-synuclein having high molecular weight by means of protein analysis with neurospheroid prepared by three-dimensional culture and α-synuclein antibody.

The synchronous neural firing can be evaluated by means of imaging analysis using a fluorescent calcium probe with neurospheroid prepared by three-dimensional culture.

In addition, by using the process of measuring the amount of α-synuclein aggregate and the process of measuring the synchronous neural firing in the neurospheroid, Parkinson's disease pathology can be reproduced and the drug evaluation about the action of suppressing or reducing the accumulation of α-synuclein aggregate in Parkinson's disease pathology can be performed.

The induction of differentiation from genetically-mutated human iPS cells which are related to synucleinopathy to neural stem cell can be carried out, for example, by culturing PLA2G6 gene mutant cells established from healthy human-derived iPS cell line (Clone name: 201B7, obtained from iPS Cell Research and Application, Kyoto University) in StemFitAK03N medium (Ajinomoto Co., Inc., Basic03) at 37° C. under 5% $CO_2$, and inducing the cultured product with PSC Neuronal Induction Medium (Thermo Fisher Scientific Inc., cat #A1647801).

As a culture medium for neural stem cells, for example, the following compositions can be used.
<Culture Medium Composition for Neural Stem Cells>
  Neurobasal medium (Thermo Fisher Scientific Inc., 2113049) Advanced DMEM/F-12 medium (Thermo Fisher Scientific Inc., 12634028)
  Neural Induction Supplement (Thermo Fisher Scientific Inc., A1647801)

The induction of differentiation from neural stem cells to neurospheroid can be carried out, for example, by seeding neural stem cells (10000 cells/well) in 96-well round bottom plate (Thermo Fisher Scientific Inc., cat #174929), culturing the cells in a culture medium at 37° C. under 5% $CO_2$, and replacing half of the culture on day 2 and day 4 after the induction of differentiation.

As a culture medium for neurospheroid of neural stem cells, for example, the following compositions can be used.
<Culture Medium Composition of Neurospheroid>
  BrainPhys Neuronal Medium (STEMCELL Technologies, cat #ST-05793)
  NeuroCult SM1 Neuronal Supplement (STEMCELL Technologies, cat #05711)
  N2 Supplement-A (STEMCELL Technologies, cat #07152)
  20 ng/mL BDNF (PeproTech, Inc., cat #450-02)
  20 ng/mL GDNF (PeproTech, Inc., cat #450-10)
  1 mM dibutyryl cAMP (Nacalai Tesque, Inc., cat #11540-74)
  200 nM ascorbic acid (Nacalai Tesque, Inc., cat #03420-52)

The induction of differentiation from genetically-mutated human iPS cells which are related to synucleinopathy to dopaminergic progenitor cells can be carried out, for example, by inducing dopaminergic progenitor cells from GBA1 gene homozygous mutant cells established from PLA2G6 gene mutant cells or healthy human-derived iPS cell line, with a dopaminergic neuron differentiation kit (Thermo Fisher Scientific Inc., cat #A3147701).

The induction of differentiation from dopaminergic progenitor cells to neurospheroid can be carried out, for example, by culturing cryopreserved dopaminergic progenitor cells at 37° C. under 5% $CO_2$ with Floor Plate Cell expansion kit (Thermo Fisher Scientific Inc., cat #A3165801), seeding dopaminergic progenitor cells (10000 cells/well) in a 96-well round bottom plate (Thermo Fisher Scientific Inc., cat #174929), culturing the cells in a culture medium at 37° C. under 5% $CO_2$, and replacing half of the culture every 3 or 4 days after the induction of differentiation.

As a culture medium for dopamine neurospheroid from dopaminergic progenitor cells, for example, the following compositions can be used.
<Culture Medium Composition of Dopamine Neurospheroid>
  BrainPhys Neuronal Medium (STEMCELL Technologies, cat #ST-05793)
  Dopaminergic Neuron Maturation Supplement (Thermo Fisher Scientific Inc., cat #A3147401)
  20 ng/mL BDNF (PeproTech, Inc., cat #450-02)
  20 ng/mL GDNF (PeproTech, Inc., cat #450-10)
  1 mM dibutyryl cAMP (Nacalai Tesque, Inc., cat #11540-74)
  200 nM ascorbic acid (Nacalai Tesque, Inc., cat #03420-52)

The measurement of the amount of α-synuclein aggregate in neurospheroid can be carried out, for example, by
  taking out the differentiation-induced neurospheroid from the culture medium,
  adding TBS solution (Nacalai Tesque, Inc., cat #12748-31) containing 1% TritionX-100 (Nacalai Tesque, Inc., cat #12967-32) thereto,
  extracting the protein from the mixture with an ultrasonicator, and
  subjecting the extracted protein to a protein analysis (ProteinSimple, Inc., cat #SM-W008) under non-reducing conditions with Simple Western system using an α-synuclein antibody (Thermo Fisher Scientific Inc., cat #AHB0261) to evaluate the quantitation on the waveform shown at a molecular weight of about 300 kD.

The measurement of the neural vulnerability in neurospheroid can be carried out, for example,
  transferring the differentiation-induced dopamine neurospheroid into a TBS solution (Nacalai Tesque, Inc., cat #12748-31) contiaing 1% TritionX-100 (Nacalai Tesque, Inc., cat #12967-32),
  extracting the protein from the mixture with an ultrasonicator, and
  subjecting the extracted proteins to a protein analysis with Simple Western system (Protein Simple, Inc., cat #SM-W004) using a tyrosine hydroxylase antibody (Millipore, cat #AB152) to evaluate the quantitation on the waveform shown at a molecular weight of about 60 kD.

The measurement of the neuronal cell death in neurospheroid can be carried out, for example, by
  transferring the differentiation-induced dopamine neurospheroid into a TBS solution (Nacalai Tesque, Inc., cat #12748-31) containing 1% TritionX-100 (Nacalai Tesque, Inc., cat #12967-32), extracting the protein from the mixture with an ultrasonicator, and subjecting the extracted proteins to a protein analysis under reduced conditions with Simple Western system (Protein Simple, Inc., cat #SM-W004) using cleaved caspase 3 antibody (Cell Signaling Technology, Inc., cat #9664) to evaluate the quantitation on the waveform shown at a molecular weight of about 20 kD.

Abnormal nerve activity in neurospheroid can be measured by, for example, imaging analysis using a fluorescent calcium probe on three-dimensionally cultured neurospheroid to measure synchronous nerve firing.

The synchronous nerve firing in neurospheroid can be measured by, for example, imaging analysis using a measurement medium containing a fluorescent calcium probe (Molecular Devices, Product name: FLIPR Calcium 6 Assay Bulk Kit, cat #R8191).

The measurement medium used herein includes, for example, 20 mM Hepes (Thermo Fisher Scientific Inc., cat #15630-080), and Hank's buffer solution (Thermo Fisher Scientific Inc., cat #14065-056) containing 0.1% bovine serum albumin (Sigma-Aldrich, cat #A9576).

The compound of the present invention is useful as a medicament for treating and or preventing a central nervous system disease whose cause is related to abnormal aggregation of proteins in the brain.

The central nervous system disease whose cause is related to abnormal aggregation of proteins in the brain includes a central nervous system disease associated with tau, α-synuclein, TDP-43, or polyglutamine.

The central nervous system disease associated with tau includes Alzheimer's disease, and frontotemporal lobar degeneration; the central nervous system disease associated with α-synuclein aggregate includes Parkinson's disease, dementia with Lewy body, multiple system atrophy, Gaucher disease, and infantile neuroaxonal dystrophy; the central nervous system disease associated with TDP-43 includes amyotrophic lateral sclerosis, and frontotemporal lobar degeneration; and the central nervous system disease associated with polyglutamine includes Huntington's disease, and spinocerebellar ataxia.

The compound of the present invention is useful as a medicament for treating and or preventing preferably Alzheimer's disease, frontotemporal lobar degeneration, Parkinson's disease, dementia with Lewy body, multiple system atrophy, Gaucher disease, infantile neuroaxonal dystrophy, amyotrophic lateral sclerosis, Huntington's disease, or spinocerebellar ataxia.

The compound of the present invention is useful as a medicament for treating and or preventing more preferably a disease associated with α-synuclein aggregate.

The compound of the present invention is useful as a medicament for treating and or preventing even more preferably Parkinson's disease, dementia with Lewy body, multiple system atrophy, Gaucher disease, or infantile neuroaxonal dystrophy.

In the present invention, the "prevention/preventing" means that the active ingredient of the present invention is administered to a healthy subject who does not suffer from the disease, for example, said purpose of the administration is for preventing the onset of the disease. The "treatment/treating" means that the active ingredient of the present invention is administered to a subject who is diagnosed with the disease by a physician (i.e., a patient).

The compound of the present invention and the medicament comprising it can be orally or parenterally administrated directly or as a suitable drug formulation. The formulation type includes, for example, a tablet, a capsule, a powder, a granule, a liquid, a suspension, an injection, a patch, a poultice, and the like, but it is not limited to them. The drug formulation is prepared by a common method using pharmaceutically acceptable additives.

As the additive, an excipient, a disintegrant, a binder, a fluidizer, a lubricant, a coating agent, a solubilizer, a solubilizing adjuvant, a thickener, a dispersant, a stabilizing agent, a sweetening agent, a flavor, and the like may be used, depending on purpose. The additive used herein includes, for example, lactose, mannitol, crystalline cellulose, lower-substituted hydroxypropylcellulose, corn starch, partially-pregelatinized starch, carmellose calcium, croscarmellose sodium, hydroxypropylcellulose, hydroxypropylmethylcellulose, polyvinyl alcohol, magnesium stearate, sodium stearyl fumarate, polyethylene glycol, propylene glycol, titanium oxide, talc, and the like.

The route of administration should be chosen to be the most effective route for the treatment, which includes oral administration and parenteral administration such as intravenous injection, swabbing, inhalation, and eyedrop. Preferred one is oral administration. The dosage form includes, for example, tablet and injection, and preferably tablet. The dose of the pharmaceutical composition and the frequency of administration thereof can depend on the administration route, and patient's disease, symptom, age, body weight, etc., thus it is impossible to define them flatly. In general, the present compound may be administered to an adult by about 0.0001- about 5000 mg/day, preferably about 0.001- about 1000 mg/day, more preferably about 0.1- about 500 mg, particularly preferably about 1-about 300 mg, which may be administered once a day or a few times a day, preferably once to three times a day.

The compound of the present invention and the medicament comprising it may be used together or combined with a different drug, in order to enhance the effect and/or reduce side effects. They may be used together with a medicament for treating central nervous system disease such as L-dopa, a dopamine agonist (for example, ropinirole hydrochloride, apomorphine hydrochloride hydrate, etc.), an MAO-B inhibitor (for example, selegiline hydrochloride, etc.), a catechol-O-methyltransferase (COMT) inhibitor (for example, entacapone, etc.), α-Syn antibody (for example, Prasenimab, etc.), and their pharmaceutically acceptable salts. Hereinafter, a medicament which may be used together with the compound of the present invention may be abbreviated as a "different drug (used together)".

The administration interval of the present compound, the medicament comprising it, and the different drug used together should not be limited. They may be simultaneously administered to a subject in need thereof, or may be administered with time interval. In addition, the present compound and the different drug may be mixed as a combination drug. The dose of the different drug used together may be defined suitably based on the clinically-used dose. The mixing ratio of the present compound and the different drug used together may be defined suitably depending on subject in need of the treatment, administration route, and subject's disease, symptom, combination, etc. When the subject in need of the treatment is human being, the different drug used together may be used, for example, in a dose of 0.01-100 parts by weight per one part of the present compound. In order to suppress its side effect, a different drug used together such as an antiemetic drug, a sleep-inducing drug, an anticonvulsant drug may be used.

EXAMPLES

The present invention is explained in more detail in the following by referring to Reference examples, Examples, and Tests; however, the technical scope of the present invention should not be limited thereto. In the present specification, the term "Example" or "Reference example" sometimes means a compound itself, for example, "Example 1" indicates "a compound of Example 1", "Reference example 1" indicates "a compound of Reference example 1" The compound names used in Reference examples and Examples should not be always based on IUPAC nomenclature system.

In order to simplify description, abbreviations shown below may be sometimes used in Reference examples, Examples, and Tests.

Me: methyl

Et: ethyl

Pr: normal-propyl iPr: isopropyl

DMF: N,N-dimethylformamide

THF: tetrahydrofuran

TFA: trifluoroacetic acid

HATU: 1-[bis(dimethylamino)methylene]-1H-1,2,3-triazolo[4,5-b]pyridinium 3-oxide hexafluorophosphate The symbols used in NMR are defined as follows, s: singlet, d: doublet, dd: doublet of doublet, t: triplet, td: triplet of doublet, q: quartet, m: multiplet, br: broad, brs: broad singlet, brm: broad multiplet, and J: coupling constant.

High-performance liquid chromatography mass spectrometer; the measurement conditions of LCMS are shown below, in which the observed result of mass analysis [MS (m/z)] is shown as MH+, and the retention time is shown as Rt (min). In each measured result, A or B is added as the analytical condition used for the measurement.

Analytical Condition A

Detection apparatus: MS detector: Waters ACQUITY SQ Detector HPLC: Waters ACQUITY UPLC Column: ACQUITY UPLC BEH C18 1.7 μm 2.1×30 mm Flow rate: 0.8 mL/min Column temperature: 40° C.

Wave length: 254, 220 nm

Mobile phase:
  A: 0.06% formic acid/H$_2$O
  B: 0.06% formic acid/acetonitrile

Time program:
  Step Time (min)
    1 0.0-1.3 A: B=98: 2-4: 96
    2 1.3-1.5 A: B=4:96-98: 2

Analytical Condition B

Detection apparatus: Agilent 1200 Series, Agilent 6110 Quadrupole LCMS

Column: Xbridge C18 3.5 μm 4.6×50 mm

Flow rate: 1.8 mL/min

Wave length: 254, 214 nm

Mobile phase:
  A: 10 mM aqueous ammonium hydrogen carbonate
  B: acetonitrile

Time program:
  Step Time (min)
    1 0.0-1.5 A: B=90: 10-5: 95

Column temperature: 50° C.

Reference Example 1

5-(Piperidin-4-yl)-2-(trifluoromethyl)pyridine

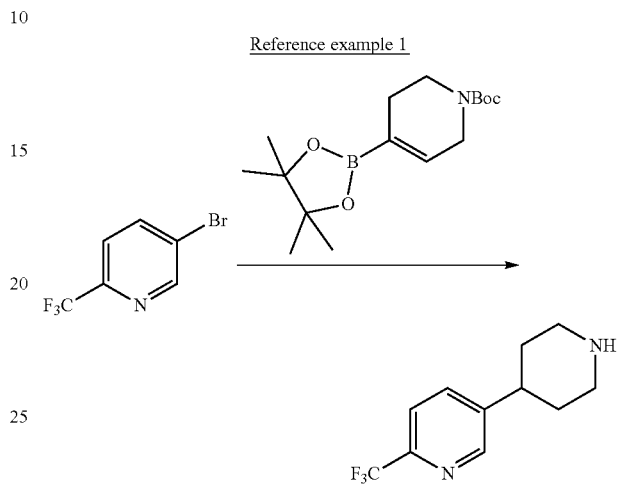

Reference example 1

To a solution of 1-(tert-butoxycarbonyl)-1,2,3,6-tetrahydro-4-(4,4,5,5-tetramethyl-1,3,2-dioxaborolan-2-yl)pyridine (6.7 g) in cyclopentyl methyl ether/water (4/1) (100 mL) were added 5-bromo-2-(trifluoromethyl)pyridine (4.1 g), 1,1'-bis(diphenylphosphino) ferrocene palladium chloride (0.66 g), and cesium carbonate (12 g), and the mixture was stirred at 100° C. for 30 minutes. The reaction solution was cooled to room temperature, and then water was added to the reaction. The mixture was extracted with ethyl acetate. The organic layer was washed with brine, and dried over magnesium sulfate. The solvent was removed out from the dried organic layer in vacuo, and the residue was roughly purified by amino silica gel chromatography (elute solvent; hexane/ethyl acetate). The obtained crude product was dissolved in methanol (50 mL), 10% palladium carbon (55% wet, 0.30 g) was added to the solution. The mixture was stirred at room temperature for 3 hours under hydrogen atmosphere. The reaction solution was filtered on Celite and washed with methanol. The solvent in the obtained filtrate was removed out in vacuo. The residue was dissolved in methanol (50 mL) again, and 10% palladium carbon (55% wet, 0.30 g) was added to the solution. The mixture was stirred at room temperature for 3 hours under hydrogen atmosphere. The reaction solution was filtered on Celite and washed with methanol. The solvent in the obtained filtrate was removed out in vacuo. The residue was dissolved in chloroform (10 mL), and trifluoroacetic acid (20 mL) was added to the solution. The solution was stirred at room temperature for one minute, and the solvent and trifluoroacetic acid were removed from the solution in vacuo. The obtained residue was purified by amino silica gel chromatography (elute solvent; hexane/ethyl acetate→ethyl acetate/ methanol) to give Reference example 1 (3.8 g). LC/MS ([M+H]+/Rt (min)): 231.2/0.50 (Analytical condition A)

Reference Examples 2-11

The compounds shown in Table 1 were prepared from each corresponding starting compound according to the process described in Reference example 1.

TABLE 1

| Reference example | Chemical structure | Instrumental analysis |
|---|---|---|
| 2 | 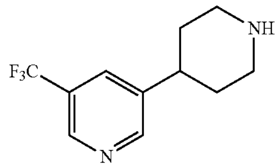 [SMILES: FC(F)(F)c1cncc(C2CCNCC2)c1] | LC/MS ([M + H]+/Rt (min)): 231.1/1.24 (Analytical condition B) |
| 3 | 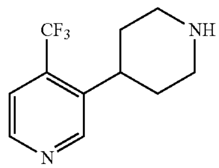 [SMILES: FC(F)(F)c1ccncc1C1CCNCC1] | LC/MS ([M + H]+/Rt (min)): 231.1/1.26 (Analytical condition B) |
| 4 | 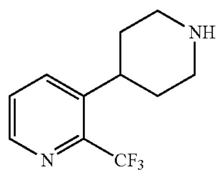 | LC/MS ([M + H]+/Rt (min)): 231.1/1.26 (Analytical condition B) |
| 5 | 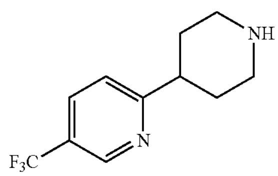 [SMILES: FC(F)(F)c1ccc(C2CCNCC2)nc1] | LC/MS ([M + H]+/Rt (min)): 231.1/1.36 (Analytical condition B) |
| 6 | 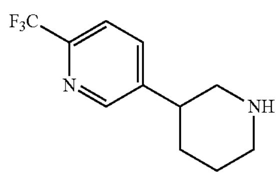 [SMILES: FC(F)(F)c1ccc(C2CCCNC2)cn1] | LC/MS ([M + H]+/Rt (min)): 231.3/1.62 (Analytical condition B) |
| 7 | 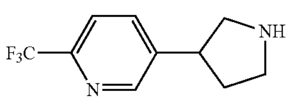 [SMILES: FC(F)(F)c1ccc(C2CCNC2)cn1] | LC/MS ([M + H]+/Rt (min)): 217.1/1.10 (Analytical condition B) |
| 8 | 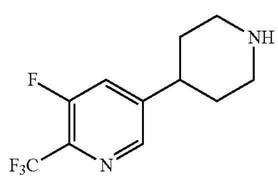 | LC/MS ([M + H]+/Rt (min)): 249.1/0.52 (Analytical condition A) |
| 9 | 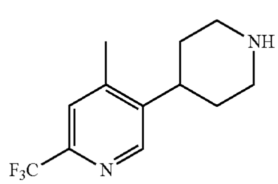 [SMILES: Cc1cc(C(F)(F)F)ncc1C1CCNCC1] | LC/MS ([M + H]+/Rt (min)): 245.1/0.58 (Analytical condition A) |
| 10 | 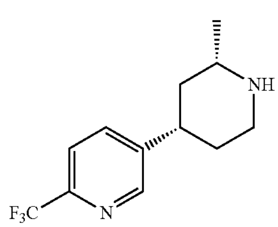 [SMILES: C[C@H]1C[C@@H](c2ccc(C(F)(F)F)nc2)CCN1] | LC/MS ([M + H]+/Rt (min)): 245.2/0.61 (Analytical condition A) |
| 11 | | LC/MS ([M + H]+/Rt (min)): 245.2/0.59 (Analytical condition A) |

Reference Example 12

5-(Azetidin-3-yl)-2-(trifluoromethyl)pyridine

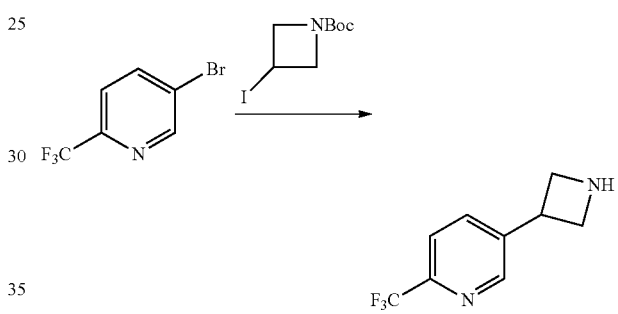

Reference example 12

Zinc powder (0.33 g) was added into a dried Schlenk tube, and the tube was purged with nitrogen. DMF (1.0 mL) and iodine (51 mg) were added to the tube under nitrogen atmosphere, and the mixture was stirred at room temperature for 5 minutes. To the activated zinc solution was added a solution of tert-butyl 3-iodoazetidine-1-carboxylate (0.19 mL) in DMF (1.0 mL), and the mixture was stirred at 40° C. for one hour. To the prepared solution of zinc alkyl was added a solution of 5-bromo-2-(trifluoromethyl)pyridine (0.23 g) and tetrakis(triphenylphosphine)palladium(0) (58 mg) in DMF (1.0 mL), and the mixture was stirred at 80° C. for 2 hours. The reaction solution was cooled to 0° C., and the reaction was quenched by slowly adding dropwise aqueous saturated ammonium chloride to the reaction solution. The resulting precipitate was removed out by suction filtration and washed with ethyl acetate. The filtrate was extracted with ethyl acetate, and the obtained organic layer was washed with brine and dried over magnesium sulfate. The solvent in the organic layer was removed out in vacuo, and then the obtained crude product was refluxed together with chloroform (1.0 mL) and trifluoroacetic acid (3.0 mL) for 20 minutes. The refluxed solution was cooled to room temperature, and the solvent and trifluoroacetic acid were removed out from the solution in vacuo. The obtained residue was purified by amino silica gel chromatography (elute solvent; hexane/ethyl acetate) to give Reference example 12 (75 mg).

LC/MS ([M+H]+/Rt (min)) 203.1/0.47 (Analytical condition A)

Reference Example 13

4-[6-(Trifluoromethyl)pyridin-3-yl]piperidin-4-ol

Reference example 13

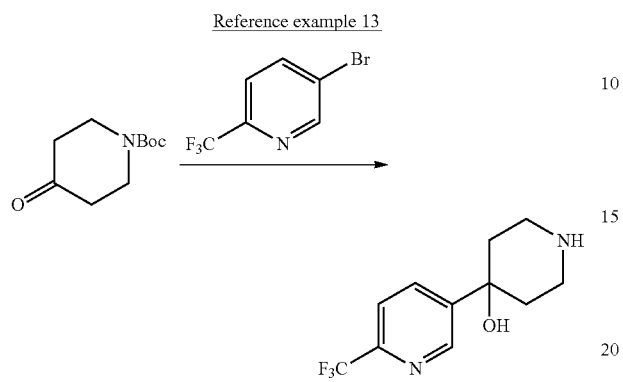

5-Bromo-2-(trifluoromethyl)pyridine (2.0 g) was added into a dried two-necked flask, and the flask was purged with nitrogen. Dry THF (20 mL) was added to the flask under nitrogen atmosphere, and the mixture was cooled to −78° C. A solution of n-butyllithium in hexane (2.6 mol/L, 5.1 mL) was added dropwise to the flask, and the mixture was stirred at −78° C. for one hour. A prepared solution of 1-Boc-4-piperidone (1.8 g) in THF (10 mL) was added dropwise to the reaction solution. After the dropping was completed, the reaction solution was warmed to room temperature. One hour later, the reaction solution was cooled to 0° C., and the reaction was quenched by slowly adding dropwise aqueous saturated ammonium chloride to the reaction solution. The reaction solution was extracted with ethyl acetate, and the obtained organic layer was washed with brine and dried over magnesium sulfate. The solvent in the organic layer was removed out in vacuo, and the obtained residue was roughly purified by amino silica gel chromatography (elute solvent; hexane/ethyl acetate 95:5-0:100). The obtained crude product was dissolved in chloroform (2.0 mL) and trifluoroacetic acid (4.0 mL), and the mixture was stirred at room temperature for 30 minutes. The solvent and trifluoroacetic acid were removed out from the solution in vacuo, and the obtained residue was purified by amino silica gel chromatography (elute solvent; hexane/ethyl acetate→ethyl acetate/methanol) to give Reference example 13 (0.23 g).

LC/MS ([M+H]$^+$/Rt (min)): 247.1/0.46 (Analytical condition A)

Reference Example 14

5-(4-Fluoropiperidin-4-yl)-2-(trifluoromethyl)pyridine

Reference example 14

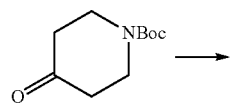

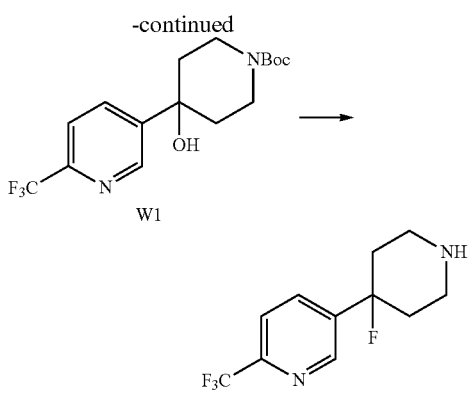

a) Preparation of tert-butyl 4-hydroxy-4-[6-(trifluoromethyl)pyridin-3-yl]piperidine-1-carboxylate (Compound W1)

5-Bromo-2-(trifluoromethyl)pyridine (2.0 g) was added into a dried two-necked flask, and the flask was purged with nitrogen. Dry THF (20 mL) was added to the flask under nitrogen atmosphere, and the mixture was cooled to −78° C. A solution of n-butyllithium in hexane (1.6 mol/L, 6.8 mL) was added dropwise to the flask, and the mixture was stirred at −78° C. for 20 minutes. A prepared solution of 1-Boc-4-piperidone (1.76 g) in THF (20 mL) was added dropwise to the reaction solution. After the dropping was completed, the reaction solution was warmed to room temperature. One hour later, the reaction solution was cooled to 0° C., and the reaction was quenched by slowly adding dropwise aqueous saturated ammonium chloride to the reaction solution. The reaction solution was extracted with ethyl acetate, and the obtained organic layer was washed with brine and dried over magnesium sulfate. The solvent in the organic layer was removed out in vacuo, and the obtained residue was purified by amino silica gel chromatography (elute solvent; hexane/ethyl acetate) to give Compound W1 (1.18 g).

LC/MS ([M+H]$^+$/Rt (min)): 347.2/0.93 (Analytical condition A)

b) Preparation of 5-(4-fluoropiperidin-4-yl)-2-(trifluoromethyl)pyridine (Reference example 14)

Compound W1 (0.12 g) was dissolved in chloroform (1.5 mL), and bis(2-methoxyethyl)aminosulfur trifluoride (0.24 mL) was added to the solution. The mixture was stirred at room temperature for 30 minutes. The reaction solution was concentrated in vacuo, and the obtained residue was roughly purified by amino silica gel chromatography (elute solvent; hexane/ethyl acetate). The obtained compound was dissolved in chloroform (0.50 mL), and reacted with TFA (1.0 mL). The reaction solution was stirred at room temperature for 5 minutes. The reaction solution was concentrated and azeotroped with toluene to remove the residued TFA. The obtained crude product was purified by amino silica gel chromatography (elute; hexane/ethyl acetate→ethyl acetate/methanol) to give Reference example 14 (18 mg).

LC/MS ([M+H]$^+$/Rt (min)): 249.1/0.60 (Analytical condition A)

Reference Examples 15-21

The compounds shown in Table 2 were prepared from each corresponding starting compound according to the process described in Reference example 1.

TABLE 2

| Reference example | Chemical structure | Instrumental analysis |
|---|---|---|
| 15 | 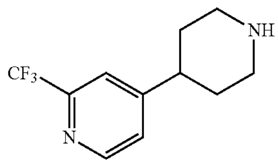 [SMILES: FC(F)(F)c1cc(C2CCNCC2)ccn1] | LC/MS ([M + H]+/Rt (min)): 231.1/1.34 (Analytical condition B) |
| 16 | 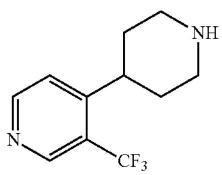 [SMILES: FC(F)(F)c1cnccc1C1CCNCC1] | LC/MS ([M + H]+/Rt (min)): 231.2/1.34 (Analytical condition B) |
| 17 | 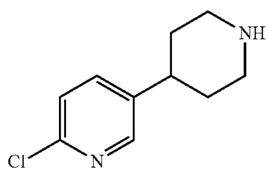 [SMILES: Clc1ccc(C2CCNCC2)cn1] | LC/MS ([M + H]+/Rt (min)): 197.1/1.14 (Analytical condition B) |
| 18 | 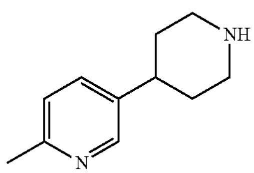 | LC/MS ([M + H]+/Rt (min)): 177.1/1.14 (Analytical condition B) |
| 19 | 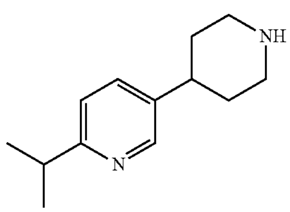 | LC/MS ([M + H]+/Rt (min)): 205.2/1.36 (Analytical condition B) |
| 20 | 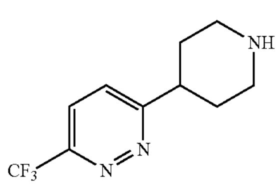 [SMILES: FC(F)(F)c1ccc(C2CCNCC2)nn1] | LC/MS ([M + H]+/Rt (min)): 232.1/1.27 (Analytical condition B) |
| 21 | 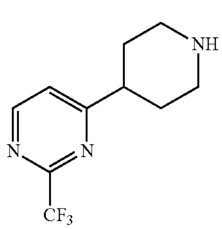 [SMILES: FC(F)(F)c1nccc(C2CCNCC2)n1] | LC/MS ([M + H]+/Rt (min)): 232.1/1.30 (Analytical condition B) |
| 22 | | LC/MS ([M + H]+/Rt (min)): 232.1/1.36 (Analytical condition B) |

Example 1

(3-Methyloxetan-3-yl){4-[6-(trifluoromethyl)pyridin-3-yl]piperidin-1-yl}methanone

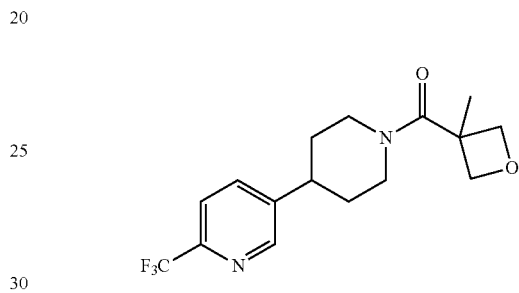

To a solution of Reference example 1 (30 mg) in chloroform (1.0 mL) were added 3-methyloxetane-3-carboxylic acid (18 mg), triethylamine (27 pL), and HATU (60 mg), and the mixture was stirred at room temperature for 30 minutes. Cesium carbonate (42 mg) was added to the reaction solution, and the reaction solution was stirred again at room temperature for 30 minutes. The reaction solution was purified by amino silica gel chromatography (elute solvent; hexane/ethyl acetate→ethyl acetate/methanol) to give Example 1 (41 mg).

LC/MS ([M+H]+/Rt (min)) 329.2/0.75 (Analytical condition A) $^1$H-NMR (400 MHz, DMSO-$d_6$) δ: 8.72 (1H, d, J=1.6 Hz), 8.02 (1H, dd, J=2.0, 8.4 Hz), 7.84 (1H, d, J=8.8 Hz), 4.83 (2H, dd, J=6.4, 8.8 Hz), 4.55-4.52 (1H, m), 4.28 (2H, t, 6.8 Hz), 3.18-3.05 (2H, m), 3.01-2.93 (1H, m), 2.67 (1H, t, J=12 Hz), 1.85-1.81 (2H, brs), 1.72-1.57 (5H, m).

Alternatively, the compound of Example 1 can be also prepared according to the following process.

To a solution of hydrochloride of Reference example 1 (100 mg) in ethyl acetate (1.0 mL) were added 3-methyloxetane-3-carboxylic acid (52 mg), triethylamine (0.17 mL), and a solution of 2,4,6-tripropyl-1,3,5,2,4,6-trioxatriphosphorinane-2,4,6-trioxide in ethyl acetate (50%, 0.40 mL), and the mixture was stirred at room temperature for one hour. The reaction solution was purified by silica gel chromatography (elute solvent; ethyl acetate/methanol) to give Example 1 (93 mg).

Examples 2-32

The compounds shown in Table 3 were prepared from each corresponding starting compound according to the process described in Example 1.

TABLE 3

| Example | Chemical structure | Instrumental analysis |
|---|---|---|
| 2 | 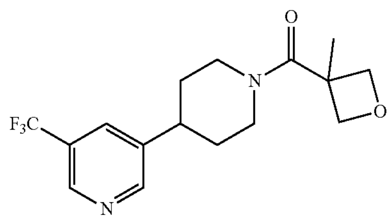 [SMILES: CC1(C(=O)N2CCC(c3cncc(C(F)(F)F)c3)CC2)COC1] | LC/MS ([M + H]⁺/Rt (min)): 329.1/1.41 (Analytical condition B) ¹H-NMR (400 MHz, DMSO-d₆) δ: 8.83 (2H, s), 8.18 (1H, s), 4.88-4.82 (2H, m), 4.56-4.53 (1H, m), 4.30-4.26 (2H, m), 3.18-3.08 (2H, m), 3.01-2.92 (1H, m), 2.68-2.62 (1H, m), 1.84-1.78 (3H, m), 1.66-1.60 (1H, m), 1.57 (3H, s). |
| 3 | 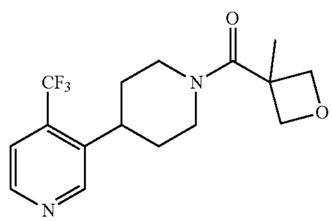 [SMILES: CC1(C(=O)N2CCC(c3cnccc3C(F)(F)F)CC2)COC1] | LC/MS ([M + H]⁺/Rt (min)): 329.2/1.39 (Analytical condition B) ¹H-NMR (500 MHz, DMSO-d₆) δ: 9.01 (1H, s), 8.70 (1H, d, J = 5.0 Hz), 7.68 (1H, d, J = 5.5 Hz), 4.88 (1H, d, J = 6.0 Hz), 4.82 (1H, d, J = 6.0 Hz), 4.57-4.55 (1H, m), 4.30-4.26 (2H, m), 3.18-3.10 (1H, m), 3.09-3.03 (2H, m), 2.68-2.63 (1H, m), 1.92-1.85 (1H, m), 1.79-1.73 (3H, m), 1.58 (3H, s). |
| 4 | 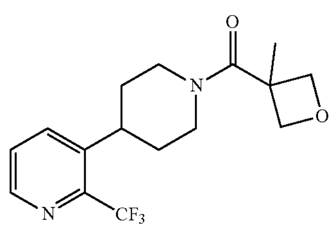 [SMILES: CC1(C(=O)N2CCC(c3cccnc3C(F)(F)F)CC2)COC1] | LC/MS ([M + H]⁺/Rt (min)): 329.1/1.38 (Analytical condition B) ¹H-NMR (500 MHz, DMSO-d₆) δ: 8.58-8.57 (1H, m), 8.23 (1H, d, J = 8.5 Hz), 7.70 (1H, m), 4.87-4.82 (2H, m), 4.57-4.54 (1H, m), 4.30-4.26 (2H, m), 3.19-3.14 (1H, m), 3.08-3.06 (2H, m), 2.69-2.64 (1H, m), 1.76-1.64 (4H, m), 1.57 (3H, s). |
| 5 | 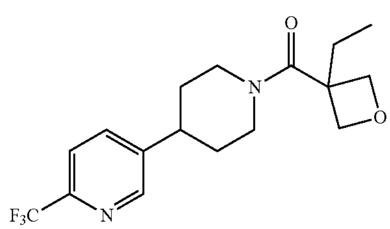 [SMILES: CCC1(C(=O)N2CCC(c3ccc(C(F)(F)F)nc3)CC2)COC1] | LC/MS ([M + H]⁺/Rt (min)): 343.2/0.80 (Analytical condition A) ¹H-NMR (400 MHz, DMSO-d₆) δ: 8.71 (1H, s), 8.00 (1H, d, J = 8.0 Hz), 7.84 (1H, d, J = 8.0 Hz), 4.80 (2H, dd, J = 12.4, 6.0 Hz), 4.57 (1H, d, J = 12.4 Hz), 4.33 (2H, t, J = 4.8 Hz), 3.16-3.10 (2H, m), 2.97 (1H, tt, J = 11.6, 2.8 Hz), 2.66 (1H, m), 1.99-1.92 (2H, m), 1.83 (2H, t, J = 12 Hz), 1.66-1.53 (2H, m), 0.89 (3H, t, J = 11.6 Hz). |
| 6 | 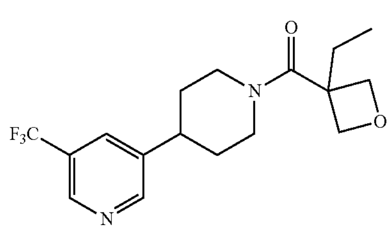 [SMILES: CCC1(C(=O)N2CCC(c3cncc(C(F)(F)F)c3)CC2)COC1] | LC/MS ([M + H]⁺/Rt (min)): 343.2/1.45 (Analytical condition B) ¹H-NMR (500 MHz, DMSO-d₆) δ: 8.81 (2H, S), 8.15 (1H, s), 4.84-4.78 (2H, m), 4.57-4.55 (1H, m), 4.35-4.31 (2H, m), 3.14-3.06 (2H, m), 3.01-2.95 (1H, m), 2.67-2.62 (1H, m), 1.97-1.92 (2H, m), 1.85-1.78 (2H, m), 1.75-1.54 (2H, m), 0.88 (3H, t, J = 7.5 Hz). |

TABLE 3-continued

| Example | Chemical structure | Instrumental analysis |
|---|---|---|
| 7 | 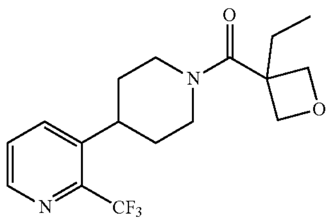 [SMILES: CCC1(C(=O)N2CCC(c3cccnc3C(F)(F)F)CC2)COC1] | LC/MS ([M + H]⁺/Rt (min)): 343.3/1.45 (Analytical condition B) $^1$H-NMR (500 MHz, DMSO-d$_6$) δ: 8.57 (1H, t, J = 3.5 Hz), 8.20 (1H, d, J = 8.0 Hz), 7.70-7.68 (1H, m), 4.85-4.78 (2H, m), 4.60-4.57 (1H, m), 4.35-4.32 (2H, m), 3.18-3.07 (3H, m), 2.69-2.64 (1H, m), 1.96-1.95 (2H, m), 1.73-1.62 (4H, m), 0.90 (3H, t, J = 7.0 Hz). |
| 8 | 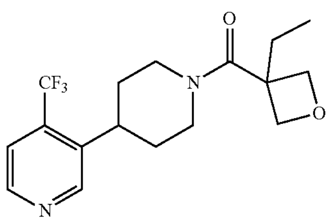 [SMILES: CCC1(C(=O)N2CCC(c3cnccc3C(F)(F)F)CC2)COC1] | LC/MS ([M + H]⁺/Rt (min)): 343.2/1.46 (Analytical condition B) $^1$H-NMR (500 MHz, DMSO-d$_6$) δ: 8.99 (1H, s), 8.70 (1H, d, J = 5.0 Hz), 7.68 (1H, d, J = 5.0 Hz), 4.86 (1H, d, J = 6.0 Hz), 4.80 (1H, d, J = 5.5 Hz), 4.60-4.57 (1H, m), 4.35-4.31 (2H, m), 3.16-3.02 (3H, m), 2.70-2.63 (1H, m), 1.96-1.94 (2H, m), 1.87-1.70 (4H, m), 0.90 (3H, t, J = 7.0 Hz). |
| 9 | 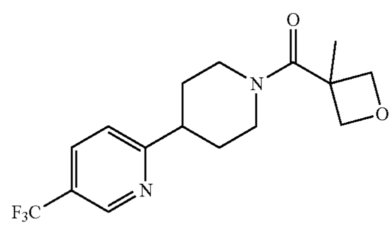 [SMILES: CC1(C(=O)N2CCC(c3ccc(C(F)(F)F)cn3)CC2)COC1] | LC/MS ([M + H]⁺/Rt (min)): 329.2/1.47 (Analytical condition B) $^1$H-NMR (500 MHz, DMSO-d$_6$) δ: 8.89 (1H, s), 8.16-8.14 (1H, m), 7.59 (1H, d, J = 8.0 Hz), 4.80 (2H, d, J = 6.5 Hz), 4.51-4.49 (1H, m), 4.28 (2H, d, J = 6.5 Hz), 3.15-3.06 (3H, m), 2.73-2.69 (1H, m), 1.91-1.89 (2H, m), 1.70-1.59 (2H, m), 1.56 (3H, s). |
| 10 | 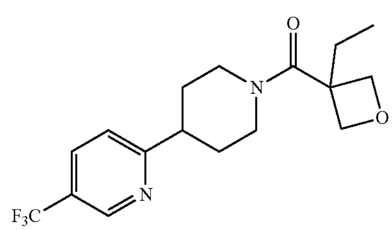 [SMILES: CCC1(C(=O)N2CCC(c3ccc(C(F)(F)F)cn3)CC2)COC1] | LC/MS ([M + H]⁺/Rt (min)): 343.1/1.53 (Analytical condition B) $^1$H-NMR (500 MHz, CDCl$_3$) δ: 8.83-8.82 (1H, m), 7.91-7.89 (1H, m), 7.31-7.30 (1H, m), 5.02-4.98 (2H, m), 4.81-4.78 (1H, m), 4.43-4.42 (2H, m), 3.16-3.13 (2H, m), 3.06-3.01 (1H, m), 2.78-2.73 (1H, m), 2.08-2.02 (4H, m), 1.80-1.71 (2H, m), 1.03 (3H, t, J = 7.5 Hz). |
| 11 | 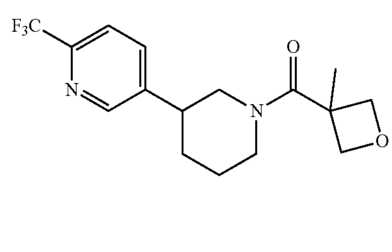 [SMILES: CC1(C(=O)N2CCCC(c3ccc(C(F)(F)F)nc3)C2)COC1] | LC/MS ([M + H]⁺/Rt (min)): 329.2/1.78 (Analytical condition B) $^1$H-NMR (500 MHz, DMSO-d$_6$) δ: 8.73 (1H, s), 8.02 (1H, d, J = 8.0 Hz), 7.87 (1H, d, J = 8.0 Hz), 4.87-4.75 (2H, m), 4.49-4.38 (1H, m), 4.29-4.21 (2H, m), 3.28-3.22 (0.5H, m), 3.10-3.01 (1H, m), 2.92-2.84 (2H, m), 2.62-2.57 (0.5H, m), 2.00-1.94 (1H, m), 1.81-1.75 (2H, m), 1.57-1.47 (4H, m). |
| 12 | 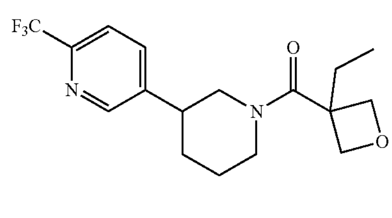 [SMILES: CCC1(C(=O)N2CCCC(c3ccc(C(F)(F)F)nc3)C2)COC1] | LC/MS ([M + H]⁺/Rt (min)): 343.3/1.85 (Analytical condition B) $^1$H-NMR (500 MHz, DMSO-d$_6$) δ: 8.74-8.73 (1H, m), 8.03-8.02 (1H, m), 7.87 (1H, d, J = 8.0 Hz), 4.85-4.76 (2H, m), 4.53-4.40 (1H, m), 4.35-4.27 (2H, m), 3.27-3.22 (0.5H, |

TABLE 3-continued

| Example | Chemical structure | Instrumental analysis |
|---|---|---|
| | | m), 3.05-3.04 (1H, m), 2.91-2.80 (2H, m), 2.63-2.57 (0.5H, m), 1.97-1.90 (3H, m), 1.78-1.74 (2H, m), 1.54-1.43 (1H, m), 0.89-0.84 (3H, m). |
| 13 | 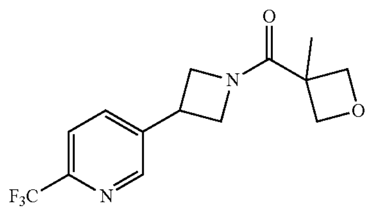 [SMILES: CC1(C(=O)N2CC(c3ccc(C(F)(F)F)nc3)C2)COC1] | LC/MS ([M + H]$^+$/Rt (min)): 301.2/0.65 (Analytical condition A) $^1$H-NMR (400 MHz, DMSO-d$_6$) δ: 8.76 (1H, s), 8.15 (1H, d, J = 8.0 Hz), 7.91 (1H, d, J = 8.0 Hz), 4.83-4.88 (2H, m), 4.47-4.33 (2H, m), 4.23-3.98 (5H, m), 1.54 (3H, s). |
| 14 | 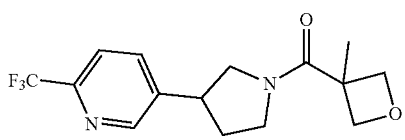 [SMILES: CC1(C(=O)N2CCC(c3ccc(C(F)(F)F)nc3)C2)COC1] | LC/MS ([M + H]$^+$/Rt (min)): 315.1/1.36 (Analytical condition B) $^1$H-NMR (500 MHz, DMSO-d$_6$) δ: 8.64 (1 H, d, J = 3.5 Hz), 7.74-7.72 (1 H, m), 7.70-7.68 (1H, m), 5.08-5.01 (2H, m), 4.36-4.28 (2H, m), 4.10-4.06 (0.5H, m), 3.87-3.83 (0.5 H, m), 3.68-3.62 (0.5H, m), 3.57-3.48 (2H, m), 3.39-3.37 (1H, m), 3.25-3.21 (0.5H, m), 2.49-2.40 (1H, m), 2.14-2.04 (1H, m), 1.70 (3H, d, J = 22.5 Hz). |
| 15 | 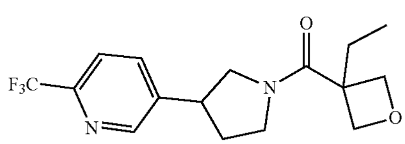 [SMILES: CCC1(C(=O)N2CCC(c3ccc(C(F)(F)F)nc3)C2)COC1] | LC/MS ([M + H]$^+$/Rt (min)): 329.2/1.42 (Analytical condition B) $^1$H-NMR (500 MHz, CDCl$_3$) δ: 8.64-8.63 (1H, m), 7.75-7.72 (1H, m), 7.70-7.68 (1H, m), 5.06-4.99 (2H, m), 4.41-4.38 (2H, m), 4.11-4.07 (0.54H, m), 3.88-3.84 (0.44H, m), 3.70-3.67 (0.44H, m), 3.61-3.48 (2H, m), 3.38-3.37 (1H, m), 3.23-3.19 (0.44H, m), 2.48-2.40 (1H, m), 2.11-2.04 (3H, m), 1.05-0.99 (3H, m). |
| 16 | 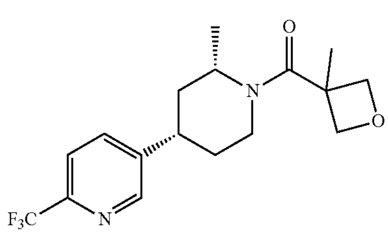 [SMILES: C[C@H]1C[C@@H](c2ccc(C(F)(F)F)nc2)CCN1C(=O)C1(C)COC1] | LC/MS ([M + H]$^+$/Rt (min)): 343.3/0.83 (Analytical condition A) $^1$H-NMR (400 MHz, CDCl$_3$) δ: 8.58 (d, 1H, J = 2.0 Hz), 7.69-7.61 (m, 2H), 5.00-4.98 (m, 2H), 4.37-4.33 (m, 3H), 3.35-3.30 (m, 1H), 2.94-2.85 (m, 2H), 2.24-2.14 (m, 1H), 2.06-2.01 (m, 1H), 1.75-1.63 (m, 2H), 1.67 (s, 3H), 1.19 (d, 3H, J = 6.0 Hz). |
| 17 | 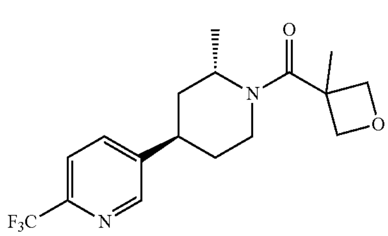 [SMILES: C[C@H]1C[C@H](c2ccc(C(F)(F)F)nc2)CCN1C(=O)C1(C)COC1] | LC/MS ([M + H]$^+$/Rt (min)): 343.3/0.84 (Analytical condition A) $^1$H-NMR (400 MHz, CDCl$_3$) δ: 8.57 (s, 1H), 7.68-7.61 (m, 2H), 5.08-4.64 (m, 3H), 4.36-4.28 (m, 2H), 3.40-3.05 (m, 2H), 2.92-2.81 (m, 1H), 1.93-1.05 (m, 7H), 1.42-1.26 (m, 3H). |

TABLE 3-continued

| Example | Chemical structure | Instrumental analysis |
|---|---|---|
| 18 | 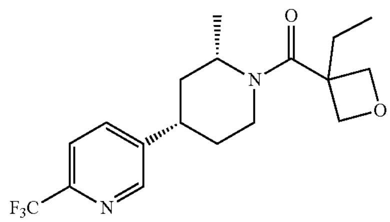 [SMILES: CCC1(C(=O)N2CC[C@H](c3ccc(C(F)(F)F)nc3)C[C@@H]2C)COC1] | LC/MS ([M + H]⁺/Rt (min)): 357.3/0.87 (Analytical condition A) $^1$H-NMR (400 MHz, CDCl$_3$) δ: 8.58 (d, 1H, J = 2.0 Hz), 7.69-7.61 (m, 2H), 4.98-4.95 (m, 2H), 4.41-4.37 (m, 3H), 3.36-3.24 (m, 1H), 2.93-2.84 (m, 2H), 2.23-2.13 (m, 1H), 2.09-1.97 (m, 3H), 1.75-1.58 (m, 2H), 1.19 (d, 3H, J = 6.8 Hz), 0.98 (t, 3H, J = 8.0 Hz). |
| 19 | 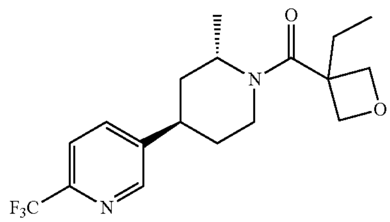 [SMILES: CCC1(C(=O)N2CC[C@@H](c3ccc(C(F)(F)F)nc3)C[C@@H]2C)COC1] | LC/MS ([M + H]⁺/Rt (min)): 357.3/0.88 (Analytical condition A) $^1$H-NMR (400 MHz, CDCl$_3$) δ: 8.57 (s, 1H), 7.68-7.61 (m, 2H), 5.10-4.68 (m, 3H), 4.42-4.32 (m, 2H), 3.41-3.05 (m, 2H), 2.92-2.85 (m, 1H), 2.04-1.47 (m, 6H), 1.43-1.26 (m, 3H), 1.02-0.95 (m, 3H). |
| 20 | 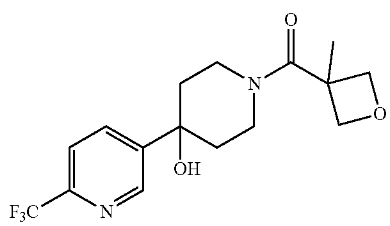 [SMILES: CC1(C(=O)N2CCC(O)(c3ccc(C(F)(F)F)nc3)CC2)COC1] | LC/MS ([M + H]⁺/Rt (min)): 345.2/0.63 (Analytical condition A) $^1$H-NMR (400 MHz, DMSO-d$_6$) δ: 8.93 (1H, s), 8.19 (1H, d, J = 8.0 Hz), 7.87 (1H, d, J = 8.0 Hz), 5.60 (1H, s), 4.85 (2H, m), 4.36 (1H, d, J = 11.2 Hz), 4.30-4.26 (2H, m), 3.42 (1H, t, J = 12.4 Hz), 2.99 (1H, t, J = 12.4 Hz), 2.92-2.86 (1H, m), 2.02-1.88 (2H, m), 1.74-1.57 (5H, m). |
| 21 | 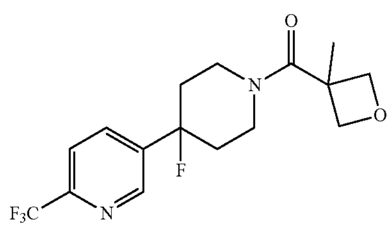 | LC/MS ([M + H]⁺/Rt (min)): 347.1/0.83 (Analytical condition A) $^1$H-NMR (400 MHz, DMSO-d$_6$) δ: 8.88 (1H, s), 8.16 (1H, d, J = 8.4 Hz), 7.92 (1H, d, J = 8.4 Hz), 4.84 (2H, dd, J = 12.4, 5.6 Hz), 4.44 (1H, dd, J = 13.6, 2.4 Hz), 4.26 (2H, dd, J = 13.2, 5.6 Hz), 3.34 (1H, m), 2.98 (1H, d, J = 11.6 Hz), 2.87 (1H, t, J = 11.6 Hz), 2.23-1.90 (4H, m), 1.55 (3H, s). |
| 22 | 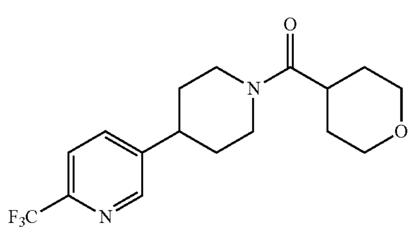 | LC/MS ([M + H]⁺/Rt (min)): 343.2/0.80 (Analytical condition A) $^1$H-NMR (400 MHz, CDCl$_3$) δ: 8.56 (d, 1H, J = 1.2 Hz), 7.67-7.60 (m, 2H), 4.84-4.80 (m, 1H), 4.10-3.98 (m, 3H), 3.46-3.40 (m, 2H), 3.20-3.13 (m, 1H), 2.91-2.59 (m, 3H), 2.00-1.84 (m, 4H), 1.66-1.55 (m, 4H). |
| 23 | 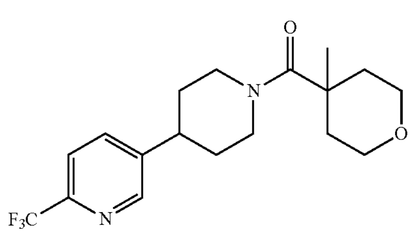 [SMILES: CC1(C(=O)N2CCC(c3ccc(C(F)(F)F)nc3)CC2)CCOCC1] | LC/MS ([M + H]⁺/Rt (min)): 357.2/0.85 (Analytical condition A) $^1$H-NMR (400 MHz, DMSO-d$_6$) δ: 8.70 (1H, d, J = 2.0 Hz), 7.99 (1H, dd, J = 8.0, 2.0 Hz), 7.83 (1H, d, J = 8.0 Hz), 4.44 (2H, d, J = 12.8 Hz), 3.67-3.61 (2H, m), 3.53-3.47 (2H, m), 3.01 (1H, tt, J = 12, 3.6 Hz), 2.89 |

TABLE 3-continued

| Example | Chemical structure | Instrumental analysis |
|---|---|---|
|  |  | (2H, t, J = 12.8 Hz), 2.01 (2H, dd, J = 12, 2.4 Hz), 1.85 (2H, dd, J = 12.8, 1.6 Hz), 1.59-1.43 (4H, m), 1.28 (3H, s). |
| 24 | 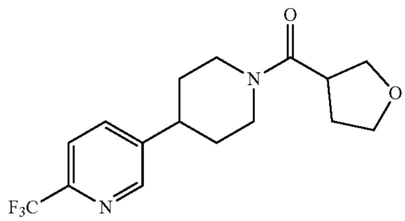 [SMILES: O=C(C1CCOC1)N1CCC(c2ccc(C(F)(F)F)nc2)CC1] | LC/MS ([M + H]⁺/Rt (min)): 329.2/0.75 (Analytical condition A) ¹H-NMR (400 MHz, CDCl₃) δ: 8.60 (1H, s), 7.69-7.64 (2H, m), 4.85 (1H, d, J = 13.2 Hz), 4.09 (1H, d, J = 13.2 Hz), 4.04 (1H, t, J = 8.0 Hz), 3.95-3.85 (3H, m), 3.32-3.17 (2H, m), 2.91 (1H, t, J = 12 Hz), 2.69 (1H, t, J = 12 Hz), 2.33-2.21 (1H, m), 2.15-2.06 (1H, m), 1.97 (2H, t, J = 14.8 Hz), 1.72-1.62 (2H, m, overlapped with H₂O). |
| 25 | 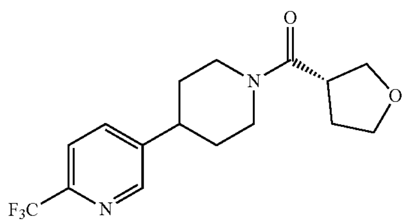 [SMILES: O=C([C@H]1CCOC1)N1CCC(c2ccc(C(F)(F)F)nc2)CC1] | LC/MS ([M + H]⁺/Rt (min)): 329.2/0.78 (Analytical condition A) ¹H-NMR (400 MHz, CDCl₃) δ: 8.58 (s, 1H), 7.67-7.61 (m, 2H), 4.85-4.82 (m, 1H), 4.09-4.00 (m, 2H), 3.93-3.82 (m, 3H), 3.30-3.15 (m, 2H), 2.92-2.86 (m, 1H), 2.70-2.64 (m, 1H), 2.32-1.91 (m, 4H), 1.69-1.53 (m, 2H). |
| 26 | 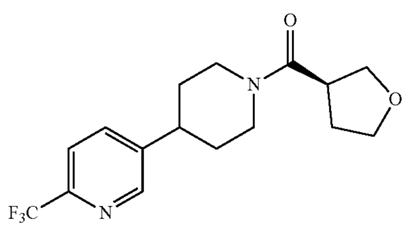 [SMILES: O=C([C@@H]1CCOC1)N1CCC(c2ccc(C(F)(F)F)nc2)CC1] | LC/MS ([M + H]⁺/Rt (min)): 329.2/0.78 (Analytical condition A) ¹H-NMR (400 MHz, CDCl₃) δ: 8.58 (s, 1H), 7.67-7.62 (m, 2H), 4.86-4.82 (m, 1H), 4.09-4.00 (m, 2H), 3.93-3.83 (m, 3H), 3.30-3.15 (m, 2H), 2.93-2.86 (m, 1H), 2.71-2.64 (m, 1H), 2.32-1.91 (m, 4H), 1.70-1.53 (m, 2H). |
| 27 | 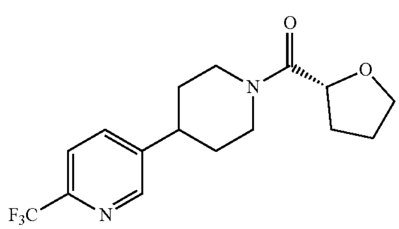 [SMILES: O=C([C@H]1CCCO1)N1CCC(c2ccc(C(F)(F)F)nc2)CC1] | LC/MS ([M + H]⁺/Rt (min)): 329.2/0.80 (Analytical condition A) ¹H-NMR (400 MHz, CDCl₃) δ: 8.58 (d, 1H, J = 2.0 Hz), 7.67-7.61 (m, 2H), 4.78 (d, 1H, J = 13.6 Hz), 4.65-4.60 (m, 1H), 4.26 (d, 1H, J = 13.6 Hz), 3.97-3.91 (m, 1H), 3.87-3.81 (m, 1H), 3.22-3.07 (m, 1H), 2.93-2.85 (m, 1H), 2.73-2.63 (m, 1H), 2.36-2.27 (m, 1H), 2.10-1.85 (m, 5H), 1.79-1.56 (m, 2H). |
| 28 | 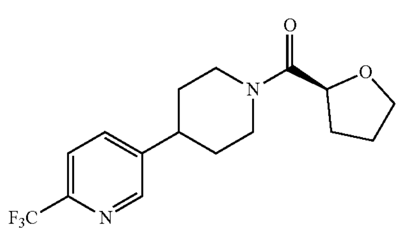 [SMILES: O=C([C@@H]1CCCO1)N1CCC(c2ccc(C(F)(F)F)nc2)CC1] | LC/MS ([M + H]⁺/Rt (min)): 329.2/0.80 (Analytical condition A) ¹H-NMR (400 MHz, CDCl₃) δ: 8.57 (d, 1H, J = 2.0 Hz), 7.67-7.60 (m, 2H), 4.78 (d, 1H, J = 13.2 Hz), 4.65-4.60 (m, 1H), 4.26 (d, 1H, J = 13.2 Hz), 3.96-3.90 (m, 1H), 3.86-3.81 (m, 1H), 3.22-3.07 (m, 1H), 2.94-2.85 (m, 1H), 2.73-2.63 (m, 1H), 2.35-2.27 (m, 1H), 2.10-1.85 (m, 5H), 1.78-1.56 (m, 2H). |

TABLE 3-continued

| Example | Chemical structure | Instrumental analysis |
|---|---|---|
| 29 | 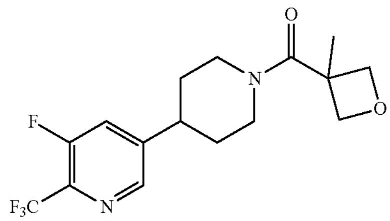 [SMILES: CC1(C(=O)N2CCC(c3cnc(C(F)(F)F)c(F)c3)CC2)COC1] | LC/MS ([M + H]⁺/Rt (min)): 347.2/0.86 (Analytical condition A) ¹H-NMR (400 MHz, CDCl₃) δ: 8.37 (1H, s), 7.41-7.38 (1H, m), 4.98 (2H, d, J = 6.0 Hz), 4.80 (1H, d, J = 12.8 Hz), 4.36-4.35 (2H, m), 3.14-3.12 (2H, m), 2.95-2.87 (1H, m), 2.68 (1H, t, J = 12.8 Hz), 1.95 (2H, brs), 1.71-1.51 (2H, m), 1.68 (s, 3H). |
| 30 | 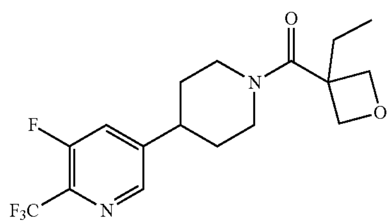 [SMILES: CCC1(C(=O)N2CCC(c3cnc(C(F)(F)F)c(F)c3)CC2)COC1] | LC/MS ([M + H]⁺/Rt (min)): 361.2/0.90 (Analytical condition A) ¹H-NMR (400 MHz, CDCl₃) δ: 8.37 (1H, s), 7.40-7.38 (1H, m), 4.95 (2H, d, J = 6.4 Hz), 4.83 (1H, d, J = 12.8 Hz), 4.40 (2H, d, J = 5.2 Hz), 3.14-3.12 (2H, m), 2.95-2.87 (1H, m), 2.68 (1H, t, J = 12.8 Hz), 2.07-1.93 (4H, m), 1.66-1.49 (2H, m), 1.00 (3H, d, J = 7.2 Hz). |
| 31 | 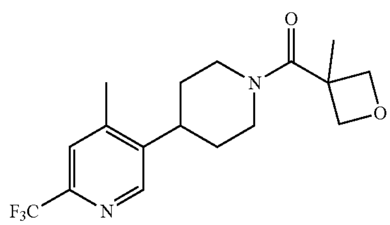 [SMILES: Cc1cc(C(F)(F)F)ncc1C1CCN(C(=O)C2(C)COC2)CC1] | LC/MS ([M + H]⁺/Rt (min)): 343.2/0.83 (Analytical condition A) ¹H-NMR (400 MHz, CDCl₃) δ: 8.46 (1H, s), 7.45 (1H, s), 5.00 (2H, d, J = 4.4 Hz), 4.81 (1H, d, J = 12.8 Hz), 4.36 (2H, brs), 3.14-3.12 (2H, m), 3.03-2.95 (1H, m), 2.67 (1H, t, J = 12.8 Hz), 2.43 (3H, s), 1.90-1.84 (2H, m), 1.77-1.65 (2H, m), 1.69 (s, 3H). |
| 32 | | LC/MS ([M + H] |/Rt (min)): 357.2/0.87 (Analytical condition A) ¹H-NMR (400 MHz, CDCl₃) δ: 8.46 (1H, s), 7.45 (1H, s), 5.00-4.94 (2H, m), 4.84 (1H, d, J = 12.8 Hz), 4.40 (2H, d, J = 5.6 Hz), 3.14-3.12 (2H, m), 3.03-2.95 (1H, m), 2.67 (1H, t, J = 12.8 Hz), 2.46 (3H, s), 2.07-1.58 (6H, m), 1.00 (3H, d, J = 7.6 Hz). |

Example 33

(3-Methylazetidin-3-yl){4-[6-(trifluoromethyl)pyridin-3-yl]piperidin-1-yl}methanone

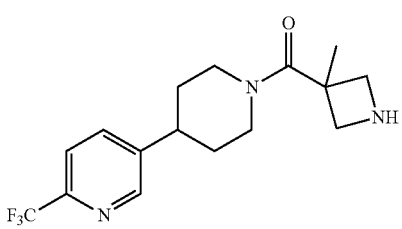 [SMILES: CC1(C(=O)N2CCC(c3ccc(C(F)(F)F)nc3)CC2)CNC1]

To a solution of Reference example 1 (50 mg) in chloroform (1.0 mL) were added 1-(tert-butoxycarbonyl)-3-methylazetidine-3-carboxylic acid (56 mg), triethylamine (45 μL), HATU (99 mg), and cesium carbonate (71 mg). The reaction solution was stirred at room temperature for one hour, and then roughly purified by amino silica gel chromatography (elute solvent; hexane/ethyl acetate→ethyl acetate/methanol) to give a crude product. The obtained crude product was dissolved in chloroform (1.0 mL), and TFA (1.0 mL) was added thereto. The mixture was stirred at room temperature for 5 minutes. The reaction solution was concentrated and purified by amino silica gel chromatography (elute solvent; hexane/ethyl acetate→ethyl acetate/methanol) to give Example 33 (65 mg).

LC/MS ([M+H]⁺/Rt (min)): 328.2/0.60 (Analytical condition A) ¹H-NMR (400 MHz, DMSO-d₆) δ: 8.71 (1H, d, J=2.0 Hz), 8.00 (1H, dd, J=8.4, 2.0 Hz), 7.83 (1H, d, J=8.4 Hz), 4.53 (1H, d, J=12.8 Hz), 3.87 (2H, t, J=8.4 Hz), 3.35-3.30 (1H, m), 3.16-3.07 (3H, m), 2.97 (1H, tt, J=12, 3.6 Hz), 2.63 (1H, t, J=12 Hz), 1.84 (2H, d, J=12.8 Hz), 1.65-1.47 (5H, m).

Alternatively, the compound of Example 33 can be also prepared according to the following process.

To a solution of hydrochloride of Reference example 1 (100 mg) in ethyl acetate (1.0 mL) were added 1-(tert-butoxycarbonyl)-3-methylazetidine-3-carboxylic acid (97 mg), triethylamine (0.17 mL), and a solution of 2,4,6-tripropyl-1,3,5,2,4,6-trioxatriphosphorinane-2,4,6-trioxide in ethyl acetate (50%, 0.40 mL), and the mixture was stirred at room temperature for one hour. The reaction solution was roughly purified by silica gel chromatography (elute solvent; ethyl acetate/methanol) to give a crude product. The obtained crude product was dissolved in chloroform (1.0 mL), and TFA (1.0 mL) was added thereto. The mixture was stirred at room temperature for one hour. The reaction solution was concentrated and purified by amino silica gel chromatography (elute solvent; ethyl acetate/methanol) to give Example 33 (90 mg)

Examples 34-40

The compounds shown in Table 4 were prepared from each corresponding starting compound according to the process described in Example 33. In case that the example compound is a salt, the salting step is also included.

TABLE 4

| Example | Chemical structure | Instrumental analysis |
| --- | --- | --- |
| 34 | 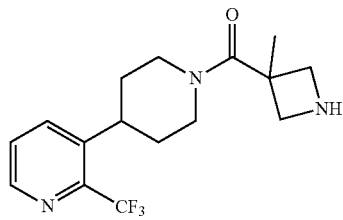 [SMILES: CC1(C(=O)N2CCC(c3cccnc3C(F)(F)F)CC2)CNC1] | LC/MS ([M + H]$^+$/Rt (min)): 328.1/1.25 (Analytical condition B)<br>$^1$H-NMR (400 MHz, DMSO-d$_6$) δ: 8.57 (1H, d, J = 3.6 Hz), 8.22-8.21 (1H, m), 7.70-7.67 (1H, m), 4.56-4.54 (1H, m), 4.21-4.11 (1H, m), 3.96-3.90 (1H, m), 3.35-3.09 (5H, m), 2.70-2.62 (1H, m), 1.79-1.62 (4H, m), 1.51 (3H, s). |
| 35 | 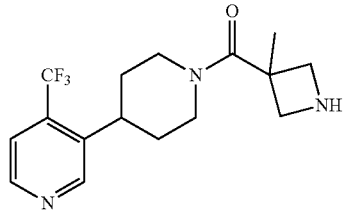 [SMILES: CC1(C(=O)N2CCC(c3cnccc3C(F)(F)F)CC2)CNC1] | LC/MS ([M + H]$^+$/Rt (min)): 328.3/1.62 (Analytical condition B)<br>$^1$H-NMR (500 MHz, DMSO-d$_6$) δ: 8.97 (1H, s), 8.70 (1H, d, J = 5.0 Hz), 7.69 (1H, d, J = 5.5 Hz), 4.56-4.53 (1H, m), 4.17-4.08 (2H, m), 3.50 (2H, d, J = 9.0 Hz), 3.33-3.30 (1H, m), 3.18-3.13 (1H, m), 3.08-3.02 (1H, m), 2.71-2.62 (1H, m), 1.90-1.75 (4H, m), 1.55 (3H, s). |
| 36 | 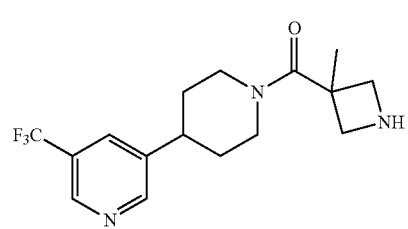 [SMILES: CC1(C(=O)N2CCC(c3cncc(C(F)(F)F)c3)CC2)CNC1] | LC/MS ([M + H]$^+$/Rt (min)): 328.1/1.28 (Analytical condition B)<br>$^1$H-NMR (500 MHz, CDCl$_3$) δ: 8.78 (1H, s), 8.70 (1H, s), 7.76 (1H, s), 4.80-4.78 (1H, m), 4.25-4.24 (2H, m), 3.53-3.52 (2H, m), 3.39-3.37 (1H, m), 3.19-3.14 (1H, m), 2.94-2.87 (1H, m), 2.73-2.69 (1H, m), 1.98-1.96 (2H, m), 1.76-1.61 (5H, m). |
| 37 | 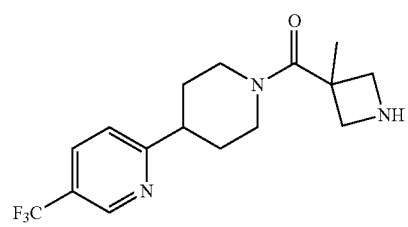 [SMILES: CC1(C(=O)N2CCC(c3ccc(C(F)(F)F)cn3)CC2)CNC1] | LC/MS ([M + H]$^+$/Rt (min)): 328.2/1.26 (Analytical condition B)<br>$^1$H-NMR (500 MHz, CDCl$_3$) δ: 8.80 (1H, s), 7.89-7.87 (1H, m), 7.30 (1H, d, J = 8.5 Hz), 4.74-4.72 (1H, m), 4.19-4.17 (2H, m), 3.48-3.44 (3H, m), 3.39-3.37 (1H, m), 3.14-3.12 (1H, m), 3.05-3.00 (1H, m), 2.74-2.72 (1H, m), 2.00-1.98 (2H, m), 1.80-1.76 (2H, m), 1.67 (3H, s). |

TABLE 4-continued

| Example | Chemical structure | Instrumental analysis |
|---|---|---|
| 38 | 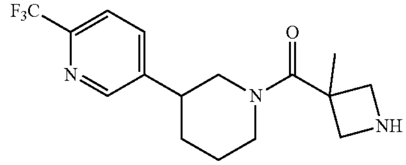 [SMILES: CC1(C(=O)N2CCCC(c3ccc(C(F)(F)F)nc3)C2)CNC1] | LC/MS ([M + H]⁺/Rt (min)): 328.2/1.38 (Analytical condition B) $^1$H-NMR (400 MHz, CD$_3$OD) δ: 8.68 (1H, s), 8.01 (1H, d, J = 7.6 Hz), 7.81 (1H, d, J = 8.0 Hz), 4.66-4.54 (1H, m), 4.24-4.13 (2H, m), 3.53-3.39 (3H, m), 3.23-3.15 (1H, m), 3.01-2.89 (2H, m), 2.13-2.09 (1H, m), 1.95-1.85 (2H, m), 1.66-1.63 (4H, m). |
| 39 | 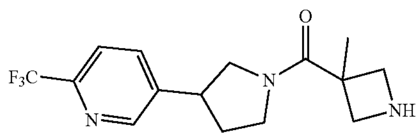 [SMILES: CC1(C(=O)N2CCC(c3ccc(C(F)(F)F)nc3)C2)CNC1] | LC/MS ([M + H]⁺/Rt (min)): 314.2/1.53 (Analytical condition B) $^1$H-NMR (500 MHz, CDCl$_3$) δ: 8.62 (1H, s), 7.75-7.73 (1H, m), 7.68-7.66 (1H, m), 4.20-4.14 (2H, m), 4.05-4.02 (0.5H, m), 3.82-3.78 (0.5H, m), 3.66-3.25 (6H, m), 2.47-2.35 (1H, m), 2.13-2.00 (1H, m), 1.67-1.62 (3H, m). |
| 40 | 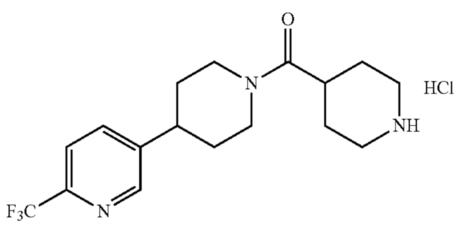 [SMILES: O=C(C1CCNCC1)N1CCC(c2ccc(C(F)(F)F)nc2)CC1 ; Cl] | LC/MS ([M + H]⁺/Rt (min)): 342.2/0.58 (Analytical condition A) $^1$H-NMR (400 MHz, DMSO-d$_6$) δ: 8.70 (1H, d, J = 2.0 Hz), 7.98 (1H, dd, J = 8.4, 2.0 Hz), 7.83 (1H, d, J = 8.0 Hz), 7.30 (1H, brs), 4.57 (1H, d, J = 12.8 Hz), 4.11 (1H, d, J = 13.2 Hz), 3.32 (1H, brs), 3.16-3.10 (3H, m), 2.99 (1H, tt, J = 12.8, 3.2 Hz), 2.91-2.84 (1H, m), 2.76 (2H, td, J = 11.6, 3.6 Hz), 2.61 (1H, t, J = 11.6 Hz), 1.89-1.82 (2H, m), 1.67-1.49 (6H, m). |

Example 41

(1,3-Dimethylazetidin-3-yl){4-[6-(trifluoromethyl)pyridin-3-yl]piperidin-1-yl}methanone hydrochloride

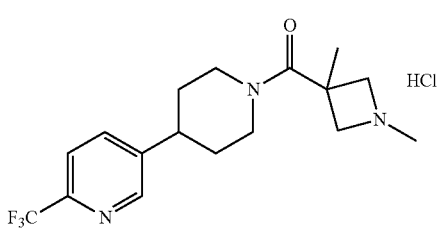 [SMILES: CN1CC(C)(C(=O)N2CCC(c3ccc(C(F)(F)F)nc3)CC2)C1 ; Cl]

To a solution of Example 33 (20 mg) in THF (0.50 mL) were added 36% aqueous formaldehyde (19 μL) and acetic acid (5.2 μL). And, sodium triacetoxyborohydride (39 mg) was added to the solution while stirring the solution at room temperature. The reaction solution was stirred for 30 minutes, and purified by amino silica gel chromatography (elute solvent; hexane/ethyl acetate→ethyl acetate/methanol). The obtained oily compound was dissolved in ethyl acetate (1 mL), and reacted with 4 mol/L hydrochloric acid in ethyl acetate at room temperature to give Example 41 (15 mg).

LC/MS ([M+H]⁺/Rt(min)): 342.3/0.63 (Analytical condition A) $^1$H-NMR (400 MHz, DMSO-d$_6$) δ: 10.6 (1H, brs), 8.72 (1H, d, J=1.6 Hz), 7.99 (1H, dd, J=8.0, 1.6 Hz), 7.86 (1H, d, J=8.8 Hz), 4.52 (1H, d, J=12.8 Hz), 4.13-4.12 (2H, m), 3.92-3.90 (2H, m), 3.32-3.29 (1H, m), 3.15 (1H, t, J=12.8 Hz), 3.00 (1H, tt, J=12, 3.2 Hz), 2.72 (3H, s), 1.91-1.83 (2H, m), 1.68-1.50 (5H, m).

Examples 42-48

The compounds shown in Table 5 were prepared from each corresponding starting compound according to the process described in Example 41. In case that the example compound is not a salt, the salting step was not needed.

TABLE 5

| Example | Chemical structure | Instrumental analysis |
| --- | --- | --- |
| 42 | 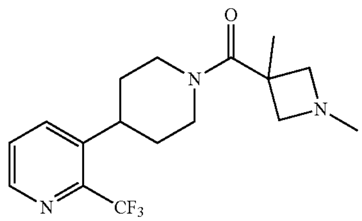 [SMILES: CN1CC(C)(C(=O)N2CCC(c3cccnc3C(F)(F)F)CC2)C1] | LC/MS ([M + H]⁺/Rt (min)): 342.2/1.38 (Analytical condition B) ¹H-NMR (500 MHz, DMSO-d₆) δ: 8.57 (1H, d, J = 4.5 Hz), 8.20 (1H, d, J = 8.5 Hz), 7.70-7.67 (1H, m), 4.54-4.52 (1H, m), 3.39-3.30 (1H, m), 3.20-3.08 (6H, m), 2.65-2.61 (1H, m), 2.19 (3H, s), 1.69-1.60 (4H, m), 1.48 (3H, s). |
| 43 | 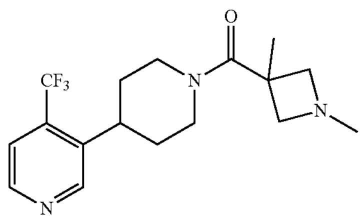 [SMILES: CN1CC(C)(C(=O)N2CCC(c3cnccc3C(F)(F)F)CC2)C1] | LC/MS ([M + H]⁺/Rt (min)): 342.2/1.40 (Analytical condition B) ¹H-NMR (500 MHz, CD₃OD): δ 8.87 (1H, s), 8.66 (1H, d, J = 5.5 Hz), 7.69 (1H, d, J = 5.0 Hz), 4.72-4.69 (1H, m), 3.53-3.39 (5H, m), 3.26-3.22 (2H, m), 2.79-2.73 (1H, m), 2.37 (3H, s), 1.89-1.82 (4H, m), 1.62 (3H, s). |
| 44 | 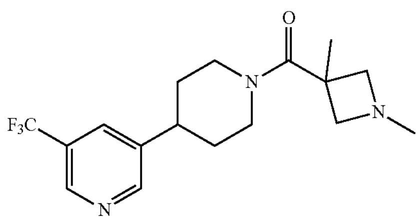 [SMILES: CN1CC(C)(C(=O)N2CCC(c3cncc(C(F)(F)F)c3)CC2)C1] | LC/MS ([M + H]⁺/Rt (min)): 342.2/1.40 (Analytical condition B) ¹H-NMR (500 MHz, DMSO-d₆) δ: 8.83 (2H, s), 8.15 (1H, s), 4.53-4.51 (1H, m), 3.38-3.33 (1H, m), 3.18-3.07 (5H, m), 2.99-2.94 (1H, m), 2.64-2.59 (1H, m), 2.18 (3H, s), 1.83-1.81 (2H, m), 1.70-1.68 (1H, m), 1.60-1.57 (1H, m), 1.48 (3H, s). |
| 45 | 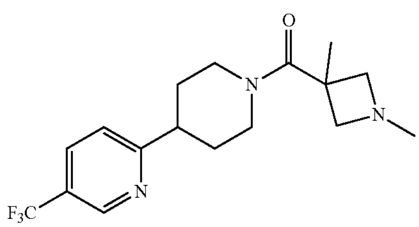 [SMILES: CN1CC(C)(C(=O)N2CCC(c3ccc(C(F)(F)F)cn3)CC2)C1] | LC/MS ([M + H]⁺/Rt (min)): 342.2/1.39 (Analytical condition B) ¹H-NMR (500 MHz, CDCl₃) δ: 8.80 (1H, s), 7.88-7.86 (1H, m), 7.29 (1H, d, J = 9.0 Hz), 4.74-4.71 (1H, m), 3.46-3.44 (1H, m), 3.37-3.36 (2H, m), 3.30-3.29 (2H, m), 3.13-3.08 (1H, m), 3.03-2.98 (1H, m), 2.72-2.68 (1H, m), 2.31 (3H, s), 1.99-1.97 (2H, m), 1.79-1.74 (2H, m), 1.61 (3H, s). |
| 46 | 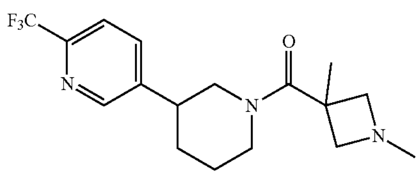 [SMILES: CN1CC(C)(C(=O)N2CCCC(c3ccc(C(F)(F)F)nc3)C2)C1] | LC/MS ([M + H]⁺/Rt (min)): 342.2/1.39 (Analytical condition B) ¹H-NMR (500 MHz, CDCl₃) δ: 8.61-8.59 (1H, m), 7.73-7.63 (2H, m), 4.68-4.65 (1H, m), 3.37-3.32 (2H, m), 3.30-3.26 (2H, m), 3.02-3.00 (1H, m), 2.82-2.80 (1H, m), 2.69-2.63 (2H, m), 2.30-2.28 (3H, m), 2.11-2.09 (1H, m), 1.88-1.85 (1H, m), 1.75-1.73 (1H, m), 1.62-1.56 (4H, m). |
| 47 | 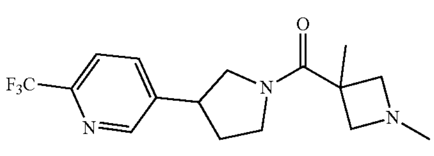 [SMILES: CN1CC(C)(C(=O)N2CCC(c3ccc(C(F)(F)F)nc3)C2)C1] | LC/MS ([M + H]⁺/Rt (min)): 328.2/1.65 (Analytical condition B) ¹H-NMR (500 MHz, CDCl₃) δ: 8.62 (1H, s), 7.73-7.72 (1H, m), 7.68-7.66 (1H, m), 4.05-4.02 (0.5H, m), 3.81-3.78 (0.5H, m), 3.68-3.58 (1H, m), 3.54-3.33 (4H, m), 3.28-3.22 (3H, m), 2.47-2.37 (1H, m), 2.31-2.29 (3H, m), 2.09-1.99 (1H, m), 1.67-1.62 (3H, |

TABLE 5-continued

| Example | Chemical structure | Instrumental analysis |
|---|---|---|
| | m). | |
| 48 | 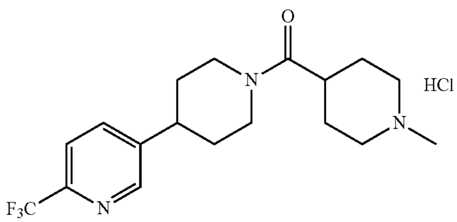 [SMILES: CN1CCC(C(=O)N2CCC(c3ccc(C(F)(F)F)nc3)CC2)CC1 ; Cl] | LC/MS ([M + H]⁺/Rt (min)): 356.2/0.58 (Analytical condition A) $^1$H-NMR (400 MHz, DMSO-$d_6$) δ: 9.91 (1H, brs), 8.71 (1H, d, J = 2.0 Hz), 7.98 (1H, dd, J = 8.8, 2.0 Hz), 4.57 (1H, d, J = 12 Hz), 4.09 (2H, d, J = 13.2 Hz), 3.27-3.12 (3H, m), 2.99 (1H, tt, J = 12, 3.6 Hz), 2.85-2.54 (6H, m), 1.90-1.49 (9H, m). |

Example 49

(Morpholin-4-yl){4-[6-(trifluoromethyl)pyridin-3-yl]piperidin-1-yl}methanone

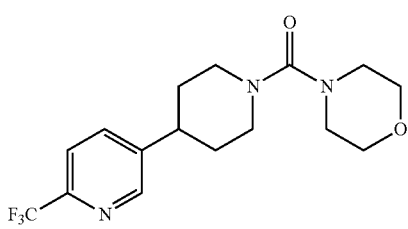

To a solution of Reference example 1 (30 mg) in chloroform (1.0 mL) were added morpholine-4-carbonylchloride (18 μL) and N-ethyl-N-isopropylpropan-2-amine (34 μL), and the mixture was stirred at room temperature for one hour. The reaction solution was purified by amino silica gel chromatography (elute solvent; hexane/ethyl acetate→ethyl acetate/methanol) to give Example 49 (44 mg).

LC/MS ([M+H]⁺/Rt (min)): 344.2/0.79 (Analytical condition A) 1H-NMR (400 MHz, DMSO-$d_6$) δ: 8.70 (1H, d, J=2.0 Hz), 7.98 (1H, dd, J=8.0, 2.0 Hz), 7.83 (1H, d, J=8.0 Hz), 3.74 (2H, d, J=13.6 Hz), 3.58 (4H, m), 3.15 (4H, m), 2.93-2.83 (3H, m), 1.82-1.79 (2H, m), 1.70-1.59 (2H, m).

Examples 50-59

The compounds shown in Table 6 were prepared from each corresponding starting compound according to the process described in Example 1.

TABLE 6

| Example | Chemical structure | Instrumental analysis |
|---|---|---|
| 50 | 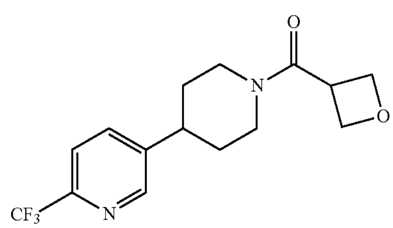 [SMILES: O=C(C1COC1)N1CCC(c2ccc(C(F)(F)F)nc2)CC1] | LC/MS ([M + H]⁺/Rt (min)): 314.9/1.40 (Analytical condition B) $^1$H-NMR (400 MHz, CDCl₃) δ: 8.60 (1H, s), 7.71-7.65 (2H, m), 5.00-4.92 (2H, m), 4.87-4.82 (3H, m), 4.10-4.02 (1H, m), 3.50-3.47 (1H, m), 3.18-3.11 (1H, m), 2.94-2.88 (1H, m), 2.77-2.70 (1H, m), 1.98-1.94 (2H, m), 1.73-1.52 (2H, m). |
| 51 | 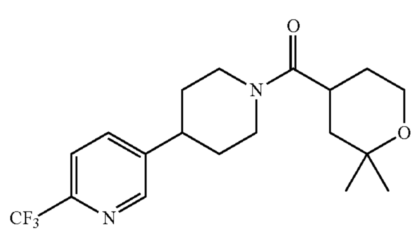 [SMILES: CC1(C)CC(C(=O)N2CCC(c3ccc(C(F)(F)F)nc3)CC2)CCO1] | LC/MS ([M + H]⁺/Rt (min)): 371.0/1.60 (Analytical condition B) $^1$H-NMR (400 MHz, CDCl₃) δ: 8.63 (1H, s), 7.73-7.66 (2H, m), 4.88 (1H, d, J = 14.0 Hz), 4.10 (1H, d, J = 13.6 Hz), 3.87-3.83 (1H, m), 3.76-3.70 (1H, m), 3.27-3.20 (1H, m), 2.95-2.92 (2H, m), 2.71-2.64 (1H, m), 2.04-1.93 (2H, m), 1.86-1.65 (4H, m), 1.63-1.60 (2H, m), 1.28 (6H, s). |

TABLE 6-continued

| Example | Chemical structure | Instrumental analysis |
|---|---|---|
| 52 | 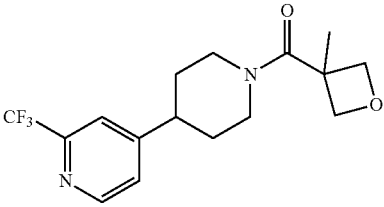 [SMILES: CC1(C(=O)N2CCC(c3ccnc(C(F)(F)F)c3)CC2)COC1] | LC/MS ([M + H]⁺/Rt (min)): 329.1/1.59 (Analytical condition B) $^1$H-NMR (400 MHz, DMSO-d$_6$) δ: 8.67 (1H, d, J = 5.2 Hz), 7.87 (1H, s), 7.65 (1H, d, J = 4.8 Hz), 4.84 (2H, dd, J = 13.6, 1.2 Hz), 4.53 (1H, d, J = 12.8 Hz), 4.27 (2H, dd, J = 9.6, 6.0 Hz), 3.12-2.93 (3H, m), 2.67-2.61 (1H, m), 1.85-1.67 (3H, m), 1.58-1.57 (1H, m), 1.56 (3H, s). |
| 53 | 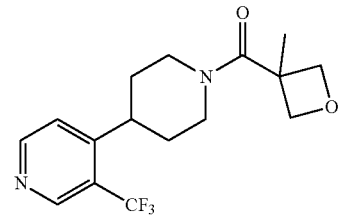 [SMILES: CC1(C(=O)N2CCC(c3ccncc3C(F)(F)F)CC2)COC1] | LC/MS ([M + H]⁺/Rt (min)): 329.1/1.55 (Analytical condition B) $^1$H-NMR (400 MHz, CDCl$_3$) δ: 8.87 (1H, s), 8.76 (1H, d, J = 5.6 Hz), 7.33 (1H, d, J = 5.2 Hz), 5.03 (2H, d, J = 4.8 Hz), 4.82 (1H, d, J = 12.4 Hz), 4.39 (2H, t, J = 5.6 Hz), 3.21-3.10 (3H, m), 2.73-2.67 (1H, m), 1.90 (2H, d, J = 12.8 Hz), 1.71 (3H, s), 1.69-1.59 (2H, m). |
| 54 | 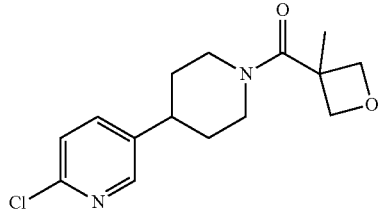 [SMILES: CC1(C(=O)N2CCC(c3ccc(Cl)nc3)CC2)COC1] | LC/MS ([M + H]⁺/Rt (min)): 295.1/1.54 (Analytical condition B) $^1$H-NMR (400 MHz, DMSO-d$_6$) δ: 8.34 (1H, d, J = 2.4 Hz), 7.80 (1H, dd, J = 8.4, 2.4 Hz), 7.44 (1H, d, J = 8.4 Hz), 4.83-4.80 (2H, m), 4.51 (1H, d, J = 13.2 Hz), 4.27 (2H, t, J = 6.8 Hz), 3.14-3.03 (2H, m), 2.87-2.81 (1H, m), 2.66-2.60 (1H, m), 1.80-1.75 (2H, m), 1.66-1.46 (5H, m). |
| 55 | 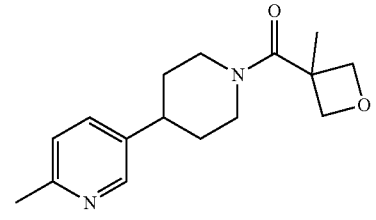 [SMILES: Cc1ccc(C2CCN(C(=O)C3(C)COC3)CC2)cn1] | LC/MS ([M + H]⁺/Rt (min)): 275.1/1.38 (Analytical condition B) $^1$H-NMR (400 MHz, DMSO-d$_6$) δ: 8.34 (1H, d, J = 2.0 Hz), 7.58 (1H, dd, J = 7.6, 2.0 Hz), 7.17 (1H, d, J = 8.0 Hz), 4.81 (2H, t, J = 6.4 Hz), 4.51 (1H, d, J = 12.4 Hz), 4.27 (2H, t, J = 6.4 Hz), 3.14-3.01 (2H, m), 2.80-2.74 (1H, m), 2.67-2.60 (1H, m), 2.41 (3H, s), 1.78-1.75 (2H, m), 1.63-1.59 (1H, m), 1.55 (3H, s), 1.51-1.43 (1H, m). |
| 56 | 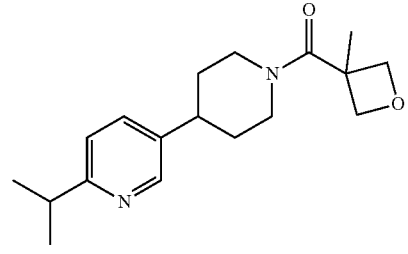 [SMILES: CC(C)c1ccc(C2CCN(C(=O)C3(C)COC3)CC2)cn1] | LC/MS ([M + H]⁺/Rt (min)): 303.2/1.62 (Analytical condition B) $^1$H-NMR (400 MHz, DMSO-d$_6$) δ: 8.38 (1H, d, J = 2.4 Hz), 7.61 (1H, dd, J = 7.6, 2.0 Hz, ), 7.19 (1H, d, J = 8.0 Hz), 4.81 (2H, t, J = 6.0 Hz), 4.51 (1H, d, J = 13.6 Hz), 4.27 (2H, t, J = 6.0 Hz), 3.12-2.95 (3H, m), 2.80-2.74 (1H, m), 2.67-2.61 (1H, m), 1.79-1.75 (2H, m), 1.60-1.59 (1H, m), 1.55 (3H, s), 1.52-1.51 (1H, m), 1.20 (6H, d, J = 6.8 Hz). |

TABLE 6-continued

| Example | Chemical structure | Instrumental analysis |
|---|---|---|
| 57 | 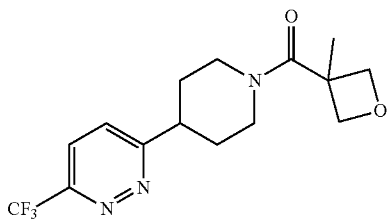 [SMILES: CC1(C(=O)N2CCC(c3ccc(C(F)(F)F)nn3)CC2)COC1] | LC/MS ([M + H]⁺/Rt (min)): 330.1/1.48 (Analytical condition B) $^1$H-NMR (400 MHz, CDCl$_3$) δ: 7.81 (1H, d, J = 8.4 Hz), 7.55 (1H, d, J = 8.8 Hz), 5.03 (2H, d, J = 5.6 Hz), 4.79 (1H, d, J = 14.0 Hz), 4.39 (2H, d, J = 6.0 Hz), 3.37-3.29 (1H, m), 3.1 (2H, d, J = 7.6 Hz), 2.87-2.80 (1H, m), 2.14-2.10 (2H, m), 1.95-1.85 (2H, m), 1.72 (3H, s). |
| 58 | 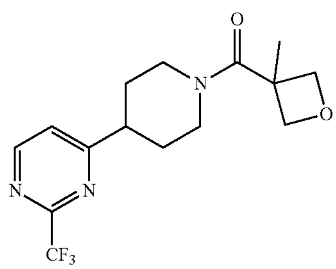 [SMILES: CC1(C(=O)N2CCC(c3ccnc(C(F)(F)F)n3)CC2)COC1] | LC/MS ([M + H]⁺/Rt (min)): 330.1/1.58 (Analytical condition B) $^1$H-NMR (400 MHz, CDCl$_3$) δ: 8.85 (1H, d, J = 4.8 Hz), 7.38 (1H, d, J = 5.6 Hz), 5.02 (2H, d, J = 6.4 Hz), 4.76 (1H, d, J = 13.6 Hz), 4.39-4.38 (2H, m), 3.17-3.15 (2H, m), 3.08-3.03 (1H, m), 2.81-2.75 (1H, m), 2.08 (2H, d, J = 13.2 Hz), 1.80-1.79 (2H, m), 1.71 (3H, s). |
| 59 | 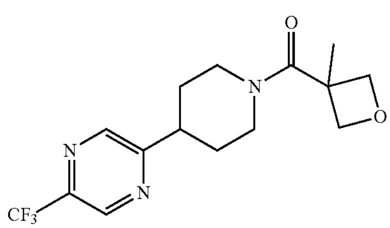 | LC/MS ([M + H]⁺/Rt (min)): 330.1/1.61 (Analytical condition B) $^1$H-NMR (400 MHz, DMSO-d$_6$) δ: 9.11 (1H, s), 8.88 (1H, s), 4.80 (2H, d, J = 6.0 Hz), 4.50 (1H, d, J = 12.8 Hz), 4.28 (2H, d, J = 6.0 Hz), 3.26-3.08 (3H, m), 2.76-2.70 (1H, m), 1.95 (2H, d, J = 13.2 Hz), 1.75-1.60 (2H, m), 1.56 (3H, s). |

Example 60

(1,4-Oxazepan-4-yl){4-[6-(trifluoromethyl)pyridin-3-yl]piperidin-1-yl}methanone

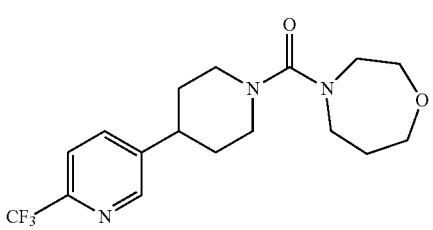 [SMILES: O=C(N1CCCOCC1)N1CCC(c2ccc(C(F)(F)F)nc2)CC1]

To a solution of 1,4-oxazepane (61 mg) in dichloromethane (2.0 mL) was added pyridine (95 mg), and the mixture was cooled to 0° C. Triphosgene (72 mg) was added thereto, and the mixture was stirred at 0° C. for 30 minutes. Diisopropylethylamine (0.23 g) and Reference example 1 (69 mg) were added to the reaction solution, and the reaction solution was stirred at room temperature for one hour. The reaction solution was concentrated and purified by preparative HPLC to give Example 60 (31 mg).

LC/MS ([M+H]⁺/Rt(min)): 357.9/1.54 (Analytical condition B) $^1$H-NMR (500 MHz, CDCl$_3$) δ: 8.63 (1H, s), 7.74-7.72 (1H, m), 7.66 (1H, d, J=8.0 Hz), 3.83-3.79 (6H, m), 3.55-3.52 (4H, m), 2.95-2.90 (2H, m), 2.86-2.81 (1H, m), 2.02-2.00 (2H, m), 1.91 (2H, d, J=11.0 Hz), 1.80-1.72 (2H, m).

Examples 61-63

The compounds shown in Table 7 were prepared from each corresponding starting compound according to the process described in Example 60.

TABLE 7

| Example | Chemical structure | Instrumental analysis |
|---|---|---|
| 61 | 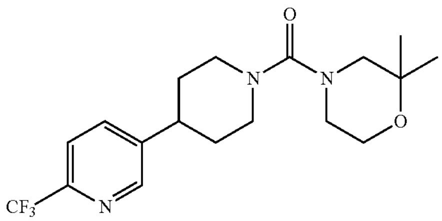 [SMILES: CC1(C)CN(C(=O)N2CCC(c3ccc(C(F)(F)F)nc3)CC2)CCO1] | LC/MS ([M + H]⁺/Rt (min)): 372.3/1.91 (Analytical condition B) ¹H-NMR (400 MHz, CDCl₃) δ: 8.63 (1H, s), 7.74-7.72 (1H, m), 7.66 (1H, d, J = 8.4 Hz), 3.88 (2H, d, J = 13.2 Hz), 3.80-3.78 (2H, m), 3.28 (2H, d, J = 5.2 Hz), 3.12 (2H, s), 2.98-2.92 (2H, m), 2.87-2.81 (1H, m), 1.91 (2H, d, J = 11.6 Hz), 1.79-1.72 (2H, m), 1.27 (6H, s). |
| 62 | 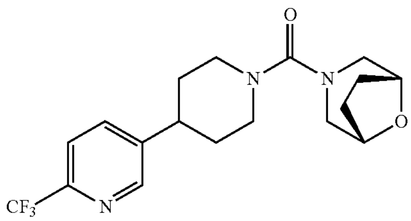 [SMILES: O=C(N1CCC(c2ccc(C(F)(F)F)nc2)CC1)N1C[C@H]2CC[C@@H](C1)O2] | LC/MS ([M + H]⁺/Rt (min)): 369.9/1.56 (Analytical condition B) ¹H-NMR (500 MHz, CDCl₃) δ: 8.63 (1H, d, J = 1.0 Hz), 7.73 (1H, dd, J = 8.0, 1.5 Hz), 7.66 (1H, d, J = 8.5 Hz), 4.34 (2H, s), 3.79 (2H, d, J = 13.5 Hz), 3.54 (2H, d, J = 13.0 Hz), 3.28-3.25 (2H, m), 2.93-2.83 (3H, m), 1.96-1.89 (6H, m), 1.75-1.72 (2H, m). |
| 63 | 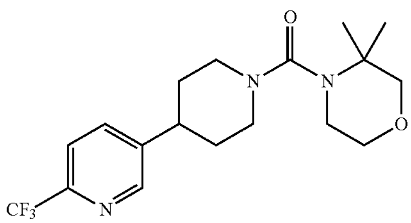 [SMILES: CC1(C)COCCN1C(=O)N1CCC(c2ccc(C(F)(F)F)nc2)CC1] | LC/MS ([M + H]⁺/Rt (min)): 372.3/1.96 (Analytical condition B) ¹H-NMR (500 MHz, CDCl₃) δ: 8.62 (1H, s), 7.72-7.70 (1H, m), 7.66 (1H, d, J = 8.5 Hz), 4.05 (2H, brs), 3.76 (2H, t, J = 5.0 Hz), 3.35 (2H, s), 3.18 (2H, brs), 2.94-2.89 (3H, m), 1.91 (2H, d, J = 10.5 Hz), 1.70-1.67 (2H, m), 1.37 (6H, s). |

Examples 64-65

The compounds shown in Table 8 were prepared from each corresponding starting compound according to the process described in Example 41. In case that the example compound is not a salt, the salting step was not needed.

TABLE 8

| Example | Chemical structure | Instrumental analysis |
|---|---|---|
| 64 | 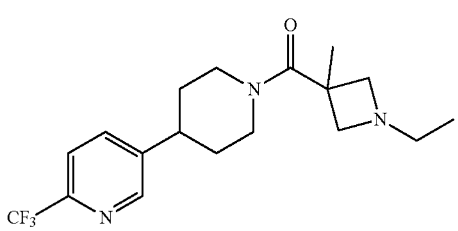 [SMILES: CCN1CC(C)(C(=O)N2CCC(c3ccc(C(F)(F)F)nc3)CC2)C1] | LC/MS ([M + H]⁺/Rt (min)): 356.0/1.44 (Analytical condition B) ¹H-NMR (400 MHz, CDCl₃) δ: 8.59 (1H, dd, J = 4.4, 1.2 Hz), 7.79 (1H, d, J = 7.6 Hz), 7.51 (1H, dd, J = 8.0, 4.4 Hz), 4.81 (1H, d, J = 13.6 Hz), 3.48 (1H, dd, J = 13.6 Hz), 3.38-3.36 (2H, m), 3.31-3.29 (2H, m), 3.23-3.13 (2H, m), 2.69 (1H, t, J = 12.4 Hz), 2.49 (2H, q, J = 7.2 Hz), 1.89 (2H, d, J = 13.2 Hz), 1.70-1.65 (2H, m), 1.62 (3H, s), 0.99 (3H, t, J = 7.2 Hz). |

| Example | Chemical structure | Instrumental analysis |
|---|---|---|
| 65 | 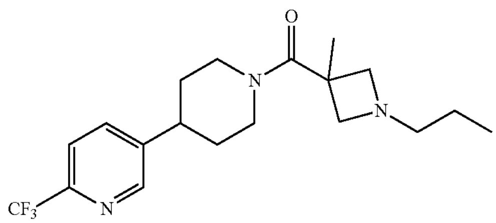 [SMILES: CCCN1CC(C)(C(=O)N2CCC(c3ccc(C(F)(F)F)nc3)CC2)C1] | LC/MS ([M + H]$^+$/Rt (min)): 370.1/1.70 (Analytical condition B) $^1$H-NMR (400 MHz, DMSO-d$_6$) δ: 8.57-8.56 (1H, m), 8.20 (1H, d, J = 8.0 Hz), 7.68 (1H, dd, J = 8.0, 4.4 Hz), 4.52 (1H, d, J = 13.2 Hz), 3.41-3.38 (1H, m), 3.15-3.09 (6H, m), 2.67-2.59 (1H, m), 2.27 (2H, t, J = 7.2 Hz), 1.71-1.60 (4H, m), 1.48 (3H, s), 1.29-1.23 (2H, m), 0.83 (3H, t, J = 7.2 Hz). |

Example 66

[3-Methyl-1-(2,2,2-trifluoroethyl)azetidin-3-yl]{4-[2-(trifluoromethyl)pyridin-3-yl]piperidin-1-yl}methanone

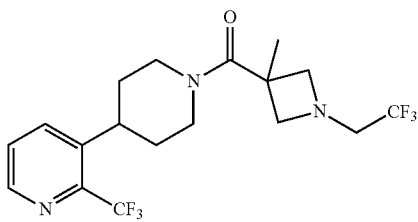 [SMILES: CC1(C(=O)N2CCC(c3cccnc3C(F)(F)F)CC2)CN(CC(F)(F)F)C1]

To a solution of Example 34 (46 mg) in THF (3.0 mL) were added 2,2,2-trifluoroethyltrifluoromethanesulfonate (42 mg) and triethylamine (71 mg), and the mixture was stirred at room temperature overnight. The reaction solution was concentrated and purified by preparative HPLC to give Example 66 (19 mg).

LC/MS ([M+H]$^+$/Rt (min)): 410.1/1.78 (Analytical condition B) $^1$H-NMR (400 MHz, CDCl$_3$) δ: 8.59 (1H, d, J=4.8 Hz), 7.79 (1H, d, J=8.0 Hz), 7.51 (1H, dd, J=7.6, 4.8 Hz), 4.79 (1H, d, J=13.2 Hz), 3.54-3.50 (4H, m), 3.41 (1H, d, J=12.4 Hz), 3.26-3.17 (2H, m), 3.01 (2H, q, J=9.2 Hz), 2.69 (1H, t, J=12.8 Hz), 1.90 (2H, d, J=12.8 Hz), 1.81-1.77 (1H, m), 1.69 (3H, s), 1.67-1.57 (1H, m).

Example 67

(1-Cyclopropyl-3-methylazetidin-3-yl){4-[2-(trifluoromethyl)pyridin-3-yl]piperidin-1-yl}methanone

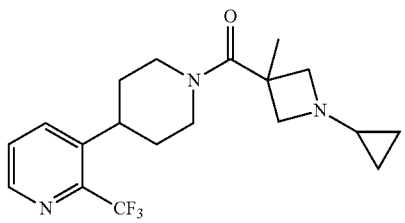 [SMILES: CC1(C(=O)N2CCC(c3cccnc3C(F)(F)F)CC2)CN(C2CC2)C1]

To a solution of Example 34 (46 mg) in ethanol (4.0 mL) were added (1-ethoxycyclopropoxy)trimethylsilane (73 mg), acetic acid (13 mg), and sodium cyanoborohydride (44 mg), and the mixture was stirred at 60° C. overnight. The reaction solution was cooled to room temperature and concentrated, and the residue was purified by preparative HPLC to give Example 67 (22 mg).

LC/MS ([M+H]$^+$/Rt (min)): 368.2/1.68 (Analytical condition B) 1H-NMR (400 MHz, CDCl$_3$) δ: 8.58 (1H, dd, J=4.4, 0.8 Hz), 7.79 (1H, d, J=8.0 Hz), 7.50 (1H, dd, J=8.0, 4.8 Hz), 4.81 (1H, d, J=12.8 Hz), 3.53-3.50 (3H, m), 3.38-3.31 (2H, m), 3.25-3.12 (2H, m), 2.76-2.65 (1H, m), 1.89-1.84 (3H, m), 1.71-1.61 (2H, m), 1.59 (3H, s), 0.38-0.35 (4H, m). homo Test 1: Reproduction Test of Parkinson's Disease Pathology (Accumulation of α-Synuclein Aggregate) with Neurospheroid Prepared by Three-Dimensional Culture of Human iPS Cells with a Mutation in PLA2G6 Gene PLA2G6 gene mutant cells established from healthy human-derived iPS cell line (Clone name: 201B7, obtained from iPS Cell Research and Application, Kyoto University) were cultured in StemFitAKO3N medium (Ajinomoto Co., Inc., Basic03) at 37° C. under 5% CO$_2$.

Neural stem cells were induced from iPS cells with PSC Neuronal Induction Medium (Thermo Fisher Scientific Inc., cat #A1647801) to prepare their cell stock.

The cryopreserved neural stem cells were cultured in culture medium at 37° C. under 5% CO$_2$. The culture medium used herein for neural stem cells had the following composition.

Culture medium composition for neural stem cell Neurobasal medium (Thermo Fisher Scientific Inc., 2113049)

Advanced DMEM/F-12 medium (Thermo Fisher Scientific Inc., 12634028)

Neural Induction Supplement (Thermo Fisher Scientific Inc., A1647801)

The neural stem cells (10000 cells/well) were seeded in 96-well round bottom plate (Thermo Fisher Scientific Inc., cat #174929), and cultured in a culture medium at 37° C. under 5% CO$_2$. Half of the culture solution was replaced every 3 to 4 days. The culture medium used herein for neurospheroid had the following composition.

BrainPhys Neuronal Medium (STEMCELL Technologies, cat #ST-05793)

NeuroCult SM1 Neuronal Supplement (STEMCELL Technologies, cat #05711)

N2 Supplement-A (STEMCELL Technologies, cat #07152)

20 ng/mL BDNF (PeproTech, Inc., cat #450-02)

20 ng/mL GDNF (PeproTech, Inc., cat #450-10)

1 mM dibutyryl cAMP (Nacalai Tesque, Inc., cat #11540-74)

200 nM ascorbic acid (Nacalai Tesque, Inc., cat #03420-52)

The differentiated neurospheroid was taken out from the culture medium, TBS solution (Nacalai Tesque, Inc., cat #12748-31) containing 1% TritionX-100 (Nacalai Tesque, Inc., cat #12967-32) was added thereto, and the protein was extracted from the mixture with an ultrasonicator.

The extracted protein was subjected to a protein analysis (Protein Simple, Inc., cat #SM-W008) under non-reducing conditions with Simple Western system using an α-synuclein antibody (Thermo Fisher Scientific Inc., cat #AHB0261) to measure the amount of the α-synuclein aggregate and evaluate the quantitation on the waveform shown at a molecular weight of about 300 kD.

The α-synuclein aggregate increased sharply from day 7 to day 9 of the culture. On day 9 of the culture, the amount of the α-synuclein aggregate in the neurospheroid derived from PLA2G6 mutant iPS cells was 5 times or more that of the neurospheroid derived from healthy iPS cells. After day 9 of the culture, it showed a slow increasing trend. The result is shown in FIG. 1.

Test 2: Evaluation of Suppressing the Accumulation of α-Synuclein Aggregate with Neurospheroid Prepared from Human iPS Cells with a Mutation in PLA2G6 Gene (1) Induction of Differentiation from Human iPS Cell to Neural Cell Neural stem cells were induced from PLA2G6 gene mutant iPS cells with PSC Neuronal Induction Medium (Thermo Fisher Scientific Inc., cat #A1647801). Neurospheroid was prepared from the induced neural stem cells by three-dimensional culture system, and preserved with BrainPhys Neuronal Medium (STEMCELL Technologies, cat #ST-05793) comprising NeuroCult SM1 Neuronal Supplement, N2 Supplement-A, 20 ng/mL BDNF, 20 ng/mL GDNF, 1 mM dibutyryl cAMP, and 200 nM ascorbic acid. Half of the culture medium was replaced on day 2 and day 4 after the induction of differentiation.

The test compound was diluted with the culture medium so as to be twice the final concentration, and an equal volume of the twice-concentrated solution was added to each well when half of the culture medium was replaced on day 4 after induction of differentiation.

(2) Evaluation of the Amount of α-Synuclein Aggregate

From the neurospheroid 9 days after the induction of differentiation, proteins were extracted with a TBS solution containing 1% TritionX-100, and the extracted proteins were subjected to a protein analysis with Simple Western system (Protein Simple, Inc., cat #SM-W008) using an α-synuclein antibody (Thermo Fisher Scientific Inc., cat #AHB0261) to measure the amount of the α-synuclein aggregate.

Assuming that the amount of the aggregate in the neurospheroid added with a DMSO solution is 100%, the amount of the aggregate in the neurospheroid added with each test compound was evaluated. Table 9 shows the amounts of the aggregate for representative test compounds.

TABLE 9

| Example | Amount of aggregate (%) 100 nM | Amount of aggregate (%) 1000 nM |
| --- | --- | --- |
| 1 | 14 | 16 |
| 2 | 9 | 1 |
| 3 | 6 | 10 |
| 4 | 30 | 29 |
| 5 | 22 | 90 |
| 6 | 97 | 81 |
| 7 | 23 | 52 |
| 8 | 7 | 13 |
| 9 | 8 | 50 |
| 10 | 25 | 29 |
| 11 | 3 | 97 |
| 12 | 35 | 12 |
| 13 | 11 | 7 |
| 14 | 37 | 22 |
| 15 | 23 | 48 |
| 16 | 26 | 106 |
| 17 | 28 | 40 |
| 18 | 81 | 80 |
| 19 | 5 | 18 |
| 20 | 2 | 91 |
| 21 | 73 | 77 |
| 22 | 24 | 50 |
| 23 | 23 | 49 |
| 24 | 46 | 39 |
| 25 | 80 | 71 |
| 26 | 26 | 33 |
| 27 | 5 | 29 |
| 28 | 23 | 63 |
| 29 | 24 | 14 |
| 30 | 16 | 56 |
| 31 | 14 | 1 |
| 32 | 18 | 5 |
| 33 | 22 | 22 |
| 34 | 43 | 127 |
| 35 | 28 | 28 |
| 36 | 78 | 81 |
| 37 | 13 | 106 |
| 38 | 6 | 4 |
| 39 | 92 | 70 |
| 40 | 29 | 8 |
| 41 | 57 | 70 |
| 42 | 27 | 9 |
| 43 | 9 | 11 |
| 44 | 20 | 0 |
| 45 | 9 | 4 |
| 46 | 38 | 25 |
| 47 | 1 | 55 |
| 48 | 16 | 21 |
| 49 | 13 | 18 |
| 50 | 86 | 101 |
| 51 | 100 | 87 |
| 52 | 36 | 100 |
| 53 | 106 | 82 |
| 54 | 63 | 35 |
| 55 | 75 | 45 |
| 56 | 30 | 71 |
| 57 | 88 | 50 |
| 58 | 88 | 116 |
| 59 | 100 | 87 |
| 60 | 67 | 96 |
| 61 | 72 | 49 |
| 62 | 81 | 51 |
| 63 | 68 | 58 |
| 64 | 109 | 86 |
| 65 | 57 | 80 |
| 66 | 30 | 77 |
| 67 | 82 | 64 |

Test 3: Evaluation of Reducing the Accumulation of α-Synuclein Aggregate with Neurospheroid Prepared from Human iPS Cells with a Mutation in PLA2G6 Gene (1) Induction of Differentiation from Human iPS Cell to Neural Cell Neural stem cells were induced from PLA2G6 gene mutant iPS cells with PSC Neuronal Induction Medium (Thermo Fisher Scientific Inc., cat #A1647801). Neurospheroid was prepared from the induced neural stem cells by three-dimensional culture system, and preserved with BrainPhys Neuronal Medium (STEMCELL Technologies, cat

ST-05793) comprising NeuroCult SM1 Neuronal Supplement, N2 Supplement-A, 20 ng/mL BDNF, 20 ng/mL GDNF, 1 mM dibutyryl cAMP, and 200 nM ascorbic acid. Half of the culture medium was replaced every 3 or 4 days after the induction of differentiation.

The test compound was diluted with the culture medium so as to be twice the final concentration, and an equal volume of the twice-concentrated solution was added to each well when half of the culture medium was replaced on day 10 after induction of differentiation.

(2) Evaluation of the Amount of α-Synuclein Aggregate

From the neurospheroid 15 days after the induction of differentiation, proteins were extracted with a TBS solution containing 1% TritionX-100, and the extracted proteins were subjected to a protein analysis with Simple Western system (Protein Simple, Inc., cat #SM-W008) using an α-synuclein antibody (Thermo Fisher Scientific Inc., cat #AHB0261) to measure the amount of the α-synuclein aggregate.

The amount of the aggregate in the neurospheroid added with each test compound was measured. Assuming that the amount of the aggregate in the neurospheroid added with a DMSO solution is 100%, the amount of the aggregate in the test samples was evaluated. Table 10 shows the amounts (%) of the aggregate for representative test compounds.

TABLE 10

| Example | Amount of aggregate (%) 100 nM | Amount of aggregate (%) 1000 nM |
| --- | --- | --- |
| 1 | 20 | 30 |
| 2 | 20 | 17 |
| 5 | 22 | 70 |
| 9 | 10 | 20 |
| 29 | 42 | 60 |
| 32 | 29 | 96 |
| 35 | 16 | 19 |
| 42 | 28 | 45 |
| 44 | 15 | 16 |
| 45 | 46 | 76 |

Test 4: Reproduction Test of Parkinson's Disease Pathology (Accumulation of α-Synuclein Aggregate) with Dopamine Neurospheroid Prepared from Human iPS Cells with a Mutation inPLA2G6 Gene Dopaminergic progenitor cells were induced from PLA2G6 gene mutant iPS cells with dopaminergic neuron differentiation kit (Thermo Fisher Scientific Inc., cat #A3147701) to prepare their cell stock.

The cryopreserved dopaminergic progenitor cells were cultured at 37° C. under 5% $CO_2$ with Floor Plate Cell expansion kit (Thermo Fisher Scientific Inc., cat #A3165801).

First, the dopaminergic progenitor cells (10000 cells/well) were seeded in 96-well round bottom plate (Thermo Fisher Scientific Inc., cat #174929), and cultured in a culture medium at 37° C. under 5% $CO_2$. Half of the culture medium was replaced every 3 or 4 days after the induction of differentiation. The culture medium used herein for dopamine neurospheroid had the following composition.

BrainPhys Neuronal Medium (STEMCELL Technologies, cat #ST-05793)
Dopaminergic Neuron Maturation Supplement (Thermo Fisher Scientific Inc., cat #A3147401)
20 ng/mL BDNF (PeproTech, Inc., cat #450-02)
20 ng/mL GDNF (PeproTech, Inc., cat #450-10)
1 mM dibutyryl cAMP (Nacalai Tesque, Inc., cat #11540-74)
200 nM ascorbic acid (Nacalai Tesque, Inc., cat #03420-52)

The differentiated dopamine neurospheroid was taken out from the culture medium, TBS solution (Nacalai Tesque, Inc., cat #12748-31) containing 1% TritionX-100 (Nacalai Tesque, Inc., cat #12967-32) was added thereto, and the protein was extracted from the mixture with an ultrasonicator.

The extracted protein was subjected to a protein analysis (Protein Simple, Inc., cat #SM-W008) under non-reducing conditions with Simple Western system using an α-synuclein antibody (Thermo Fisher Scientific Inc., cat #AHB0261) to measure the amount of the α-synuclein aggregate and evaluate the quantitation on the waveform shown at a molecular weight of about 300 kD.

Figure 2:
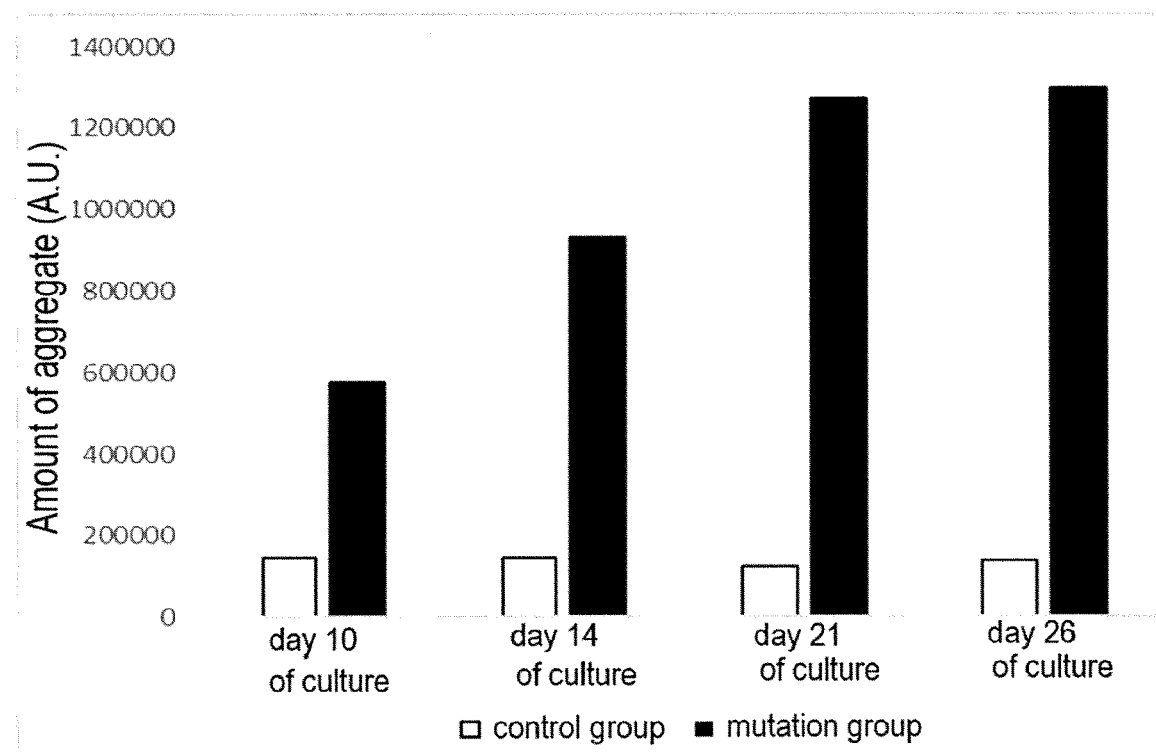
FIG. 2 shows the difference in the amount of aggregates in the dopamine neurospheroid derived from healthy human iPS cells and in the dopamine neurospheroid derived from PLA2G6 mutant iPS cells. The vertical axis indicates the amount of aggregate in dopamine neurospheroid, and the horizontal axis indicates the number of culture days. The white bars indicate the aggregate amount of in the neurospheroid derived from healthy human iPS cells, and the black bars indicate the aggregate amount of in the neurospheroid derived from PLA2G6 mutant iPS cells.

The α-synuclein aggregate increased sharply from day 10 to day 21 of the culture. On day 21 of the culture, the amount of the α-synuclein aggregate in the dopamine neurospheroid derived from PLA2G6 mutant iPS cells was 5 times or more that of the dopamine neurospheroid derived from healthy iPS cells. After day 21 of the culture, it showed a slow increasing trend. The result is shown in FIG. 2.

Test 5: Evaluation of Suppressing the Accumulation of α-Synuclein Aggregate with Dopamine Neurospheroid Prepared from Human iPS Cells with a Mutation in PLA2G6 Gene (1) Induction of Differentiation from Human iPS Cell to Neural Cell Dopaminergic progenitor cells were induced from PLA2G6 gene mutant iPS cells with dopaminergic neuron differentiation kit (Thermo Fisher Scientific Inc., cat #A3147701). Dopamine neurospheroid was prepared from the induced dopaminergic progenitor cells by three-dimensional culture system, and preserved with BrainPhys Neuronal Medium (STEMCELL Technologies, cat #ST-05793) comprising NeuroCult SM1 Neuronal Supplement, N2 Supplement-A, 20 ng/mL BDNF, 20 ng/mL GDNF, 1 mM dibutyryl cAMP, and 200 nM ascorbic acid. Half of the culture medium was replaced every 3 or 4 days after the induction of differentiation.

The test compound was diluted with the culture medium so as to be twice the final concentration, and an equal volume of the twice-concentrated solution was added to each well when half of the culture medium was replaced on day 21 after induction of differentiation.

(2) Evaluation of the Amount of α-Synuclein Aggregate

From the dopamine neurospheroid 26 days after the induction of differentiation, proteins were extracted with a TBS solution containing 1% TritionX-100, and the extracted proteins were subjected to a protein analysis with Simple Western system (Protein Simple, Inc., cat #SM-W008) using an α-synuclein antibody (Thermo Fisher Scientific Inc., cat #AHB0261) to measure the amount of the α-synuclein aggregate.

The amount of the aggregate in the neurospheroid added with each test compound was measured. Assuming that the amount of the aggregate in the neurospheroid added with a DMSO solution is 100%, the amount of the aggregate in the test samples was evaluated. Table 11 shows the amounts (%) of the aggregate for representative test compounds.

TABLE 11

| Example | Amount of aggregate (%) 100 nM | Amount of aggregate (%) 1000 nM |
| --- | --- | --- |
| 1 | 17 | 21 |
| 2 | 16 | 7 |

TABLE 11-continued

| Example | Amount of aggregate (%) 100 nM | Amount of aggregate (%) 1000 nM |
|---|---|---|
| 5 | 14 | 18 |
| 9 | 18 | 23 |
| 29 | 9 | 8 |
| 32 | 3 | 0 |
| 35 | 27 | 38 |
| 42 | 17 | 11 |
| 44 | 18 | 26 |
| 45 | 17 | 8 |

Figure 3:
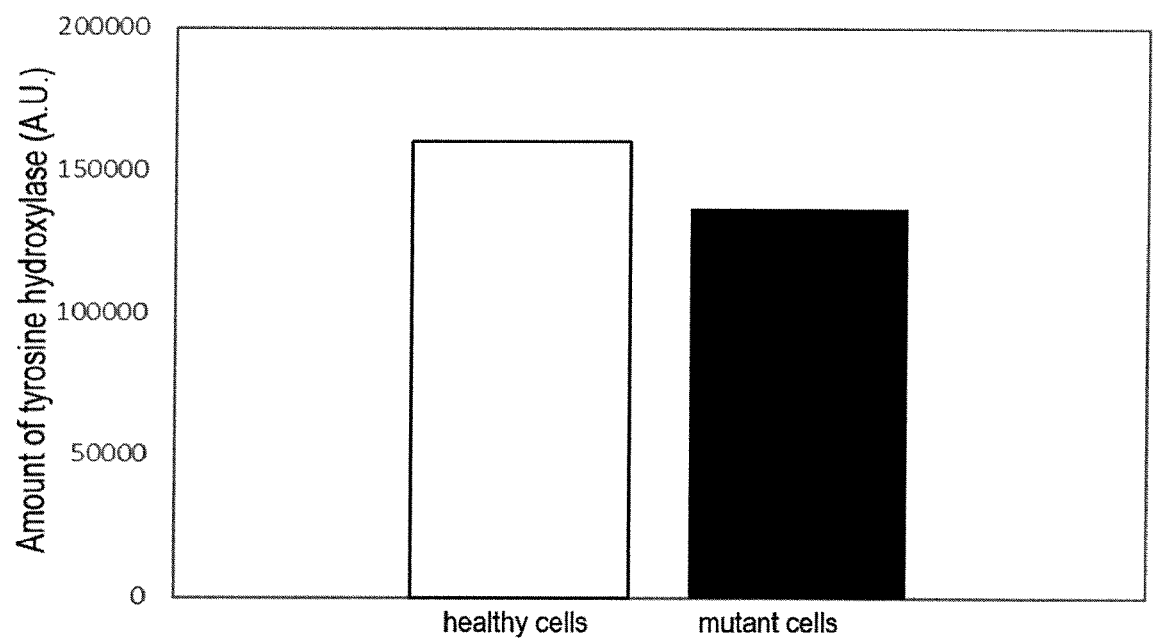
FIG. 3 shows the difference in the amount of tyrosine hydroxylase in the dopamine neurospheroid derived from healthy human iPS cells and in the dopamine neurospheroid derived from PLA2G6 mutant iPS cells on day 26 of culture. The vertical axis indicates the amount of tyrosine hydroxylase in dopamine neurospheroid. The white bar indicates the amount of tyrosine hydroxylase in the neurospheroid derived from healthy human iPS cells, and the black bar indicates the amount of tyrosine hydroxylase in the neurospheroid derived from PLA2G6 mutant iPS cells.

Test 6: Reproduction Method of Neural Vulnerability with Dopamine Neurospheroid Prepared from Human iPS Cells with a Mutation in PLA2G6 Gene
(1) Induction of Differentiation from Human iPS Cell to Neural Cell Dopaminergic progenitor cells were induced from PLA2G6 gene mutant iPS cells with dopaminergic neuron differentiation kit (Thermo Fisher Scientific Inc., cat #A3147701). Dopamine neurospheroid was prepared from the induced dopaminergic progenitor cells by three-dimensional culture system, and preserved with BrainPhys Neuronal Medium (STEMCELL Technologies, cat #ST-05793) comprising NeuroCult SM1 Neuronal Supplement, N2 Supplement-A, 20 ng/mL BDNF, 20 ng/mL GDNF, 1 mM dibutyryl cAMP, and 200 nM ascorbic acid. Half of the culture medium was replaced every 3 or 4 days after the induction of differentiation.
(2) Evaluation of the Amount of Tyrosine Hydroxylase From the dopamine neurospheroid 26 days after the induction of differentiation, proteins were extracted with a TBS solution containing 1% TritionX-100, and the extracted proteins were subjected to a protein analysis with Simple Western system (Protein Simple, Inc., cat #SM-W008) using a tyrosine hydroxylase antibody (Millipore, cat #AB152) to measure the amount of the tyrosine hydroxylase. The result is shown in FIG. 3.

Test 7: Evaluation of Improving Neural Vulnerability with Dopamine Neurospheroid Prepared from Human iPS Cells with a Mutation in PLA2G6 Gene
(1) Induction of Differentiation from Human iPS Cell to Neural Cell Dopaminergic progenitor cells are induced from PLA2G6 gene mutant iPS cells with dopaminergic neuron differentiation kit (Thermo Fisher Scientific Inc., cat #A3147701). Dopamine neurospheroid is prepared from the induced dopaminergic progenitor cells by three-dimensional culture system, and preserved with BrainPhys Neuronal Medium (STEMCELL Technologies, cat #ST-05793) comprising NeuroCult SM1 Neuronal Supplement, N2 Supplement-A, 20 ng/mL BDNF, 20 ng/mL GDNF, 1 mM dibutyryl cAMP, and 200 nM ascorbic acid. Half of the culture medium is replaced every 3 or 4 days.

The test compound is diluted with the culture medium so as to be twice the final concentration, and an equal volume of the twice-concentrated solution is added to each well when half of the culture medium is replaced on day 21 after induction of differentiation.
(2) Evaluation of the Amount of Tyrosine Hydroxylase From the dopamine neurospheroid 26 days after the induction of differentiation, proteins are extracted with a TBS solution containing 1% TritionX-100, and the extracted proteins are subjected to a protein analysis with Simple Western system (Protein Simple, Inc., cat #SM-W008) using a tyrosine hydroxylase antibody (Millipore, cat #AB152) to measure the amount of the tyrosine hydroxylase.

Figure 4:
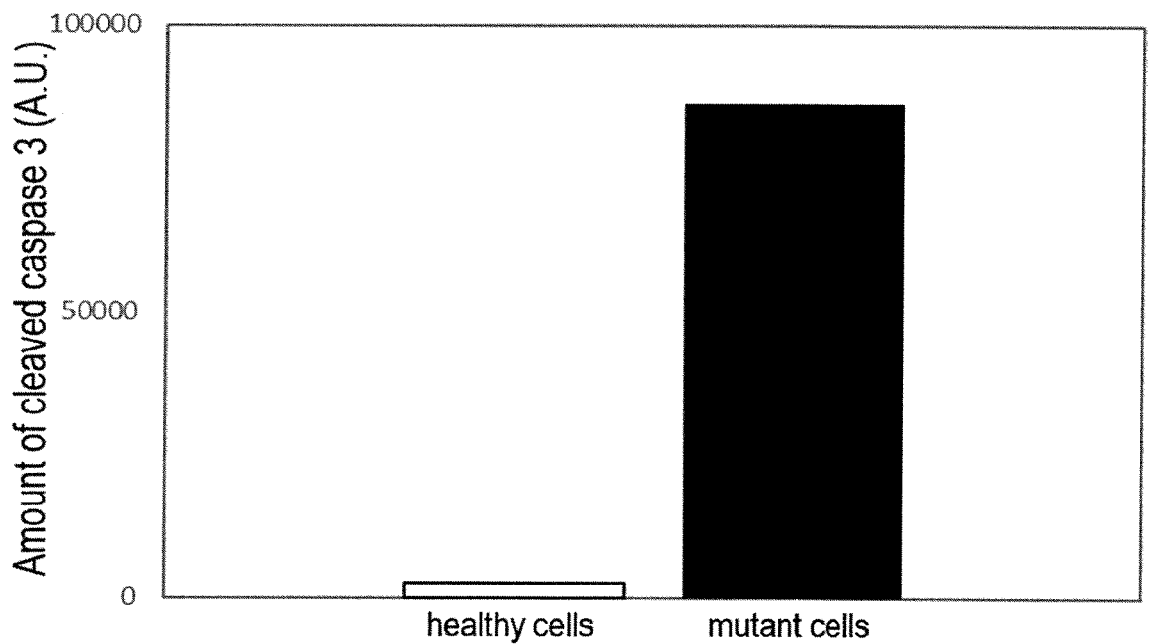
FIG. 4 shows the difference in the amount of cleaved caspase 3 in the dopamine neurospheroid derived from healthy human iPS cells and in the dopamine neurospheroid derived from PLA2G6 mutant iPS cells on day 40 of culture. The vertical axis indicates the amount of cleaved caspase 3 in dopamine neurospheroid. The white bar indicates the amount of cleaved caspase 3 in the neurospheroid derived from healthy human iPS cells, and the black bar indicates the amount of cleaved caspase 3 in the neurospheroid derived from PLA2G6 mutant iPS cells.

Test 8: Reproduction Method of Neuronal Cell Death with Neurospheroid Prepared from Human iPS Cells with a Mutation in PLA2G6 Gene
(1) Induction of Differentiation from Human iPS Cell to Neural Cell Dopaminergic progenitor cells were induced from PLA2G6 gene mutant iPS cells with dopaminergic neuron differentiation kit (Thermo Fisher Scientific Inc., cat #A3147701). Dopamine neurospheroid was prepared from the induced dopaminergic progenitor cells by three-dimensional culture system, and preserved with BrainPhys Neuronal Medium (STEMCELL Technologies, cat #ST-05793) comprising NeuroCult SM1 Neuronal Supplement, N2 Supplement-A, 20 ng/mL BDNF, 20 ng/mL GDNF, 1 mM dibutyryl cAMP, and 200 nM ascorbic acid. Half of the culture medium was replaced every 3 or 4 days.
(2) Evaluation of Neuronal Cell Death 10 µM Dopamine was added to the culture medium 35 days after the induction of differentiation. From the dopamine neurospheroid 40 days after the induction of differentiation, proteins were extracted with a TBS solution containing 1% TritionX-100, and the extracted proteins were subjected to a protein analysis with Simple Western system (Protein Simple, Inc., cat #SM-W008) using cleaved caspase 3 antibody (Cell Signaling Technology, Inc., cat #9664) to measure the amount of the neuronal cell death. The result is shown in FIG. 4.

Test 9: Evaluation of Suppressing Neuronal Cell Death with Neurospheroid Prepared from Human iPS Cells with a Mutation in PLA2G6 Gene
(1) Induction of Differentiation from Human iPS Cell to Neural Cell Dopaminergic progenitor cells are induced from PLA2G6 gene mutant iPS cells with dopaminergic neuron differentiation kit (Thermo Fisher Scientific Inc., cat #A3147701). Dopamine neurospheroid is prepared from the induced dopaminergic progenitor cells by three-dimensional culture system, and preserved with BrainPhys Neuronal Medium (STEMCELL Technologies, cat #ST-05793) comprising NeuroCult SM1 Neuronal Supplement, N2 Supplement-A, 20 ng/mL BDNF, 20 ng/mL GDNF, 1 mM dibutyryl cAMP, and 200 nM ascorbic acid. Half of the culture medium is replaced every 3 or 4 days.

The test compound is diluted with the culture medium so as to be twice the final concentration, and an equal volume of the twice-concentrated solution with 10 pM dopamine is added to each well when half of the culture medium is replaced on day 35 after induction of differentiation.
(2) Evaluation of Neuronal Cell Death From the dopamine neurospheroid 40 days after the induction of differentiation, proteins are extracted with a TBS solution containing 1% TritionX-100, and the extracted proteins are subjected to a protein analysis with Simple Western system (Protein Simple, Inc., cat #SM-W$^{008}$) using a cleaved caspase 3 antibody (Cell Signaling Technology, Inc., cat #9664) to measure the amount of the neuronal cell death.

Test 10: Reproduction Method of Parkinson's Disease Pathology (Accumulation of α-Synuclein Aggregate) with Neurospheroid Prepared by Three-Dimensional Culture of Human iPS Cells with a Mutation in GBA1 Gene GBA1 gene homozygous mutant cells established from healthy human-derived iPS cell line was cultured in StemFitAKO3N medium (Ajinomoto Co., Inc., Basic03) at 37° C. under 5% $CO_2$.

Dopaminergic progenitor cells were induced from GBA1 homozygous mutant iPS cells with dopaminergic neuron differentiation kit (Thermo Fisher Scientific Inc., cat #A3147701) to prepare their cell stock.

The cryopreserved dopaminergic progenitor cells were cultured in culture medium at 37° C. under 5% $CO_2$ with Floor Plate Cell expansion kit (Thermo Fisher Scientific Inc., cat #A3165801).

The dopaminergic progenitor cells (10000 cells/well) were seeded in 96-well round bottom plate (Thermo Fisher Scientific Inc., cat #174929), and cultured in a culture medium at 37° C. under 5% $CO_2$. Half of the culture solution was replaced every 3 to 4 days after the induction of differentiation. The culture medium used herein for dopamine neurospheroid had the following composiiton.

BrainPhys Neuronal Medium (STEMCELL Technologies, cat #ST-05793)
Dopaminergic Neuron Maturation Supplement (Thermo Fisher Scientific Inc., cat #A3147401)
20 ng/mL BDNF (PeproTech, Inc., cat #450-02)
20 ng/mL GDNF (PeproTech, Inc., cat #450-10)
1 mM dibutyryl cAMP (Nacalai Tesque, Inc., cat #11540-74)
200 nM ascorbic acid (Nacalai Tesque, Inc., cat #03420-52)

The differentiation-induced dopamine neurospheroid was taken out from the culture medium, TBS solution (Nacalai Tesque, Inc., cat #12748-31) containing 1% TritionX-100 (Nacalai Tesque, Inc., cat #12967-32) was added thereto, and the protein was extracted from the mixture with an ultrasonicator.

The extracted protein was subjected to a protein analysis under non-reducing conditions with Simple Western system (Protein Simple, Inc., cat #SM-W008) using an α-synuclein antibody (Thermo Fisher Scientific Inc., cat #AHB0261) to measure the amount of the α-synuclein aggregate and evaluate the quantitation on the waveform shown at a molecular weight of about 300 kD.

Figure 5:
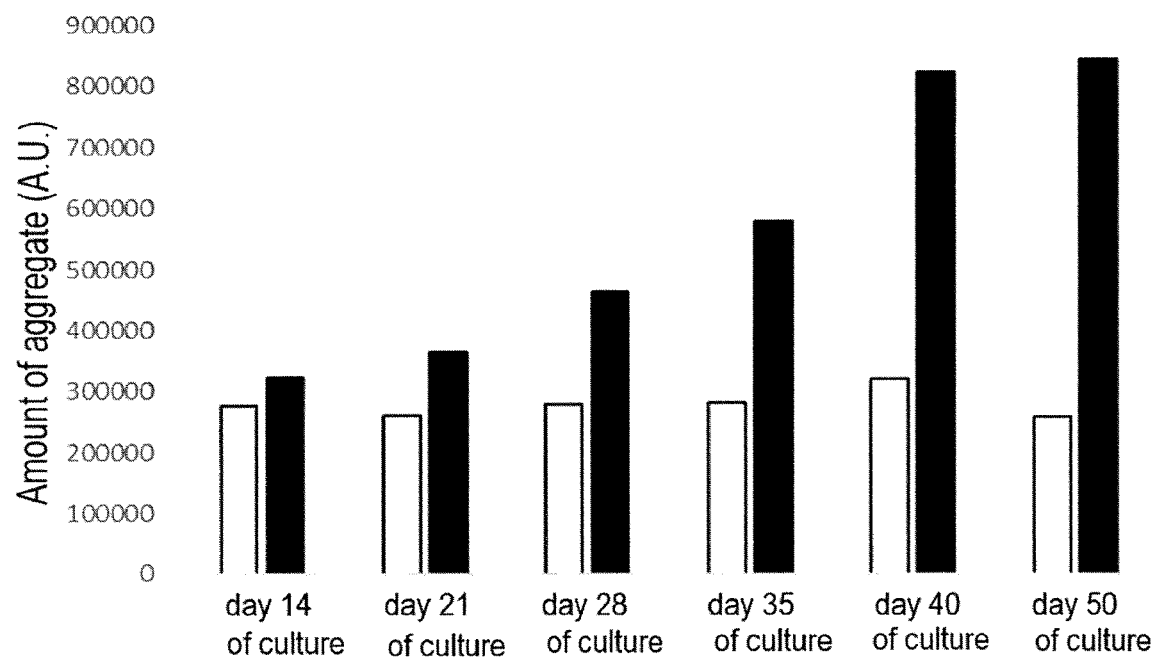
FIG. 5 shows the difference in the amount of aggregates in the dopamine neurospheroid derived from healthy human iPS cells and in the dopamine neurospheroid derived from GBA1 gene homozygous mutant iPS cells. The vertical axis indicates the amount of aggregate in dopamine neurospheroid, and the horizontal axis indicates the number of culture days. The white bars indicate the aggregate amount of in the neurospheroid derived from healthy human iPS cells, and the black bars indicate the aggregate amount of in the neurospheroid derived from GBA1 gene homozygous mutant iPS cells.

The α-synuclein aggregate increased sharply from day 21 to day 40 of the culture. On day 40 of the culture, the amount of the aggregate reached saturation, after which no change in the amount was observed. The result is shown in FIG. 5.

Test 11: Evaluation of Reducing the Accumulation of α-Synuclein Aggregate with Dopamine Neurospheroid Prepared from Human iPS Cells with a Mutation in GBA1 Gene (1) Induction of Differentiation from Human iPS Cell to Neural Cell Dopaminergic progenitor cells were induced from GBA1 gene mutant iPS cells with dopaminergic neuron differentiation kit (Thermo Fisher Scientific Inc., cat #A3147701). Dopamine neurospheroid was prepared from the induced dopaminergic progenitor cells by three-dimensional culture system, and preserved with BrainPhys Neuronal Medium (STEMCELL Technologies, cat #ST-05793) comprising NeuroCult SM1 Neuronal Supplement, N2 Supplement-A, 20 ng/mL BDNF, 20 ng/mL GDNF, 1 mM dibutyryl cAMP, and 200 nM ascorbic acid. Half of the culture medium was replaced every 3 or 4 days.

The test compound was diluted with the culture medium so as to be twice the final concentration, and an equal volume of the twice-concentrated solution was added to each well when half of the culture medium was replaced on day 40 after induction of differentiation.

(2) Evaluation of the Amount of α-Synuclein Aggregate

From the dopamine neurospheroid 44 days after the induction of differentiation, proteins were extracted with a TBS solution containing 1% TritionX-100, and the extracted proteins were subjected to a protein analysis with Simple Western system (Protein Simple, Inc., cat #SM-W008) using an α-synuclein antibody (Thermo Fisher Scientific Inc., cat #AHB0261) to measure the amount of the α-synuclein aggregate.

The amount of the aggregate in the neurospheroid added with each test compound was measured. Assuming that the amount of the aggregate in the neurospheroid added with a DMSO solution is 100%, the amount of the aggregate in the test samples was evaluated. Table 12 shows the amounts (%) of the aggregate for representative test compounds.

TABLE 12

| Example | Amount of aggregate (%) 100 nM | Amount of aggregate (%) 1000 nM |
|---|---|---|
| 1 | 23 | 14 |
| 2 | 21 | 20 |
| 42 | 18 | 8 |
| 44 | 20 | 24 |

Test 12: Check of Synchronous Firing Abnormality with Neurospheroid Prepared by Three-Dimensional Culture of Human iPS Cells with a Mutation in GBA1 Gene GBA1 gene homozygous mutant cells established from healthy human-derived iPS cell line is cultured in StemFitAKO3N medium (Ajinomoto Co., Inc., Basic03) at 37° C. under 5% $CO_2$.

Dopaminergic progenitor cells are induced from GBA1 homozygous mutant iPS cells with dopaminergic neuron differentiation kit (Thermo Fisher Scientific Inc., cat #A3147701) to prepare their cell stock.

The cryopreserved dopaminergic progenitor cells are cultured at 37° C. under 5% $CO_2$ with Floor Plate Cell expansion kit (Thermo Fisher Scientific Inc., cat #A3165801).

The dopaminergic progenitor cells (10000 cells/well) are seeded in 96-well round bottom plate (Thermo Fisher Scientific Inc., cat #174929), and cultured in a culture medium at 37° C. under 5% $CO_2$. Half of the culture solution is replaced every 3 to 4 days after the induction of differentiation. The culture medium used herein for dopamine neurospheroid has the following composition.

BrainPhys Neuronal Medium (STEMCELL Technologies, cat #ST-05793)
Dopaminergic Neuron Maturation Supplement (Thermo Fisher Scientific Inc., cat #A3147401)
20 ng/mL BDNF (PeproTech, Inc., cat #450-02)
20 ng/mL GDNF (PeproTech, Inc., cat #450-10)
1 mM dibutyryl cAMP (Nacalai Tesque, Inc., cat #11540-74)
200 nM ascorbic acid (Nacalai Tesque, Inc., cat #03420-52)

On day 40 or later after the induction of differentiation, half of the culture medium is removed, a measurement medium containing fluorescent calcium probe (Molecular Devices, Product name: FLIPR Calcium 6 Assay Bulk Kit, cat #R8191) is added equal to the remaining medium, and the mixture is stood for 30 minutes and then measured. The measurement medium used herein is 20 mM Hepes (Thermo Fisher Scientific Inc., cat #15630-080), and Hank's buffer solution (Thermo Fisher Scientific Inc., cat #14065-056) containing 0.1% bovine serum albumin (Sigma-Aldrich, cat #A9576). Shooting takes one frame per second.

Test 13: Evaluation of Improving Synchronous Firing Abnormality with Dopamine Neurospheroid Prepared by Human iPS Cells with a Mutation in GBA1 Gene (1) Induction of Differentiation from Human iPS Cell to Neural Cell Dopaminergic progenitor cells are induced from GBA1 gene mutant iPS cells with dopaminergic neuron differentiation kit (Thermo Fisher Scientific Inc., cat #A3147701). Dopamine neurospheroid is prepared from the induced dopaminergic progenitor cells by three-dimensional culture system, and preserved with BrainPhys Neuronal Medium (STEMCELL Technologies, cat #ST-05793) comprising NeuroCult SM1 Neuronal Supplement, N2 Supplement-A, 20 ng/mL BDNF, 20 ng/mL GDNF, 1 mM dibutyryl cAMP, and 200 nM ascorbic acid. Half of the culture medium is replaced every 3 or 4 days.

The test compound is diluted with the culture medium so as to be twice the final concentration, and an equal volume of the twice-concentrated solution is added to each well when half of the culture medium is replaced on day 40 after induction of differentiation.

(2) Evaluation of Synchronous Firing

On day 44 after the induction of differentiation, half of the culture medium of dopamine neurospheroid is removed, a measurement medium containing fluorescent calcium probe (Molecular Devices, Product name: FLIPR Calcium 6 Assay Bulk Kit, cat #R8191) is added equal to the remaining medium, and the mixture is stood for 30 minutes and then measured. The measurement medium used herein is 20 mM Hepes (Thermo Fisher Scientific Inc., cat #15630-080), and Hank's buffer solution (Thermo Fisher Scientific Inc., cat #14065-056) containing 0.1% bovine serum albumin (Sigma-Aldrich, cat #A9576). Shooting takes one frame per second.

INDUSTRIAL APPLICABILITY

The present compound has an action of suppressing or reducing the accumulation of α-synuclein aggregates, and thereby the present compound is useful as a medicament for treating or preventing central nervous system disease, which is characterized by an action of suppressing or reducing the accumulation of abnormal aggregation of proteins in the brain. In addition, the present invention is useful as a method for reproducing Parkinson's disease pathology with neurospheroids, and a method for evaluating the amount of α-synuclein aggregates using the reproducing method.

As explained above, the compound of formula (1) or a pharmaceutically acceptable salt thereof has an action of suppressing or reducing the accumulation of α-synuclein aggregates. Thus, the compound of formula (1) or a pharmaceutically acceptable salt thereof is useful as a medicament for treating or preventing central nervous system disease related to α-synuclein aggregates such as Parkinson's disease, and dementia with Lewy body.

The invention claimed is:

1. A compound of the following formula (1):

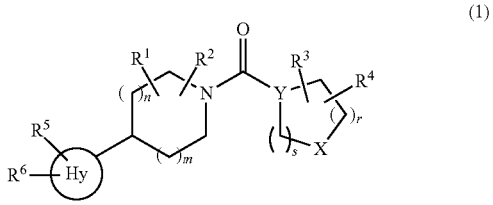

or a pharmaceutically acceptable salt thereof, wherein
X is oxygen or $NR^7$, $R^7$ is hydrogen, $C_{1-3}$ alkyl optionally substituted with 1 to 3 the same or different halogen atoms, or cyclopropyl, Y is CH or nitrogen, m is 1, n is 1, r is 0, 1, 2, 3, or 4, s is 0, 1, or 2, provided that when s is 0, then Y is CH, and r is 1, 2, 3, or 4, when s is 1, then Y is CH, and r is 0, 1, 2, or 3, and when s is 2, then r is 1 or 2, $R^1$ is hydrogen, halogen, methyl, or hydroxy, $R^2$ is hydrogen, halogen, methyl, or hydroxy, $R^3$ is hydrogen, or $C_{1-3}$ alkyl, $R^4$ is hydrogen, or $C_{1-3}$ alkyl, or, $R^3$ and $R^4$ optionally together form a bridged methylene or a bridged ethylene, $R^5$ is halogen, $C_{1-3}$ alkyl optionally substituted with 1 to 3 the same or different halogen atoms, or $C_{1-3}$ alkoxy optionally substituted with 1 to 3 the same or different halogen atoms, $R^6$ is hydrogen, halogen, $C_{1-3}$ alkyl optionally substituted with 1 to 3 the same or different halogen atoms, or $C_{1-3}$ alkoxy optionally substituted with 1 to 3 the same or different halogen atoms, and Hy is pyridine ring, pyridazine ring, pyrimidine ring, or pyrazine ring, provided that (I) when Hy accompanied with $R^5$ and $R^6$ is 5-fluoropyridin-2-yl, and m and n are 1, then r is 0, and s is 1, (II) when Hy accompanied with $R^5$ and $R^6$ is 6-methoxypyridin-3-yl, m and n are 1, and X is oxygen, then r is 0, and s is 1, (III) when Hy accompanied with $R^5$ and $R^6$ is 5-methoxypyridin-2-yl, m and n are 1, and X is $NR^7$, then r is 0, and s is 1, (IV) when $R^5$ is methyl, and $R^6$ is hydrogen, then r is 0, and s is 1, but, (I') Hy accompanied with R5 and R6 is not 4,6-dimethylpyrimidin-2-yl, or 5-bromopyrimidin-2-yl, (II') when Hy accompanied with R5 and R6 is 5-chloropyridin-2-yl, then m and n are 1, and both $R^1$ and $R^2$ are not hydrogen.

2. The compound of claim 1 or a pharmaceutically acceptable salt thereof, wherein $R^1$ and $R^2$ are independently hydrogen, methyl, or fluorine.

3. The compound of claim 1 or a pharmaceutically acceptable salt thereof, wherein $R^1$ and $R^2$ are hydrogen.

4. The compound of claim 1 or a pharmaceutically acceptable salt thereof, wherein X is oxygen, NH, or NMe.

5. The compound of claim 1 or a pharmaceutically acceptable salt thereof, wherein $R^3$ is hydrogen.

6. The compound of claim 1 or a pharmaceutically acceptable salt thereof, wherein $R^4$ is methyl or ethyl.

7. The compound of claim 1 or a pharmaceutically acceptable salt thereof, wherein Y is CH.

8. The compound of claim 1 or a pharmaceutically acceptable salt thereof, wherein s is 1.

9. The compound of claim 1 or a pharmaceutically acceptable salt thereof, wherein r is 0, and s is 1.

10. The compound of claim 1 or a pharmaceutically acceptable salt thereof, wherein the compound is represented by the following formula (2):

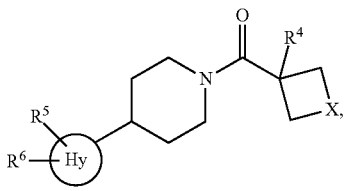

(2)

wherein
X is oxygen, NH, or NMe,
R⁴ is methyl or ethyl,
R⁵ is halogen, $C_{1-3}$ alkyl optionally substituted with 1 to 3 the same or different halogen atoms, or $C_{1-3}$ alkoxy optionally-substituted with 1 to 3 the same or different halogen atoms,
R⁶ is hydrogen, halogen, $C_{1-3}$ alkyl optionally substituted with 1 to 3 the same or different halogen atoms, or $C_{1-3}$ alkoxy optionally-substituted with 1 to 3 the same or different halogen atoms, and
Hy is pyridine ring, pyridazine ring, pyrimidine ring, or pyrazine ring,
provided that Hy accompanied with R⁵ and R⁶ is not 5-chloropyridin-2-yl.

11. The compound of claim 1 or a pharmaceutically acceptable salt thereof, wherein Hy is pyridine ring.

12. The compound of claim 1 or a pharmaceutically acceptable salt thereof, wherein R⁵ is trifluoromethyl.

13. The compound of claim 1 or a pharmaceutically acceptable salt thereof, wherein Hy is pyridin-3-yl.

14. The compound of claim 1 or a pharmaceutically acceptable salt thereof, wherein X is oxygen.

15. The compound of claim 1 or a pharmaceutically acceptable salt thereof, wherein R⁴ is methyl.

16. The compound of claim 1 or a pharmaceutically acceptable salt thereof, wherein X is NH or NMe.

17. The compound of claim 1 or a pharmaceutically acceptable salt thereof, wherein X is NMe.

18. The compound of claim 1 or a pharmaceutically acceptable salt thereof, selected from the group consisting of:
(3-methyloxetan-3-yl){4-[6-(trifluoromethyl) pyridin-3-yl]piperidin-1-yl}methanone,
(3-methyloxetan-3-yl){4-[5-(trifluoromethyl)pyridin-3-yl]piperidin-1-yl}methanone,
(3-methyloxetan-3-yl) {4-[4-(trifluoromethyl)pyridin-3-yl]piperidin-1-yl}methanone,
(3-methyloxetan-3-yl){4-[2-(trifluoromethyl)pyridin-3-yl]piperidin-1-yl}methanone,
{4-[5-fluoro-6-(trifluoromethyl)pyridin-3-yl]piperidin-1-yl}(3-methyloxetan-3-yl)methanone,
(3-methyloxetan-3-yl){4-[4-methyl-6-(trifluoromethyl)pyridin-3-yl]piperidin-1-yl}methanone,
(1,3-dimethylazetidin-3-yl){4-[6-(trifluoromethyl) pyridin-3-yl]piperidin-1-yl}methanone,
(1,3-dimethylazetidin-3-yl){4-[2-(trifluoromethyl) pyridin-3-yl]piperidin-1-yl}methanone,
(1,3-dimethylazetidin-3-yl){4-[4-(trifluoromethyl) pyridin-3-yl]piperidin-1-yl}methanone, and
(1,3-dimethylazetidin-3-yl){4-[5-(trifluoromethyl) pyridin-3-yl]piperidin-1-yl}methanone.

19. A composition comprising the compound of claim 1 or a pharmaceutically acceptable salt thereof as an active ingredient.

20. A method for treating central nervous system disease whose cause is related to abnormal aggregation of proteins in the brain, the method comprising administering as an active ingredient a compound of the following formula (1) to a subject in need thereof:

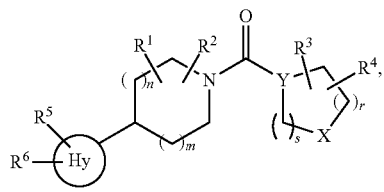

(1)

wherein
X is oxygen or NR⁷,
R⁷ is hydrogen, $C_{1-3}$ alkyl optionally substituted with 1 to 3 the same or different halogen atoms, or cyclopropyl,
Y is CH or nitrogen,
m is 1,
n is 1,
r is 0, 1, 2, 3, or 4,
s is 0, 1, or 2,
provided that when s is 0, then Y is CH, and r is 1, 2, 3, or 4,
when s is 1, then Y is CH, and r is 0, 1, 2, or 3, and
when s is 2, then r is 1 or 2,
R¹ is hydrogen, halogen, methyl, or hydroxy,
R² is hydrogen, halogen, methyl, or hydroxy,
R³ is hydrogen, or $C_{1-3}$ alkyl,
R⁴ is hydrogen, or $C_{1-3}$ alkyl,
or, R³ and R⁴ may be optionally together form a bridged methylene or a bridged ethylene,
R⁵ is hydrogen, halogen, $C_{1-3}$ alkyl optionally substituted with 1 to 3 the same or different halogen atoms, or $C_{1-3}$ alkoxy optionally-substituted with 1 to 3 the same or different halogen atoms,
R⁶ is hydrogen, halogen, $C_{1-3}$ alkyl optionally substituted with 1 to 3 the same or different halogen atoms, or $C_{1-3}$ alkoxy optionally substituted with 1 to 3 the same or different halogen atoms, and
Hy is pyridine ring, pyridazine ring, pyrimidine ring, or pyrazine ring, or a pharmaceutically acceptable salt thereof.

21. The method of claim 20, wherein R¹ and R² are independently hydrogen, methyl, or fluorine.

22. The method of claim 20, wherein R¹ and R² are hydrogen.

23. The method of claim 20, wherein X is oxygen, NH, or NMe.

24. The method of claim 20, wherein R³ is hydrogen.

25. The method of claim 20, wherein R⁴ is methyl or ethyl.

26. The method of claim 20, wherein Y is CH.

27. The method of claim 20, wherein s is 1.

28. The method of claim 20, wherein r is 0, and s is 1.

29. The method of claim 20, wherein the compound is represented by the following formula (2):

(2)

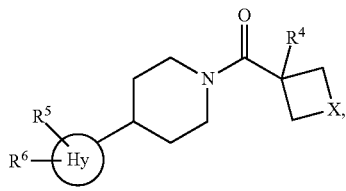

wherein
X is oxygen, NH, or NMe,
R⁴ is methyl or ethyl,
R⁵ is hydrogen, halogen, $C_{1-3}$ alkyl optionally substituted with 1 to 3 the same or different halogen atoms, or $C_{1-3}$ alkoxy optionally substituted with 1 to 3 the same or different halogen atoms,
R⁶ is hydrogen, halogen, $C_{1-3}$ alkyl optionally substituted with 1 to 3 the same or different halogen atoms, or $C_{1-3}$ alkoxy optionally substituted with 1 to 3 the same or different halogen atoms, and
Hy is pyridine ring, pyridazine ring, pyrimidine ring, or pyrazine ring.

30. The method of claim 20, wherein Hy is pyridine ring.
31. The method of claim 20, wherein R⁵ is trifluoromethyl.
32. The method of claim 20, wherein Hy is pyridin-3-yl.
33. The method of claim 20, wherein X is oxygen.
34. The method of claim 20, wherein R⁴ is methyl.
35. The method of claim 20, wherein X is NH or NMe.
36. The method of claim 20, wherein X is NMe.
37. The method of claim 20, wherein the central nervous system disease is related to tau, α-synuclein, TDP-43, or polyglutamine.
38. The method of claim 20, wherein the central nervous system disease is Alzheimer's disease, frontotemporal lobar degeneration, Parkinson's disease, dementia with Lewy body, multiple system atrophy, Gaucher disease, infantile neuroaxonal dystrophy, amyotrophic lateral sclerosis, Huntington's disease, or spinocerebellar ataxia.
39. The method of claim 20, wherein the central nervous system disease is related to α-synuclein.
40. The method of claim 20, wherein the central nervous system disease is Parkinson's disease, dementia with Lewy body, multiple system atrophy, Gaucher disease, or infantile neuroaxonal dystrophy.
41. The method of claim 20, comprising administering as an active ingredient the compound of the formula (1) or a pharmaceutically acceptable salt thereof in combination with at least one agent selected from the group consisting of L-dopa, a dopamine agonist, an MAO-B inhibitor, a catechol-O-methyltransferase (COMT) inhibitor, αSyn antibody, and a pharmaceutically acceptable salt thereof, to the.
42. A process for preparing a compound of the following formula (3):

(3)

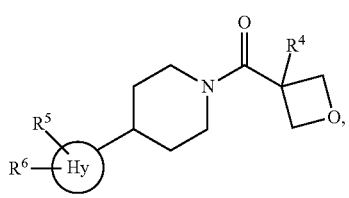

or a pharmaceutically acceptable salt thereof,
wherein
R⁴ is methyl or ethyl,
R⁵ is trifluoromethyl,
R⁶ is hydrogen, halogen, $C_{1-3}$ alkyl optionally substituted with 1 to 3 the same or different halogen atoms, or $C_{1-3}$ alkoxy optionally-substituted with 1 to 3 the same or different halogen atoms, and
Hy is pyridin-3-yl,
the process comprising:
condensing a compound of the following formula (4):

(4)

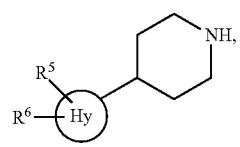

wherein R⁵, R⁶, and Hy are as defined above, or a salt thereof with a compound of the following formula (5):

(5)

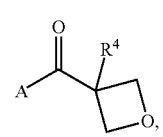

wherein R⁴ is as defined above, and A is OH or halogen, or a salt thereof to prepare a compound of the formula (3) or a pharmaceutically acceptable salt thereof.

43. A process for preparing a compound of the following formula (6):

(6)

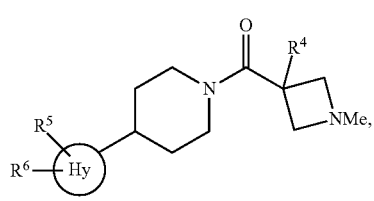

or a pharmaceutically acceptable salt thereof,
wherein
R⁴ is methyl,
R⁵ is trifluoromethyl,
R⁶ is hydrogen, halogen, $C_{1-3}$ alkyl optionally substituted with 1 to 3 the same or different halogen atoms, or $C_{1-3}$ alkoxy optionally substituted with 1 to 3 the same or different halogen atoms, and
Hy is pyridin-3-yl,
the process comprising:
condensing a compound of the following formula (4):

(4)

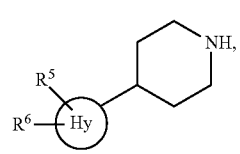

wherein $R^5$, $R^6$, and Hy are as defined above, or a salt thereof with a compound of the following formula (7):

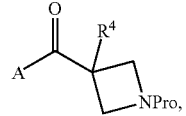

(7)

wherein $R^4$ is as defined above, A is OH or halogen, and Pro is an amino-protecting group, or a salt thereof to prepare a compound of the following formula (8):

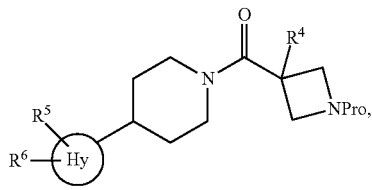

(8)

wherein $R^4$, $R^5$, $R^6$, Hy, and Pro are as defined above, or a pharmaceutically acceptable salt thereof, deprotecting the amino-protecting group in the compound of the formula (8) or a salt thereof to prepare a compound of the following formula (9):

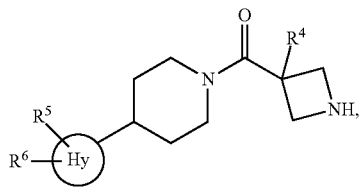

(9)

wherein $R^4$, $R^5$, $R^6$, and Hy are as defined above, or a salt thereof, reacting the compound of the formula (9) or a salt thereof with formaldehyde or its equivalent compound in the presence of a reducing agent to prepare the compound of the formula (6) or a pharmaceutically acceptable salt thereof.

* * * * *